(12) United States Patent
Ulitin et al.

(10) Patent No.: US 12,410,257 B2
(45) Date of Patent: Sep. 9, 2025

(54) MONOCLONAL ANTIBODY THAT BINDS SPECIFICALLY TO GITR

(71) Applicant: JOINT STOCK COMPANY "BIOCAD", Saint Petersburg (RU)

(72) Inventors: Andrei Borisovich Ulitin, Puschino (RU); Olesya Nikolaevna Kozlova, Saint Petersburg (RU); Aleksandr Andreevich Gordeev, Izhevsk (RU); Ksenia Mihailovna Burnysheva, Moscow (RU); Anastasia Nikolaevna Ishutinova, Chekhov (RU); Aleksandra Aleksandrovna Sozonova, Severodvinsk (RU); Sergei Andreevich Ageev, Chehov (RU); Aleksandr Nikolaevich Doronin, Moscow (RU); Vladimir Sergeevich Tsympilov, Zakulta (RU); Ivan Vladimirovich Mitroshin, Izhevsk (RU); Valery Vladimirovich Solovyev, Pushchino (RU); Iakov Iurevich Ustiugov, Berezniki (RU); Roman Alekseevich Ivanov, Moscow (RU); Dmitry Valentinovich Morozov, Saint Petersburg (RU)

(*) Notice: Subject to any disclaimer, the term of this patent is extended or adjusted under 35 U.S.C. 154(b) by 792 days.

(21) Appl. No.: 17/605,933

(22) PCT Filed: Apr. 23, 2020

(86) PCT No.: PCT/RU2020/050080
§ 371 (c)(1),
(2) Date: Oct. 22, 2021

(87) PCT Pub. No.: WO2020/218951
PCT Pub. Date: Oct. 29, 2020

(65) Prior Publication Data
US 2022/0213209 A1    Jul. 7, 2022

(30) Foreign Application Priority Data

Apr. 23, 2019  (RU) .......................... RU2019112296

(51) Int. Cl.
*C07K 16/28* (2006.01)
*A61P 35/00* (2006.01)
*C07K 16/46* (2006.01)

(52) U.S. Cl.
CPC .......... *C07K 16/2878* (2013.01); *A61P 35/00* (2018.01); *C07K 16/46* (2013.01); *C07K 2317/21* (2013.01); *C07K 2317/22* (2013.01); *C07K 2317/24* (2013.01); *C07K 2317/33* (2013.01); *C07K 2317/55* (2013.01); *C07K 2317/565* (2013.01); *C07K 2317/732* (2013.01); *C07K 2317/76* (2013.01); *C07K 2317/94* (2013.01)

(58) Field of Classification Search
CPC .......................... C07K 16/2878; C07K 16/46; C07K 2317/21; C07K 2317/22; C07K 2317/24; C07K 2317/33; C07K 2317/55; C07K 2317/565; C07K 2317/732; C07K 2317/76; C07K 2317/94; A61P 35/00
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,634,665 A | 1/1987 | Axel et al. |
| 4,740,461 A | 4/1988 | Kaufman |
| 4,816,567 A | 3/1989 | Cabilly et al. |
| 4,912,040 A | 3/1990 | Kaufman et al. |
| 4,959,455 A | 9/1990 | Clark et al. |
| 4,968,615 A | 11/1990 | Koszinowski et al. |
| 5,168,062 A | 12/1992 | Stinski |
| 5,179,017 A | 1/1993 | Axel et al. |
| 5,229,275 A | 7/1993 | Goroff |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,571,894 A | 11/1996 | Wells et al. |
| 5,587,458 A | 12/1996 | King et al. |

(Continued)

FOREIGN PATENT DOCUMENTS

| | | |
|---|---|---|
| CA | 3042727 A1 | 5/2018 |
| CA | 3054885 A1 | 9/2018 |

(Continued)

OTHER PUBLICATIONS

Schroeder and Cavacini (Journal of Allergy and Clinical Immunology (2010) 125(2, Suppl.2): S41-S52) (Year: 2010).*

(Continued)

*Primary Examiner* — Julie Wu
*Assistant Examiner* — Elizabeth A Shupe
(74) *Attorney, Agent, or Firm* — Anglehart et al.

(57) ABSTRACT

The present invention relates to biotechnology, in particular to antibodies or antigen-binding fragments thereof, and to use thereof. More particularly, the present invention relates to monoclonal antibodies that specifically bind to GITR. The invention also relates to a nucleic acid encoding said antibody or antigen-binding fragment thereof, an expression vector, a method for preparing said antibody, and use of said antibody in treatment of diseases or disorders associated with GITR.

26 Claims, 26 Drawing Sheets

Specification includes a Sequence Listing.

(56) References Cited

U.S. PATENT DOCUMENTS

| | | | |
|---|---|---|---|
| 5,591,669 | A | 1/1997 | Krimpenfort et al. |
| 5,641,870 | A | 6/1997 | Rinderknecht et al. |
| 6,517,529 | B1 | 2/2003 | Quinn |
| 2015/0353637 | A1 | 12/2015 | Wang et al. |
| 2018/0044430 | A1* | 2/2018 | Chiu .................... A61P 35/00 |
| 2018/0289790 | A1 | 10/2018 | Engelhardt et al. |
| 2018/0355051 | A1 | 12/2018 | Gonzalez et al. |

FOREIGN PATENT DOCUMENTS

| | | | |
|---|---|---|---|
| CN | 107530423 | A | 1/2018 |
| EP | 0256055 | B1 | 8/1991 |
| EP | 0323997 | B1 | 4/1993 |
| EP | 0338841 | B1 | 3/1995 |
| EP | 0216846 | B2 | 4/1995 |
| JP | 2017-523771 | A | 8/2017 |
| RU | 2369636 | C2 | 10/2009 |
| RU | 2595409 | C2 | 8/2016 |
| RU | 2646139 | C1 | 3/2018 |
| WO | 93/16185 | A2 | 8/1993 |
| WO | 97/17852 | A1 | 5/1997 |
| WO | 2005/047327 | A2 | 5/2005 |
| WO | 2006/104989 | A2 | 10/2006 |
| WO | 2007/005612 | A2 | 1/2007 |
| WO | 2015/031667 | A2 | 3/2015 |
| WO | 2015/187835 | A2 | 12/2015 |
| WO | 2017/068186 | A1 | 4/2017 |
| WO | 2017/096189 | A1 | 6/2017 |
| WO | 2017/214548 | A1 | 12/2017 |
| WO | 2018/005950 | A1 | 1/2018 |
| WO | 2018/031400 | A1 | 2/2018 |
| WO | 2018/145075 | A1 | 8/2018 |

OTHER PUBLICATIONS

Sela-Culang et al. (Frontiers in Immunology (2013) 4: 302) (Year: 2013).*

Almagro et al., Frontiers in Immunology (2018) 8: 1751 (Year: 2018).*

Corresponding European application No. 20794288.9 extended European search report dated Nov. 30, 2022.

Corresponding Chinese application No. 201911222245.8 Office Action dated Mar. 1, 2023 (translation provided).

Kaja D. Biederbick, et al., Efficacy of cytokine-induced killer cells targeting CD40 and GITR. Oncology Letters. Feb. 2019 (published online on Dec. 18, 2018). vol. 17 Issue 2. pp. 2425-2430.

Susumu Ohno, et al., Antigen-binding specificities of antibodies are primarily determined by seven residues of VH. Proc. Natl. Acad. Sci. USA. vol. 82, pp. 2945-2949, May 1985. Immunolgy.

Stuart Rudikoff, et al., Single amino acid substitution altering antigen-binding specificity. Proc. Natl. Acad. Sci. USA. vol. 79, pp. 1979-1983, Mar. 1982. Immunolgy.

Corresponding Japanese application No. 2021-563239 Office Action dated Apr. 4, 2023 (translation provided).

International application No. PCT/RU2020/050080 International Search Report dated Nov. 5, 2020 with the translation.

International application No. PCT/RU2020/050080 Written Opinion of the International Searching Authority dated Nov. 5, 2020 with the translation.

International application No. PCT/RU2020/050080 International Preliminary Report on Patentability Chapter I dated Oct. 26, 2021.

Kadagidze Z.G. New approaches to the regulation of antitumor immunity (Новые, подходы, к, регуляции, противооп, ухолевого, иммунитета), Mammologia, 2007, No. 1, p. 10-12. Machine translation (Google machine translation) provided.

Biederbick K.D. et al., Efficacy of cytokine-induced killer cells targeting CD40 and GITR. Oncology Letters. Feb. 2019. vol. 17 Issue 2. Published online on: Dec. 18, 2018 https://doi.org/10.3892/pl.2018.9849. pp. 2425-2430.

Nocentini, et al. (1997). A new member of the tumor necrosis factor/nerve growth factor receptor family inhibits T cell receptor-induced apoptosis. Proc. Natl. Acad. Sci. 94:6216-6221.

Nocentini, et al. (2005). GITR: a multifaceted regulator of immunity belonging to the tumor necrosis factor receptor superfamily. E. J. Immunol. 35:1016-1022.

Chattopadhyay, et al. (2007). Assembly and structural properties of glucocorticoid-induced TNF receptor ligand: Implications for function. Proc. Natl. Acad. Sci. 104:19452-19457.

Zhou, et al. (2008). Human glucocorticoid-induced TNF receptor ligand regulates its signaling activity through multiple oligomerization states. Proc. Natl. Acad. Sci. 105:635-640.

Baltz, et al. (2008). Neutralization of tumor-derived soluble Glucocorticoid-Induced TNFR-Related Protein ligand Increases NK cell anti-tumor reactivity. Blood 112:3735-3743.

Mahesh, et al. (2006). Expression of GITR ligand abrogates immunosuppressive function of ocular tissue and differentially modulates inflammatory cytokines and chemokines. Eur. J. Immunol. 36: 2128-2138.

Agostini, et al. (2005). The Glucocorticoid-Induced Tumor Necrosis Factor Receptor-Related Gene Modulates the Response to Candida albicans Infection. Infect. Immun. 73:7502-7508.

Nocentini, et al. (2007). GITR/GITRL: More than an effector T cell co-stimulatory system. E. J. Immunol. 37:1165-1169.

Schaer, et al. (2012). Modulation of GITR for cancer immunotherapy. Current Opinion in Immunology. vol. 24, Issue 2, Apr. 2012, pp. 217-224.

Noof J., et al., Human antibody-Fc receptor interactions illuminated by crystal structures. Nat Rev Immunol 4, 2004, cc.89-99.

Bird et al. (1988). Single-Chain Antigen-Binding Proteins. Science 242:423-426.

Huston et al. (1988). Protein engineering of antibody binding sites: recovery of specific activity in an anti-digoxin single-chain Fv analogue produced in Escherichia coli. Proc. Natl. Acad. Sci. USA 85:5879-5883.

Burks et al., In vitro scanning saturation mutagenesis of an antibody binding pocket. Proc Natl Acad Sci USA, 94:412-117 (1997).

Wu et al., Stepwise in vitro affinity maturation of Vitaxin, an αvβ3-specific humanized mAb. Proc Natl Acad Sci USA 95:6037 6042 (1998).

Magdelaine-Beuzelin et al., Structure-function relationships of the variable domains of monoclonal antibodies approved for cancer treatment. Critical Reviews in Oncology/Hematology. vol. 64, Issue 3, Dec. 2007, pp. 210-225.

Lefranc et al., IMGT unique numbering for immunoglobulin and T cell receptor variable domains and Ig superfamily V-like domains. Dev. Comp Immunol. 27:55-77 (2003).

Sheets MD, et al. Efficient construction of a large nonimmune phage antibody library: the production of high-affinity human single-chain antibodies to protein antigens. Proc Natl Acad Sci U S A 1998,95:6157-6162.

De Haard HJ, et al. A large non-immunized human Fab fragment phage library that permits rapid isolation and kinetic analysis of high affinity antibodies. J Biol Chem 1999,274:18218-18230.

Vaughan TJ, et al. Human antibodies with sub-nanomolar affinities isolated from a large non-immunized phage display library. Nat Biotechnol 1996, 14:309-314.

Ulitin AB, et al. The library of human miniantibodies in the phage display format: Designing and testing. Dokl Biochem Biophys. Nov.-Dec. 2005;405:437-440.

Marks et al., By-passing immunization: Human antibodies from V-gene libraries displayed on phage. Journal of Molecular Biology. vol. 222, Issue 3, Dec. 5, 1991, pp. 581-597.

Smith GP: Filamentous fusion phage: novel expression vectors that display cloned antigens on the virion surface. Science 1985, 228:1315-1317.

Lonberg N, et al., Antigen-specific human antibodies from mice comprising four distinct genetic modifications. Nature 1994, 368:856-859.

Christoph A. Diebolder et al., Complement Is Activated by IgG Hexamers Assembled at the Cell Surface. Science. Mar. 14, 2014;343(6176):1260-1263.

(56) References Cited

OTHER PUBLICATIONS

Clynes et al., Fc receptors are required in passive and active immunity to melanoma. PNAS (USA) 95: 652-656 (1998).

Daëron, Fc Receptor Biology. Annu. Rev. Immunol. 15: 203-234 (1997).

Ravetch and Kinet, Fc Receptors. Annual Review of Immunology. vol. 9:457-492 (vol. publication date Apr. 1991).

Gazzano-Santoro et al., A non-radioactive complement-dependent cytotoxicity assay for anti-CD20 monoclonal antibody. Journal of Immunological Methods. vol. 202, Issue 2, Mar. 28, 1997, pp. 163-171.

Munson et al., Ligand: A versatile computerized approach for characterization of ligand-binding systems. Analytical Biochemistry. vol. 107, Issue 1, Sep. 1, 1980, pp. 220-239.

McCafferty et al., Phage antibodies: filamentous phage displaying antibody variable domains. Nature, 348, 1990, pp. 552-554.

Clackson et al., Making antibody fragments using phage display libraries. Nature, 352, 1991, pp. 624-628.

Marks et al., By-Passing Immunization: Building High Affinity Human Antibodies by Chain Shuffling. Bio/Technology vol. 10, pp. 779-783 (1992).

Waterhouse, et al., 1993. Combinatorial infection and in vivo recombination: a strategy for making large phage antibody repertoires. Nucleic Acid Research 21: 2265-2266.

Morrison, et al., Chimeric human antibody molecules: mouse antigen-binding domains with human constant region domains. Proc. Natl. Acad. Sci. USA: 81, 1984, p. 6851.

Carter et al., High Level *Escherichia coli* Expression and Production of a Bivalent Humanized Antibody Fragment. Bio/Technology, 10, 1992, pp. 163-167.

Edelman, G.M., et al., The Covalent Structure of an Entire γG Immunoglobulin Molecule. Proc. Natl. Acad. Sci. Natl. Acad. Sci. USA 63 (1969) 78-85.

Rajkumar Kunaparaju et al., Epi-CHO, an episomal expression system for recombinant protein production in CHO cells. Biotechnol Bioeng. vol. 91, Issue6. Sep. 20, 2005. pp. 670-677.

Xiangming Sun et al., Enhancement of transient gene expression by fed-batch culture of HEK 293 EBNA1 cells in suspension. Biotechnology Letters vol. 28, pp. 843-848 (2006).

Phuong Lan Pham et al., Large-scale transient transfection of serum-free suspension-growing HEK293 EBNA1 cells: Peptone additives improve cell growth and transfection efficiency. Biotechnol Bioeng. Nov. 5, 2003;84(3):332-342.

Sachdev S.Sidhu et al.,[21] Phage display for selection of novel binding peptides. Methods in Enzymology. vol. 328, 2000, pp. 333-363, IN5.

"UniProtKB-Q9Y5U5 (TNR18_HUMAN)," Protein: Tumor necrosis factor receptor superfamily member 18, Gene: TNFRSF18, Organism: *Homo sapiens* (Human), https://www.uniprot.org/uniprot/Q9Y5U5 (Retrieved Feb. 10, 2022).

"UniProtKB-Q1PBC4 (Q1PBC4_MACMU)," Protein: Submitted name—TNFSF18 protein, Gene: N/A, Organism, *Macaca mulatta* (Rhesus macaque), https://www.uniprot.org/uniprot/Q1PBC4 (Retrieved Feb. 10, 2022).

"UniProtKB-O35714 (TNR18_MOUSE)," Protein: Tumor necrosis factor receptor superfamily member 18, Gene: Tnfrsf18, Organism: *Mus* musculus (Mouse), https://www.uniprot.org/uniprot/O35714 (Retrieved Feb. 10, 2022).

"Human GITR/TNFRSF18 (NP_004186) VersaClone cDNA," https://www.mdsystems.com/products/human-gitr-infrsf18-np-004186-versaclone-cdna_rdc0359 (Retrieved Feb. 10, 2022).

"UniProtKB-Q9UNG2 (TNF18_HUMAN)," Protein: Tumor necrosis factor ligand superfamily member 18, Gene: TNFSF18, Organism: *Homo sapiens* (Human), https://www.uniprot.org/uniprot/Q9UNG2 (Retrieved Feb. 10, 2022).

Corresponding Canadian application No. 3,137,822 Office Action dated Apr. 8, 2024.

Corresponding European application No. 20794288.9 European search report dated Feb. 6, 2025.

Wei Li et al., Antibody Aggregation: Insights from Sequence and Structure. Antibodies, vol. 5, No. 3, Sep. 5, 2016, pp. 1-23. https://doi.org/10.3390/antib5030019.

\* cited by examiner

|  | BCD166-02-01 |
|---|---|
| FcRn, KD, M | 2.7 E-08 |
| FcγRIa, KD, M | 7.23E-10 |
| FcγRIIa-131H, KD, M | 7.22E-08 |
| FcγRIIa-131R, KD, M | 4.02E-08 |
| FcγRIIb, KD, M | 5.57E-07 |
| FcγRIIIa-158F, KD, M | 1.42E-06 |
| FcγRIIIa-158V, KD, M | 1.18E-07 |

Fig. 29

MONOCLONAL ANTIBODY THAT BINDS SPECIFICALLY TO GITR

REFERENCE TO A SEQUENCE LISTING SUBMITTED VIA EFS-WEB

The content of the ASCII text file of the sequence listing named "P2343US00 Sequence_EN_ANSI" which is 22.3 kb in size was created on Oct. 21, 2021 and electronically submitted herewith via EFS-Web is incorporated herein by reference.

FIELD OF INVENTION

The present invention relates to biotechnology, in particular to antibodies or antigen-binding fragments thereof, and to use thereof. More specifically, the present invention relates to monoclonal antibodies that specifically bind to GITR (Glucocorticoid-induced TNFR-related protein/TNFRSF18/tumor necrosis factor receptor superfamily, member 18). The invention also relates to a nucleic acid encoding said antibody or antigen-binding fragment thereof, an expression vector, a method for preparing said antibody, and use of said antibody in treatment of diseases or disorders associated with GITR.

BACKGROUND OF THE INVENTION

TNFRSF18, GITR (Glucocorticoid-induced TNFR-related protein/TNFRSF18/tumor necrosis factor receptor superfamily) is a membrane protein, a receptor belonging to tumor necrosis factor receptor superfamily.

GITR is a type I transmembrane protein consisting of 216 amino acids and having a molecular weight of 26 kDa. The N-terminal extracellular domain comprises three TNFR-Cys repeats and an N-glycosylation site. The three cysteine-rich domains and cytoplasmic tail of GITR share significant homology with 4-1BB, OX40 and CD27 (Nocentini, et al. (1997) Proc. Natl. Acad. Sci. 94:6216-6221).

Human GITR is expressed at low levels in responder T cells, with CD4+ cells exhibiting increased expression relative to CD8+ cells. GITR expression is significantly up-regulated for several days following T cell activation. GITR is constitutively expressed at high levels in regulatory T cells (Tregs), such as CD4+CD25+ or CD8+CD25+ cells, and is further up-regulated when these cells are activated (Nocentini and Riccardi (2005) E. J. Immunol. 35:1016).

However, GITR expression is not exclusively limited to T cells. Several works have also indicated that GITR is expressed on NK cells, macrophages, B cells, dendritic cells, mast cells and monocytes (Nocentini and Riccardi (2005) E. J. Immunol. 35:1016-1022).

GITR is expressed in lymph nodes, peripheral blood white blood cells and to a lesser extent in the spleen, constitutively expressed in high amounts on Tregs, in low amounts on naive T cells and memory cells.

However, GITR is expressed not only on immune cells, but also on tumor cells. RNA-Seq data analysis in relation to GITR expression in 33 tumor types has been conducted and has revealed that GITR is highly expressed in HNSCC (head and neck squamous cell carcinoma), NSCLC (non-small cell lung cancer), breast cancer, esophageal cancer and bladder cancer.

RNA-Seq analysis of samples from 24 tumor types has shown similar results. Thus, GITR is expressed not only on immune cells, but also on the membrane of tumor cells. In tumor samples, GITRL-Fc increased the gene expression associated with T cells, CD8 T cells, cytotoxicity, Th1 cells, interferon gamma, NK cells, Teff cells, and T cell activation markers.

Expression of GITR and ligand thereof is not restricted to haematopoietic cells. GITR is also expressed on keratinocytes, osteoclast precursors, whereas GITRL is expressed on endothelial cells.

GITRL is a type II transmembrane protein as is typical for most TNF ligand family members. Current research indicates that human GITRL typically exists as a trimer, although it can also be present as a monomer or assemble into other multimeric forms (Chattopadhyay, et al. (2007) Proc. Natl. Acad. Sci. 104:19452-19457; Zhou, et al. (2008) Proc. Natl. Acad. Sci. 105:635-640). There is some evidence suggesting that a soluble form of GITRL is also produced (Baltz, et al. (2008) Blood 112:3735-3743; Mahesh, et al. (2006) Eur. J. Immunol. 36: 2128-2138). GITRL is expressed primarily on antigen presenting cells (APC), including macrophages, B cells, dendritic cells and endothelial cells that can function as APC (Nocentini and Riccardi (2005) E. J. Immunol. 35:1016-1022; Agostini, et al. (2005) Infect. Immun. 73:7502-7508; and Nocentini, et al. (2007) E. J. Immunol. 37:11651169).

Binding of GITRL on APC to GITR on responder T cells triggers GITR signaling, which co-stimulates responder T cells and inhibits the suppressive activity of regulatory T cells. GITR signaling functions as a co-activating signal to both CD4+ and CD8+ naive T cells, thereby inducing or enhancing proliferation and effector function, particularly when T cell receptor (TCR) stimulation is close to optimal (Schaer, et al. (2012) Curr. Opin. Immunol. 24:217224). More specifically, GITR can have several effects on effector T cells and regulatory T cells, including: co-stimulation and activation of effector T cells such that they are more resistant to inhibition, inhibition of regulatory T cells, decreasing of the sensitivity of effector T cells to suppression by regulatory T cells and partial deletion of regulatory T cells from the circulation (Nocentini, et al. (2007) Eur. J. Immunol. 37:1165-1169).

The major functions of GITR, and thus the main effects of anti-GITR antibody, are to enhance proliferation and functioning of effector T cells, and to inhibit the suppressive effect of Tregs. Teff cells are generated initially devoid of the ability to resist inhibitory tumor microenvironment and suppression by Treg cells. Stimulation of GITR at secondary stages of priming and expansion, through agonist anti-GITR antibody, soluble GITR ligand or DC vaccine modulates both Teff and Treg tumor responses in favor of the former, thus promoting tumor regression. Thus, anti-GITR antibody provides Teff resistance to Treg suppression.

Collectively, the foregoing functions, in particular the costimualtion of responder T cells and abrogation of the suppressor activity of regulatory T cells, means that GITR activation results in an enhanced immune response. Such activation has the potential to restore immune responses to infections and to tumors. Accordingly, molecules capable of activating GITR would be of value as immunostimulatory agents under conditions when it is desirable to trigger an enhanced immune response.

The antibody must possess the properties of a GITR agonist, with effector, cytotoxic properties against Treg lymphocytes.

Various antibodies against GITR are known in the art (e.g. from WO2015187835, WO2015031667, WO2017068186, WO2017096189, WO2017214548).

23 anti-GITR agonists (antibodies/recombinant GITRLs) are now in preclinical and clinical trials. Only two antibodies are in Phase 2 clinical trials (TRX518, INCAGN1876), and AMG228, MEDI1873, MK-4166 are in Phase 1 clinical trials. Very few clinical data are presented.

However, at the moment, no antibody that specifically binds to GITR and that is approved for therapeutic use exists in the world.

In connection with the above, it is relevant to create novel agonistic antibodies, that interact with GITR, activate the receptor, abrogate the suppressor effect of regulatory T cells, inhibit/deplete the T-suppressor (regulatory) component of the immune system through ADCC effector properties.

BCD-166 is an agonist monoclonal antibody that interacts with GITR, activates the receptor, abrogates the suppressor effect of regulatory T cells, inhibits/deletes the T-suppressor (regulatory) component of the immune system through ADCC effector properties, thereby increasing the number of CD8+ and CD4+ effector cells and activating the T-effector component of the immune system in tumor microenvironment.

SUMMARY

In one aspect, the present invention relates to an isolated monoclonal antibody or antigen-binding fragment thereof that specifically binds to GITR comprising:
(a) a heavy chain variable domain comprising:
(i) CDR1 comprising an amino acid sequence selected from the group:

```
                                      (SEQ ID NO: 1)
        NYGMH
        or
                                      (SEQ ID NO: 12)
        YYWMY;
```

(ii) CDR2 comprising an amino acid sequence selected from the group:

```
                                      (SEQ ID NO: 2)
        VIWFDGSNKFYTDSVKG
        or
                                      (SEQ ID NO: 13)
        AISWNGGRTYYAESMKG;
```

(iii) CDR3 comprising an amino acid sequence selected from the group:

```
                                      (SEQ ID NO: 3)
        ELGGYYYDSSGFRPYYYGMDV
        or
                                      (SEQ ID NO: 14)
        NRYYSDPNYGMNL,
``` and
(b) a light chain variable domain comprising:
(i) CDR1 comprising an amino acid sequence selected from the group:

```
                                      (SEQ ID NO: 7)
        RASQSIGSWLA
        or
                                      (SEQ ID NO: 17)
        TGTSTDIGTYKYIS;
```

(ii) CDR2 comprising an amino acid sequence selected from the group:

```
                                      (SEQ ID NO: 8)
        AASTLQR
        or
                                      (SEQ ID NO: 18)
        GVSHRPS;
```

(iii) CDR3 comprising an amino acid sequence selected from the group:

```
                                      (SEQ ID NO: 9)
        QQSHSHPLT
        or
                                      (SEQ ID NO: 19)
        SSYTSSGTVV.
```

In some embodiments, a monoclonal antibody or antigen-binding fragment thereof comprises a heavy chain variable domain comprising CDR 1, 2 and 3 comprising amino acid sequences represented by the sequences of SEQ ID NOs: 1, 2 and 3, respectively.

In some embodiments, a monoclonal antibody or antigen-binding fragment thereof comprises a heavy chain variable domain comprising CDR 1, 2 and 3 comprising amino acid sequences represented by the sequences of SEQ ID NOs: 12, 13 and 14, respectively.

In some embodiments, a monoclonal antibody or antigen-binding fragment thereof comprises a light chain variable domain comprising CDR 1, 2 and 3 comprising amino acid sequences represented by SEQ ID NOs: 7, 8 and 9, respectively.

In some embodiments, a monoclonal antibody or antigen-binding fragment thereof comprises a light chain variable domain comprising CDR 1, 2 and 3 comprising amino acid sequences represented by SEQ ID NOs: 17, 18 and 19, respectively.

In some embodiments, a monoclonal antibody or antigen-binding fragment thereof comprises:
a heavy chain variable domain comprising CDRs 1, 2 and 3 comprising amino acid sequences represented by the sequences of SEQ ID NOs: 1, 2 and 3, respectively;
a light chain variable domain comprising CDRs 1, 2 and 3 comprising amino acid sequences represented by the sequences of SEQ ID NOs: 7, 8 and 9, respectively.

In some embodiments, a monoclonal antibody or antigen-binding fragment thereof comprises:
a heavy chain variable domain comprising CDRs 1, 2 and 3 comprising amino acid sequences represented by the sequences of SEQ ID NOs: 12, 13 and 14, respectively;
a light chain variable domain comprising CDRs 1, 2 and 3 comprising amino acid sequences represented by the sequences of SEQ ID NOs: 17, 18 and 19, respectively.

In some embodiments, a monoclonal antibody or antigen-binding fragment thereof comprises a heavy chain variable domain comprising an amino acid sequence that is at least 90% homologous to the amino acid sequence of SEQ ID NO: 4.

In some embodiments, a monoclonal antibody or antigen-binding fragment thereof comprises a heavy chain variable domain comprising the amino acid sequence of SEQ ID NO: 4.

In some embodiments, a monoclonal antibody or antigen-binding fragment thereof comprises a heavy chain variable domain comprising an amino acid sequence that is at least 90% homologous to the amino acid sequence of SEQ ID NO: 15.

In some embodiments, a monoclonal antibody or antigen-binding fragment thereof comprises a heavy chain variable domain comprising the amino acid sequence of SEQ ID NO: 15.

In some embodiments, a monoclonal antibody or antigen-binding fragment thereof comprises a light chain variable domain comprising an amino acid sequence that is at least 90% homologous to the amino acid sequence of SEQ ID NO: 10.

In some embodiments, a monoclonal antibody or antigen-binding fragment thereof comprises a light chain variable domain comprising the amino acid sequence of SEQ ID NO: 10.

In some embodiments, a monoclonal antibody or antigen-binding fragment thereof comprises a light chain variable domain comprising an amino acid sequence that is at least 90% homologous to the amino acid sequence of SEQ ID NO: 20.

In some embodiments, a monoclonal antibody or antigen-binding fragment thereof comprises a light chain variable domain comprising the amino acid sequence of SEQ ID NO: 20.

In some embodiments, a monoclonal antibody or antigen-binding fragment thereof comprises:
- a heavy chain variable domain comprising an amino acid sequence that is at least 90% homologous to the amino acid sequence of SEQ ID NO: 4;
- a light chain variable domain comprising an amino acid sequence that is at least 90% homologous to the amino acid sequence of SEQ ID NO: 10.

In some embodiments, a monoclonal antibody or antigen-binding fragment thereof comprises:
- a heavy chain variable domain comprising the amino acid sequence of SEQ ID NO: 4;
- a light chain variable domain comprising the amino acid sequence of SEQ ID NO: 10.

In some embodiments, a monoclonal antibody or antigen-binding fragment thereof comprises:
- a heavy chain variable domain comprising an amino acid sequence that is at least 90% homologous to the amino acid sequence of SEQ ID NO: 15;
- a light chain variable domain comprising an amino acid sequence that is at least 90% homologous to the amino acid sequence of SEQ ID NO: 20.

In some embodiments, a monoclonal antibody or antigen-binding fragment thereof comprises:
- a heavy chain variable domain comprising the amino acid sequence of SEQ ID NO: 15;
- a light chain variable domain comprising the amino acid sequence of SEQ ID NO: 20.

In some embodiments, a monoclonal antibody that specifically binds to GITR is a full-length IgG antibody.

In some embodiments, the monoclonal IgG antibody is of human IgG1, IgG2, IgG3 or IgG4 isotype.

In some embodiments, the monoclonal IgG antibody is of human IgG1 isotype.

In some embodiments, a monoclonal antibody that specifically binds to GITR comprises the E358R mutation in the Fc fragment to increase agonist properties, antibody-dependent cellular cytotoxicity (ADCC), but not complement-dependent cytotoxicity (CDC).

In some embodiments, a monoclonal antibody comprises a heavy chain comprising an amino acid sequence that is at least 90% homologous to the sequence of SEQ ID NO: 5.

In some embodiments, a monoclonal antibody comprises a heavy chain comprising the amino acid sequence of SEQ ID NO: 5.

In some embodiments, a monoclonal antibody comprises a heavy chain comprising an amino acid sequence that is at least 90% homologous to the sequence of SEQ ID NO: 6.

In some embodiments, a monoclonal antibody comprises a heavy chain comprising the amino acid sequence of SEQ ID NO: 6.

In some embodiments, a monoclonal antibody comprises a light chain comprising an amino acid sequence that is at least 90% homologous to the sequence of SEQ ID NO: 11.

In some embodiments, a monoclonal antibody comprises a light chain comprising the amino acid sequence of SEQ ID NO: 11.

In some embodiments, a monoclonal antibody comprises:
- a heavy chain comprising an amino acid sequence that is at least 90% homologous to the sequence of SEQ ID NO: 5;
- a light chain comprising an amino acid sequence that is at least 90% homologous to the sequence of SEQ ID NO: 11.

In some embodiments, a monoclonal antibody comprises:
- a heavy chain comprising the amino acid sequence of SEQ ID NO: 5;
- a light chain comprising the amino acid sequence of SEQ ID NO: 11.

In some embodiments, a monoclonal antibody comprises:
- a heavy chain comprising an amino acid sequence that is at least 90% homologous to the sequence of SEQ ID NO: 6;
- a light chain comprising an amino acid sequence that is at least 90% homologous to the sequence of SEQ ID NO: 11.

In some embodiments, a monoclonal antibody comprises:
- a heavy chain comprising the amino acid sequence of SEQ ID NO: 6;
- a light chain comprising the amino acid sequence of SEQ ID NO: 11.

In some embodiments, a monoclonal antibody comprises a heavy chain comprising an amino acid sequence that is at least 90% homologous to the sequence of SEQ ID NO: 16.

In some embodiments, a monoclonal antibody comprises a heavy chain comprising the amino acid sequence of SEQ ID NO: 16.

In some embodiments, a monoclonal antibody comprises a light chain comprising an amino acid sequence that is at least 90% homologous to the sequence of SEQ ID NO: 21.

In some embodiments, a monoclonal antibody comprises a light chain comprising the amino acid sequence of SEQ ID NO: 21.

In some embodiments, a monoclonal antibody comprises:
- a heavy chain comprising an amino acid sequence that is at least 90% homologous to the sequence of SEQ ID NO: 16;
- a light chain comprising an amino acid sequence that is at least 90% homologous to the sequence of SEQ ID NO: 21.

In some embodiments, a monoclonal antibody comprises:
- a heavy chain comprising the amino acid sequence of SEQ ID NO: 16;
- a light chain comprising the amino acid sequence of SEQ ID NO: 21.

In one aspect, the present invention relates to an isolated nucleic acid that encodes any said antibody or antigen-binding fragment thereof.

In some embodiments, a nucleic acid is DNA.

In one aspect, the present invention relates to an expression vector comprising the above nucleic acid.

In one aspect, the present invention relates to a method for obtaining a host cell to produce said antibody or antigen-binding fragment thereof, which comprises transformation of a cell with said vector.

In one aspect, the present invention relates to a host cell for preparing said antibody or antigen-binding fragment thereof comprising said nucleic acid.

In one aspect, the present invention relates to a method for obtaining said antibody or antigen-binding fragment thereof, comprising culturing said host cell in a culture medium under conditions sufficient to produce said antibody, if necessary, followed by isolation and purification of the obtained antibody.

In one aspect, the present invention relates to a pharmaceutical composition used for treating a disease or disorder mediated by GITR comprising said antibody or antigen-binding fragment thereof in a therapeutically effective amount in combination with one or more pharmaceutically acceptable excipients.

In some embodiments, a pharmaceutical composition is intended to be used for treating a disease or disorder mediated by GITR selected from the group comprising: cervical cancer, head and neck cancer, stomach cancer, breast cancer, renal cell cancer, CRC (colorectal cancer), (OC) ovarian cancer, NSCLC (non-small cell lung cancer).

In one aspect, the present invention relates to a pharmaceutical composition for treating a disease or disorder mediated by GITR comprising said antibody or antigen-binding fragment thereof in a therapeutically effective amount and at least one therapeutically active antitumour compound in a therapeutically effective amount.

In some embodiments, a pharmaceutical composition is intended to be used for treating a disease or disorder mediated by GITR selected from the group comprising cervical cancer, head and neck cancer, stomach cancer, breast cancer, renal cell cancer, CRC (colorectal cancer), (OC) ovarian cancer, NSCLC (non-small cell lung cancer).

In some embodiments, a pharmaceutical composition comprises a therapeutically active antitumour compound selected from a chemotherapeutic agent, antibody or anti-hormonal agent.

In some embodiments, a pharmaceutical composition comprises a therapeutically active antitumour compound that is an antibody selected from the group comprising: anti-PD1 antibodies, anti-PD-L1 antibodies, anti-CTLA4 antibodies, anti-4-1BB antibodies, anti-OX40 antibodies or combinations thereof.

In some embodiments, a pharmaceutical composition comprises a therapeutically active antitumour compound that is a small molecule.

In some embodiments, a pharmaceutical composition comprises a therapeutically active antitumour compound selected from the group of activators of innate or adaptive immunity.

In some embodiments of a pharmaceutical composition, said antibody and at least one therapeutically active antitumour compound are administered sequentially.

In some embodiments of a pharmaceutical composition, said antibody and at least one therapeutically active antitumour compound are administered simultaneously.

In one aspect, the present invention relates to a method for inhibiting the biological activity of GITR in a subject in need of such inhibition, comprising administering an effective amount of said antibody or antigen-binding fragment thereof.

In one aspect, the present invention relates to a method for treatment of a disease or disorder mediated by GITR comprising administering to a subject in need of such treatment said antibody or antigen-binding fragment thereof or said pharmaceutical composition, in a therapeutically effective amount.

In some embodiments, a method for treatment includes a disease or disorder selected from the group comprising: cervical cancer, head and neck cancer, stomach cancer, breast cancer, renal cell cancer, CRC (colorectal cancer), (OC) ovarian cancer, NSCLC (non-small cell lung cancer).

In one aspect, the present invention relates to the use of said antibody or antigen-binding fragment thereof or said pharmaceutical composition for treatment in a subject in need of such treatment of a disease or disorder mediated by GITR.

In some embodiments, the use includes a disease or disorder selected from the group: cervical cancer, head and neck cancer, stomach cancer, breast cancer, renal cell cancer, CRC (colorectal cancer), (OC) ovarian cancer, NSCLC (non-small cell lung cancer).

BRIEF DESCRIPTION OF DRAWINGS

FIG. 29. Table of data for binding affinity constants of BCD166-02-01 candidate to gamma receptors.

DESCRIPTION OF THE INVENTION

Definitions and General Methods

Figure 1:
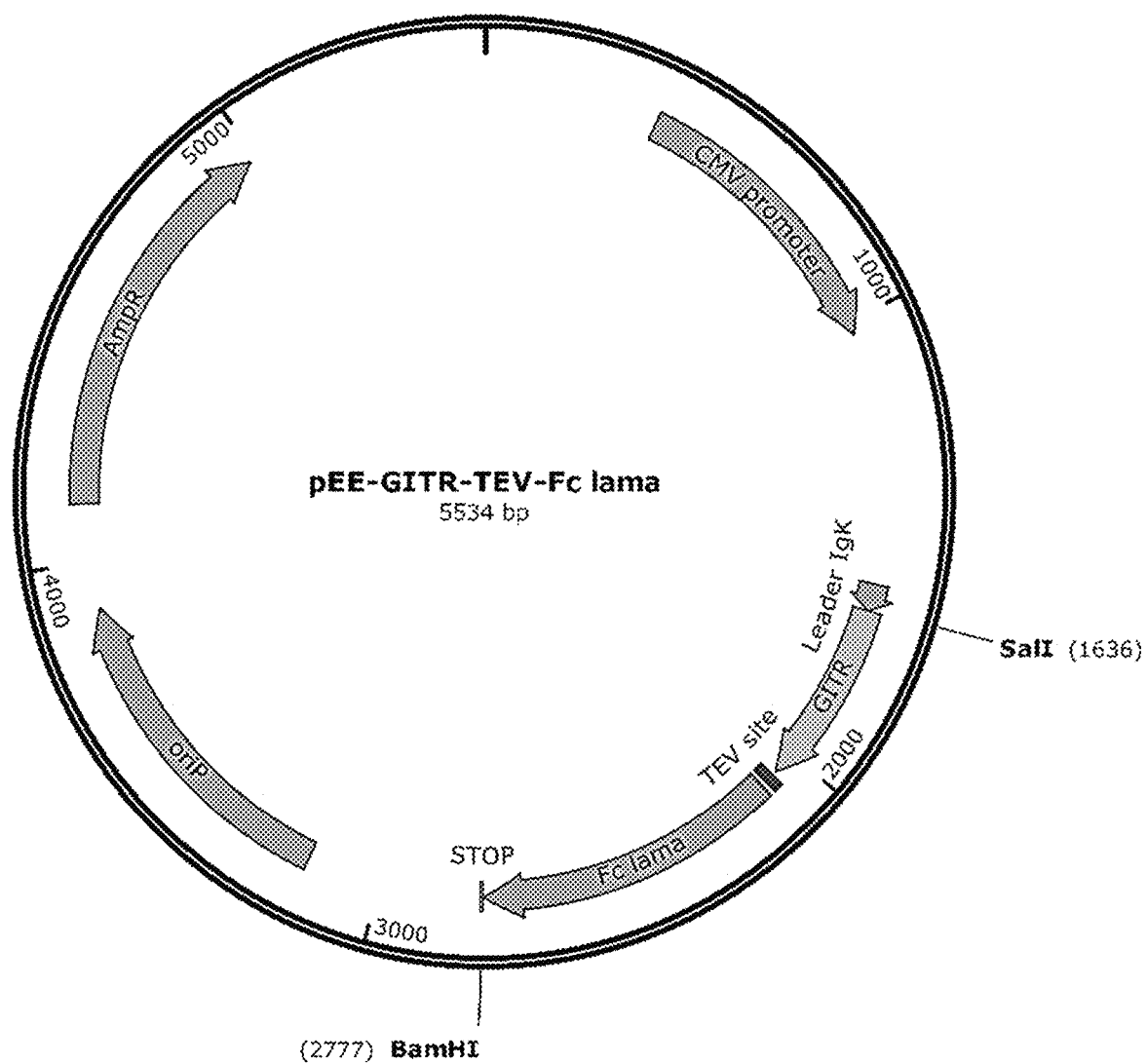
FIG. 1. Plasmid for protein production pEE-GITR-TEV-Fc lama.

Unless defined otherwise, all technical and scientific terms used herein have the same meaning as is commonly understood by one of ordinary skill in the art.

Further, unless otherwise required by context, singular terms shall include pluralities and plural terms shall include the singular. Typically, the classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's instructions, as is common in the art, or as described herein.

Definitions Associated with the Antibody

TNFRSF18, GITR (Glucocorticoid-induced TNFR-related protein/TNFRSF18/tumor necrosis factor receptor superfamily) is a membrane protein, a receptor belonging to tumor necrosis factor receptor superfamily. GITR is a type I transmembrane protein consisting of 216 amino acids and having a molecular weight of 26 kDa. The N-terminal extracellular domain comprises three TNFR-Cys repeats and an N-glycosylation site. The three cysteine-rich domains and cytoplasmic tail of GITR share significant homology with 4-1BB, OX40 and CD27 (Nocentini, et al. (1997) Proc. Natl. Acad. Sci. 94:6216-6221).

Amplification of the GITR gene and/or overexpression of protein thereof were found in many cancer diseases, including: cervical cancer, head and neck cancer, stomach cancer, breast cancer, renal cell cancer, CRC (colorectal cancer), (OC) ovarian cancer, NSCLC (non-small cell lung cancer).

The term "binding molecule" includes antibodies and immunoglobulins.

The term "antibody" or "immunoglobulin" (Ig), as used in this description, includes whole antibodies and any antigen binding fragment (i.e., "antigen-binding portion") or single chains thereof. The term "antibody" refers to a glycoprotein comprising at least two heavy (H) chains and two light (L) chains interconnected by disulfide bonds, or an antigen-binding portion. Each heavy chain comprises a heavy chain variable region (abbreviated referred to herein as VH) and a heavy chain constant region. Known are five types of mammalian Ig heavy chain denoted by Greek letters: α, δ, ε, γ and μ. The type of a heavy chain present defines the class of an antibody; these chains are found in IgA, IgD, IgE, IgG, and IgM antibodies, respectively. Distinct heavy chains differ in size and composition; α and γ contain approximately 450 amino acids, while μ and ε have approximately 550 amino acids. Each heavy chain has two regions, the constant region and the variable region. The constant region is identical in all antibodies of the same isotype, but differs in antibodies of different isotypes. Heavy chains γ, α and δ have a constant region composed of three constant domains CH1, CH2 and CH3 (in a line), and a hinge region for added flexibility (Woof J., Burton D., Nat Rev Immunol 4, 2004, cc. 89-99); heavy chains μ and ε have a constant region composed of four constant domains CH1, CH2, CH3 and CH4. In mammals, known are only two types of light chain denoted by lambda (λ) and kappa (κ). Each light chain consists of a light chain variable region (abbreviated referred to herein as VL) and light chain constant region. The approximate length of a light chain is 211 to 217 amino acids. Preferably, the light chain is a kappa (κ) light chain, and the constant domain CL is preferably C kappa (κ).

"Antibodies" according to the invention can be of any class (e.g. IgA, IgD, IgE, IgG, and IgM, preferably IgG), or subclass (e.g. IgG1, IgG2, IgG3, IgG4, IgA1 and IgA2, preferably IgG1).

VL and VH regions can be further subdivided into hypervariability regions called complementarity determining regions (CDRs), interspersed between regions that are more conserved, termed framework regions (FR). Each VH and VL is composed of three CDR and four FR, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

The term "antigen-binding portion" of an antibody or "antigen-binding fragment" (or simply "antibody portion" or "antibody fragment"), as used herein, refers to one or more fragments of an antibody that retain the ability to specifically bind to an antigen. It has been shown that the antigen-binding function of an antibody can be performed by fragments of a full length antibody. Examples of binding fragments which are included within the term "antigen-binding portion" of an antibody include (i) Fab-fragment monovalent fragment consisting of the VL, VH, CL and CH 1 domains; (ii) F(ab') 2 fragment, a bivalent fragment comprising two Fab-fragments linked by a disulfide bridge at the hinge region; (iii) Fd-fragment consisting of the VH and CH1 domains; (iv) Fv-fragment consisting of the VL and VH domains of a single arm of an antibody; (v) dAb-fragment (Ward et al., (1989) Nature 341:544-546), which consists of a VH/VHH domain; and (vi) extracted complementarity determining region (CDR). In addition, two regions of the Fv-fragment, VL and VH, are encoded by separate genes, they can be joined using recombinant methods using a synthetic linker that enables them to receive a single protein chain in which the VL and VH region are paired to form monovalent molecules (known as single chain Fv (scFv); see e.g. Bird et al. (1988) Science 242:423-426; and Huston et al. (1988) Proc. Natl. Acad. Sci. USA 85:5879-5883). It is assumed that such single-stranded molecules are also included within the term "antigen-binding portion" of an antibody. Such antibody fragments are obtained using conventional techniques known to those skilled in the art, and the fragments are screened in the same manner as are intact antibodies.

Preferably, the CDR of antigen-binding portion or the whole antibody antigen binding portion of the invention is derived from mouse, lama or human donor library or substantially of human origin with certain amino acid residues altered, e.g. substituted with different amino acid residues in order to optimize the properties of the specific antibodies, e.g. KD, koff, IC50, EC50, ED50. Preferably the framework regions of antibodies of the invention are of human origin or substantially of human origin (at least 80, 85, 90, 95, 96, 97, 98 or 99% of human origin).

In other embodiments, the antigen binding portion of the invention may be derived from other non-human species including mouse, lama, rabbit, rat or hamster, but not limited to. Alternatively, the antigen-binding region can be derived from the human species.

The term "variable" refers to the fact that certain portions of the variable domains greatly differ in sequence among antibodies. The V domain mediates antigen binding and determines specificity of each particular antibody for its particular antigen. However, the variability is not evenly distributed across the 110-amino acid span of the variable domains. Instead, the V regions consist of invariant fragments called framework regions (FRs) of 15-30 amino acids separated by shorter regions of extreme variability called "hypervariable regions" or CDR. Each variable domain of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies. The constant domains are not involved directly in binding an antibody to an antigen, but exhibit various effector functions, such as participation of the antibody in antibody-dependent cellular cytotoxicity (ADCC).

The term "hypervariable region" according to this description refers to the amino acid residues of an antibody which are responsible for antigen binding. Typically, the hypervariable region generally comprises amino acid residues from a "complementarity determining region" or "CDR" and/or those residues from a "hypervariable loop".

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., Proc Natl Acad Sci USA, 94:412-417 (1997) and the stepwise in vitro affinity maturation method by Wu et al., Proc Natl Acad Sci USA 95:6037 6042 (1998).

"Framework regions" (FR) are those variable domain residues other than the CDR residues. Each variable domain typically has four FRs identified as FR1, FR2, FR3 and FR4. If the CDRs are defined according to Kabat, the light chain FR residues are positioned about at residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

The fragment crystallizable region ("Fc region, Fc") of an immunoglobulin is the "tail" region of an immunoglobulin molecule that interacts with cell surface Fc-receptor, as well as some proteins of the complement system. This property allows antibodies to activate the immune system. In IgG, IgA and IgD antibody isotypes, the Fc region is composed of two identical protein fragments, respectively, from the second and third constant domains of the two heavy chains; in IgM and IgE isotypes, the Fc region contains three heavy chain constant domains (CH domains 2-4) in each polypeptide chain.

An antibody of the present invention "which binds" a target antigen refers to an antibody capable of binding the antigen with sufficient affinity such that the antibody can be used as a diagnostic and/or therapeutic agent targeting a protein or cell expressing said antigen, and slightly cross-reacts with other proteins. According to analytical methods: fluorescence-activated cell sorting (FACS), radioimmunoassay (RIA) or ELISA, in such embodiments, the degree of antibody binding to a non-target protein is less than 10% of antibody binding to a specific target protein. With regard to the binding of an antibody to a target molecule, the term "specific binding" or "specifically binds to" or is "specific for" a particular polypeptide or an epitope on a particular polypeptide target means binding that is noticeably (measurably) different from a non-specific interaction (for example, in the case of bH1-44 or bH1-81, a non-specific interaction is binding to bovine serum albumin, casein, fetal bovine serum or neutravidin).

Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. As used herein, the term "specific binding" or "specifically binds to" or is "specific for" a particular polypeptide or an epitope on a particular polypeptide target can be described by a molecule having a Kd for the target of at least about 200 nM, or at least about 150 nM, or at least about 100 nM, or at least about 60 nM, or at least about 50 nM, or at least about 40 nM, or at least about 30 nM, or at least about 20 nM, or at least about 10 nM, or at least about 8 nM, or at least about 6 nM, or at least about 4 nM, or at least about 2 nM, or at least about 1 nM, or greater. In one embodiment, the term "specific binding" refers to binding where a molecule binds to a particular polypeptide or epitope on a particular polypeptide without substantially binding to any other polypeptide or polypeptide epitope.

The term "Ka" as used herein refers to the association (on) rate of a particular antibody-antigen interaction.

The term "Kd" as used herein refers to the dissociation (off) rate of a particular antibody-antigen interaction.

"Binding affinity" generally refers to the strength of the sum total of noncovalent interactions between a single binding site of a molecule (e.g. an antibody) and its binding partner (e.g. an antigen). Unless indicated otherwise, "binding affinity" refers to intrinsic (characteristic, true) binding affinity which reflects a 1:1 interaction between members of a binding pair (e.g. antibody and antigen). The affinity of a molecule X for its binding partner Y can generally be represented by the dissociation constant (Kd). The preferred Kd value is about 200 nM, 150 nM, 100 nM, 60 nM, 50 nM, 40 nM, 30 nM, 20 nM, 10 nM, 8 nM, 6 nM, 4 nM, 2 nM, 1 nM, or less. Affinity can be measured by common methods known in the art, including those described herein. Low-affinity antibodies are usually slow to bind to the antigen and tend to dissociate easily, whereas high-affinity antibodies are usually faster at binding the antigen and tend to stay longer in the bound state. A variety of methods of measuring binding affinity are known in the art, any of which can be used for the purposes of the present invention.

In one embodiment, "Kd" or "Kd value" is measured by using surface plasmon resonance assays using BIAcore™-2000 or BIAcore®-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. Antigen is diluted with 10 mM sodium acetate, pH 4.8, into 5 µg/ml (~0.2 µM) and then injected at a flow rate of 5 µl/minute to achieve approximately 10 response units (RU) of coupled protein. Following the injection of antigen, 1M ethanolamine solution is injected to block unreacted groups. For kinetics measurements, two-fold serial dilutions of Fab (e.g. 0.78 nM to 500 nM) are injected in PBS with 0.05% Tween® 20 (PBST) at 25° C. at a flow rate of approximately 25 µl/min. On-rates (kon) and off-rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g. Chen, Y., et al., (1999) J. Mol. Biol. 293: 865-881. If the on rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody solution (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The term "koff" refers to the off rate constant of a particular interaction between a binding molecule and antigen. The off rate constant koff can be measured using bio-layer interferometry, for example, using Octet™ system.

"On-rate" or "kon" according to the present invention can be also measured by using the above surface plasmon resonance assays using BIAcore™-2000 or BIAcore®-3000 (BIAcore, Inc., Piscataway, N.J.) at 25° C. with immobilized antigen CM5 chips at ~10 relative units (response units, RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the manufacturer's instructions. Antigen is diluted with 10 mM sodium acetate, pH 4.8, into 5 μg/ml (~0.2 μM) and then injected at a flow rate of 5 μl/minute to achieve approximately 10 response units (RU) of coupled protein. Following the injection of antigen, 1M ethanolamine solution is injected to block unreacted groups.

Unless specified otherwise, the term "biologically active" and "biological activity" and "biological characteristics" with respect to a polypeptide of the invention means having the ability to bind to a biological molecule.

The term "biological molecule" refers to a nucleic acid, a protein, a carbohydrate, a lipid, and combinations thereof. In one embodiment, the biological molecule exists in nature.

Antibody fragments, such as Fab and F(ab')2 fragments, can be prepared from whole antibodies using conventional techniques, such as papain or pepsin digestion of whole antibodies. Moreover, antibodies, portions thereof and immunoadhesion molecules can be prepared using standard recombinant DNA techniques, for example, as described herein.

The term "recombinant antibody" is intended to refer to an antibody that is expressed in a cell or cell line comprising nucleotide sequence(s) encoding antibodies, wherein said nucleotide sequence(s) is not naturally associated with the cell.

As used herein, the term "variant antibody" is intended to refer to an antibody which has an amino acid sequence which differs from the amino acid sequence of a "parental" antibody thereof by virtue of adding, deleting and/or substituting one or more amino acid residues as compared to the sequence of a parental antibody. In a preferred embodiment, a variant antibody comprises at least one or more (e.g. one to twelve, e.g. two, three, four, five, six, seven, eight or nine, ten, eleven or twelve; in some embodiments, a variant antibody comprises from one to about ten) additions, deletions, and/or substitutions of amino acids as compared to a parental antibody. In some embodiments, such additions, deletions and/or substitutions are made in the CDRs of a variant antibody. Identity or homology with respect to the sequence of a variant antibody is defined herein as the percentage of amino acid residues in the variant antibody sequence that are identical to the parental antibody residues, after aligning the sequences and introducing gaps, if necessary, to achieve the maximum percent of sequence identity. A variant antibody retains the ability to bind to the same antigen, and preferably to an epitope, to which the parental antibody binds; and in some embodiments, at least one property or biological activity are superior to those of a parental antibody. For example, a variant antibody may have, e.g. a stronger binding affinity, longer half-life, lower IC50 value, or enhanced ability to inhibit antigen biological activity as compared to a parental antibody. The variant antibody of particular interest herein is one which displays at least 2 times, (preferably at least 5 times, 10 times or 20 times) enhancement in biological activity as compared to a parental antibody.

The term "bispecific antibody" refers to an antibody having an antigen-binding domain(s) that are capable of specific binding to two distinct epitopes on a single biological molecule or capable of specific binding to epitopes on two distinct biological molecules. The bispecific antibody is also referred to herein as having "dual specificity" or as being a "dual specificity" antibody.

In a broad sense, the term "chimeric antibody" is intended to refer to an antibody that comprises one or more regions of one antibody, and one or more regions of one or several other antibodies, typically, a partially human and partially non-human antibody, i.e. derived partially from a non-human animal, such as mice, rats, or the like vermin, or the Camelidae such as llama and alpaca. Chimeric antibodies are generally preferred over non-human antibodies in order to reduce the risk of a human anti-antibody immune response, e.g. a human anti-mouse antibody immune response in the case of a murine antibody. An example of a typical chimeric antibody is one in which the variable region sequences are murine sequences, while the constant region sequences are human. In the case of a chimeric antibody, the non-human portions may be subjected to further alteration in order to humanize the antibody.

The term "humanization" is intended to refer to the fact that when an antibody has a fully or partially non-human origin, for example, a mouse or llama antibody obtained by immunizing mice or lamas, respectively, with an antigen of interest, or is a chimeric antibody based on such an antibody of a mouse or llama, it is possible to substitute certain amino acids, in particular in the framework regions and constant domains of heavy and light chains, in order to avoid or minimize the immune response in humans. The specificity of the interaction of the antibody with the target antigen is inherent mainly in amino acid residues located in the six CDR regions of the heavy and light chain. For this reason, amino acid sequences within CDRs are far more variable between individual antibodies than those outside of CDRs. Because CDR sequences are responsible for most antibody-antigen interactions, it is possible to express recombinant antibodies that mimic the properties of a specific naturally occurring antibody, or more generally, of any specific antibody with said amino acid sequence, e.g. by constructing expression vectors that express CDR sequences from the specific antibody and framework sequences from a different antibody. As a result, it is possible to "humanize" a non-human antibody and, to a large extent, preserve binding specificity and affinity of the initial antibody. Although it is not possible to precisely predict the immunogenicity and thereby the human anti-antibody response of a particular antibody, non-human antibodies are typically more immunogenic than human antibodies. Chimeric antibodies, where the foreign (e.g. vermin or Camelidae) constant regions have been substituted with sequences of human origin, have shown to be generally less immunogenic than those of fully foreign origin, and the trend in therapeutic antibodies is towards humanized or fully human antibodies. Therefore, chimeric antibodies or other antibodies of non-human origin can be humanized to reduce the risk of a human anti-antibody response.

For chimeric antibodies, humanization typically involves modification of the framework regions of variable region sequences. Amino acid residues that are part of complementarity determining regions (CDRs) will be most often not modified by virtue of humanization, although in some cases it may be desirable in order to modify individual amino acid residues of a CDR, for example, in order to delete a glycosylation site, deamidation site, aspartate isomerization site, or undesired cysteine or methionine residues. N-linked glycosylation is made by virtue of attaching an oligosaccharide chain to an asparagine residue in a tripeptide sequence Asn-X-Ser or Asn-X-Thr, where X can be any amino acid except Pro. Removal of an N-glycosylation site may be achieved by mutating either the Asn or Ser/Thr residue by a different residue, preferably by way of conservative substitution. Deamidation of asparagine and glutamine residues can occur depending on such factors as pH and surface exposure. Asparagine residues are especially susceptible to deamidation, primarily when present in sequence Asn-Gly, and in a lesser degree in other dipeptide sequences such as Asn-Ala. Provided a CDR sequence comprises such a deamidation site, in particular Asn-Gly, it may be desirable to remove this site, typically by virtue of conservative substitution to delete one of the implicated residues.

Numerous methods for humanization of an antibody sequence are known in the art. One commonly used method is CDR grafting. CDR grafting may be based on the CDR definitions by Kabat, although the last edition (Magdelaine-Beuzelin et al., Crit Rev. Oncol Hematol. 64:210 225 (2007)) suggests that the IMGT® (the international ImMunoGeneTics Information System®) definition may improve humanization results (see Lefranc et al., Dev. Comp Immunol. 27:55-77 (2003)). In some cases, CDR grafting may reduce the binding specificity and affinity, and thus the biological activity, of a CDR grafted non-human antibody, as compared to a parental antibody from which the CDRs were obtained. Back mutations (which are sometimes referred to as "framework region repair") may be introduced at selected positions of a CDR grafted antibody, typically in framework regions, in order to restore the binding specificity and affinity of a parental antibody. Identification of positions for possible back mutations can be performed using information available in the literature and in antibody databases. Amino acid residues that are candidates for back mutations are typically those that are located at the surface of an antibody molecule, whereas residues that are buried or that have a low degree of surface exposure will not normally be altered. An alternative humanization technique to CDR grafting and back mutation is resurfacing, in which non-surface exposed residues of non-human origin are retained, whereas surface residues are altered to human residues.

Fully human antibodies can be generated using two techniques: using in vitro collected phage libraries or in vivo immunization of humanized animals (mice, rats, etc.).

Construction of combinatorial phage antibody libraries begins with selection of a source of gene repertoire, depending on which several antibody library types can be distinguished: naive, immune and synthetic. Naive and immune libraries are constructed using naturally reorganized genes, which encode the variable immunoglobulin domains of healthy donors or donors immunized with a certain antigen, respectively. MRNA from the antibody-producing lymphoid cell line is isolated for this purpose. Peripheral blood lymphocytes are mainly used, but in some cases splenocytes have been used as well [Sheets M D, Amersdorfer P. Finnern R, Sargent P, Lindquist E, Schier R, et al. Efficient construction of a large nonimmune phage antibody library: the production of high-affinity human single-chain antibodies to protein antigens. Proc Natl Acad Sci USA 1998, 95:6157-6162 and de Haard H J, van Neer N, Reurs A, Hufton S E, Roovers R C, Henderikx P. et al. A large non-immunized human Fab fragment phage library that permits rapid isolation and kinetic analysis of high affinity antibodies. J Biol Chem 1999, 274:18218-18230.], tonsillar cells or bone marrow lymphocytes [Vaughan T J, Williams A J, Pritchard K, Osbourn J K, Pope A R, Earnshaw J C, et al. Human antibodies with sub-nanomolar affinities isolated from a large non-immunized phage display library. Nat Biotechnol 1996, 14:309-314.]. cDNA is then synthesized on the base of mRNA, and both oligo-dT primers and statistically devised hexanucleotides can be used that yield cDNA copies of all the possible variants of genes encoding the variable domains of antibodies [Ulitin A B, Kapralova M V, Laman A G, Shepelyakovskaya A O, Bulgakova E B, Fursova K K, et al. The library of human miniantibodies in the phage display format: Designing and testing DAN: Izd-vo "Nauka"; 2005.].

One or several primers can be simultaneously used to limit the range of amplified genes to one or several variable domain gene families or antibody isotypes, now at cDNA level [Marks J D, Hoogenboom H R, Bonnert T P, McCafferty J, Griffiths A D, Winter G. Bypassing immunization. Human antibodies from V-gene libraries displayed on phage. J Mol Biol 1991, 222:581-597]. The primers used for amplification of genes encoding immunoglobulins are complementary to their most conservative regions. Their sequences are selected from gene collections that are organized into databases, such as Kabat or V BASE databases. The primer design also provides for internal restriction sites for cloning the PCR-products into the appropriate vectors.

Construction of synthetic libraries is based on replacement of natural CDRs with a set of random sequences. In this case, it is possible to generate a vast variety of antigen-binding sites.

Phage display is one of the most powerful and widely used in vitro technique for search for antibodies. In 1985, Smith found that foreign DNA sequences could be cloned into filamentous bacteriophage M13 and that such cloned sequence can be expressed on the surface of phage particles as fusion proteins (Smith G P: Filamentous fusion phage: novel expression vectors that display cloned antigens on the virion surface. Science 1985, 228:1315-1317). Thus, it is possible to select the fusion proteins of interest based on their ability to bind other proteins. This discovery was combined with PCR amplification methods, which made it possible to clone the cDNA repertoire of immunoglobulin genes to create a variety of phage libraries containing variable domains that can be used to quickly search for target-specific monoclonal antibodies. Phage library repertoire reflects that of B-cell antibody of any human or animal whose blood was used to create the library. In 1995, two papers described the production of genetically engineered mice which were capable of expression of fully human antibodies, the repertoires of which are comparable to those obtained by the hybridoma technology (Lonberg N, Taylor L D, Harding F A, Trounstine M, Higgins K M, Schramm S R, Kuo C C, Mashayekh R, Wymore K, McCabe J G et al.: Antigen-specific human antibodies from mice comprising four distinct genetic modifications. Nature 1994, 368:856-859). In these animals, their own endogenous heavy and k light immunoglobulin chain genes were deliberately destroyed, followed by introduction of transgenes, which are the segments of human heavy and k light chain genes. It turned out that human gene repertoire can be used by the mouse immune system to produce high specificity and high affinity antibodies against a greater variety of antigens. Despite the fact that transgenic mice express B-cell receptors that are essentially hybrids of mouse and human components (human immunoglobulin, mouse Igα, Igβ, and other signaling molecules), their B-cells develop and mature normally.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., Proc Natl Acad Sci USA, 94:412-417 (1997) and the stepwise in vitro affinity maturation method by Wu et al., Proc Natl Acad Sci USA 95:6037 6042 (1998).

The term "monoclonal antibody" or "mAb" refers to an antibody that is synthesized and isolated by a separate clonal population of cells. The clonal population can be a clonal population of immortalized cells. In some embodiments, the immortalized cells in a clonal population are hybrid cells— hybridomas—typically produced by the fusion of individual B lymphocytes from immunized animals with individual cells from a lymphocytic tumour. Hybridomas are a type of constructed cells and do not exist in nature.

"Native antibodies" are usually heterotetrameric glycoproteins of about 150000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "isolated" used to describe various antibodies in this description refers to an antibody which has been identified and separated and/or regenerated from a cell or cell culture, in which the antibody is expressed. Impurities (contaminant components) from its natural environment are materials which would interfere with diagnostic or therapeutic uses of the polypeptide, and may include enzymes, hormones, and other proteinaceous or nonproteinaceous solutes. In preferred embodiments, an antibody is purified (1) to a degree sufficient to obtain at least 15 residues of N-terminal or internal amino acid sequence by use of a spinning cup sequenator (Edman sequenator), or (2) to homogeneity by SDS-PAGE under nonreducing or reducing conditions using Coomassie Brilliant Blue, or preferably silver stain. Isolated antibody includes the antibody in situ within recombinant cells since at least one component of the polypeptide's natural environment will not be present. Isolated polypeptide is typically prepared by at least one purification step.

An "isolated" nucleic acid molecule is one which is identified and separated from at least one nucleic acid molecule-impurity, which the former is bound to in the natural source of antibody nucleic acid. An isolated nucleic acid molecule is different from the form or set in which it is found under natural conditions. Thus, an isolated nucleic acid molecule is different from a nucleic acid molecule that exists in cells under natural conditions. An isolated nucleic acid molecule however includes a nucleic acid molecule located in cells in which the antibody is normally expressed, for example, if the nucleic acid molecule has a chromosomal localization that is different from its localization in cells under natural conditions.

The term "epitope" as used herein is intended to refer to a portion (determinant) of an antigen that specifically binds to a binding molecule (for example, an antibody or a related molecule, such as a bispecific binding molecule). Epitope determinants usually consist of chemically active surface groupings of molecules such as amino acids or carbohydrates or sugar side chains and typically comprise specific three dimensional structural characteristics, as well as specific charge characteristics. Epitopes can be either "linear" or "conformational". In a linear epitope, all of the points of interaction between a protein (e.g. an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope of an antigen is determined, it is possible to generate antibodies to that epitope using techniques well known in the art. In addition, generation and characterization of antibodies or other binding molecules may elucidate information about desirable epitopes. Based on this information, it is then possible to competitively screen antibodies for binding to the same or identical epitopes, e.g. by conducting competition studies to find binding molecules that compete with one another for binding to the antigen.

The term "peptide linker" as used herein is intended to mean any peptide having the ability to combine domains, with a length which depends on the domains which it binds to each other, and comprising any amino acid sequence. Preferably, the peptide linker has a length of more than 5 amino acids and consists of any set of amino acids selected from G, A, S, P, E, T, D, K.

The term "in vitro" refers to a biological entity, a biological process, or a biological reaction outside the body under artificial conditions. For example, a cell grown in vitro is to be understood as a cell grown in an environment outside the body, e.g. in a test tube, a culture vial, or a microtiter plate.

The term "$IC_{50}$" (inhibitory concentration 50%), as used herein, refers to concentrations of drug, at which a measurable activity or response, for example, growth/proliferation of cells such as tumor cells, is inhibited by 50%. $IC_{50}$ value can be calculated using appropriate dose-response curves, using special statistical software for curve fitting.

The term GI50 (growth inhibition 50%) refers to concentrations of drug, at which proliferation of cells, such as tumor cells, is inhibited by 50%.

The term "ED50" (EC50) (50% effective dose/concentration) refers to concentrations of drug producing 50% biological effect (which may include cytoxicity).

The term "antiproliferative activity" is intended to refer to stopping or inhibiting growth of cells, such as cancer cells.

The term antibody "effector function" refers to biological activities attributable to the Fc-region (native Fc-region sequence or Fc-region amino acid variants) of an antibody, which vary with the antibody isotype. Examples of antibody effector functions include: $Cl_q$ binding and complement dependent cytotoxicity; Fc receptor binding; antibody-dependent cell-mediated cytotoxicity (ADCC); phagocytosis; down regulation of cell surface receptors (e.g. B-cell receptor, BCR), and B-cell activation.

"Antibody-dependent cellular cytotoxicity" or "ADCC" refers to a cell-mediated response, in which nonspecific cytotoxic cells that express Fc receptors (FcR) (for example, natural killer (NK) cells, neutrophils, and macrophages) recognize bound antibody on a target cell and subsequently cause lysis or phagocytosis of the target cell. The primary cells for mediating ADCC, NK cells, express FcγRJII only, whereas monocytes express FcγRI, FcγRII and FcγRIII. FcR expression on hematopoietic cells is summarized in Table 3 on page 464 of Ravetch and Kinet, Annu. Rev. Immunol 9: 457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al. PNAS (USA) 95: 652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA ("activating receptor") and FcγRIIB ("inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daëron, Annu. Rev. Immunol. 15: 203-234 (1997)). FcRs are reviewed in Ravetch and Kinet, Annu. Rev. Immunol 9: 457-92 (1991). Other FcRs, including those to be identified in the future, are encompassed by the term "FcR" herein. The term also includes the neonatal receptor, FcRn, which is responsible for the transfer of maternal IgGs to the fetus.

"Complement dependent cytotoxicity" and "CDC" refer to the ability of a molecule to lyse a target in the presence of complement. The complement activation pathway is initiated by the binding of the first component of the complement system (C1q) to a molecule {e.g. an antibody) complexed with a cognate antigen. To assess complement activation, a CDC assay, e.g. as described in Gazzano-Santoro et al., J. Immunol. Methods 202: 163 (1996).

The term "identity" or "homology" is construed to mean the percentage of amino acid residues in the candidate sequence that are identical with the residue of a corresponding sequence to which it is compared, after comparing the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g. Sequence Analysis Software Package, Genetics Computer Group, University of Wisconsin Biotechnology Center, 1710 University Ave., Madison, WI 53705). This software matches similar sequences by assigning a degree of homology to various substitutions, deletions (eliminations), and other modifications.

The term "homologous" with regard to a polypeptide sequence of an antibody should be construed as an antibody exhibiting at least 70%, preferably 80%, more preferably 90% and most preferably 95% sequence identity relative to a polypeptide sequence. The term in relation to a nucleic acid sequence should be construed as a sequence of nucleotides exhibiting at least 85%, preferably 90%, more preferably 95% and most preferably 97% sequence identity relative to a nucleic acid sequence.

Modification(s) of amino acid sequences of antibodies described herein are provided. For example, it may be desirable to improve the binding affinity and/or other biological properties of the antibody. Amino acid sequence variants of antibody are prepared by introducing appropriate nucleotide changes into the antibody nucleic acid, or by peptide synthesis. Such modifications include, for example, deletions, and/or insertions and/or substitutions of residues within the amino acid sequences of antibody. Any combination of deletion, insertion, and substitution is made to arrive at the final construct, provided that the final construct possesses the desired characteristics. The amino acid changes also may alter post-translational processes in the antibody, such as changing the number or position of glycosylation sites.

Variant of modification of amino acid sequences of antibodies using amino acid substitutions. Such a variant is substitution of at least one amino acid residue in the antibody molecule with a different residue. The sites of greatest interest for substitutional mutagenesis include hypervariable regions or CDRs, but FR or Fc alterations are also contemplated. Conservative substitutions are shown in Table A under "preferred substitutions". If such substitutions cause alteration of the biological activity, further substantial changes can be made, which are denoted as "exemplary substitutions" set forth in Table A, or alterations described in more detail below when describing amino acid classes, and also product screening may be performed.

TABLE A

| Original residue | Exemplary substitutions | Preferred substitutions |
|---|---|---|
| Ala (A) | Val; Leu; Ile | Val |
| Arg (R) | Lys; Gin; Asn. | Lys |
| Asn (N) | Gin; His; Asp, Lys; Arg | Gin |
| Asp (D) | Glu; Asn | Glu |
| Cys (C) | Ser; Ala | Ser |
| Gln (Q) | Asn; Glu | Asn |
| Glu (E) | Asp; Gin | Asp |
| Gly (G) | Ala | Ala |
| His (H) | Asn; Gin; Lys; Arg; | Leu |
| Ile (I) | Leu; Val; Met; Ala.; Phe; Norleucine | Ile |
| Leu (L) | Norleucine; Ile; Val; Met; Ala; Phe | Ile |
| Lys (K) | Arg; Gin; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-strand DNA or RNA, a single-strand DNA or RNA, or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Thus, isolated nucleic acids obtained by recombinant genetics, by means, for example, of host cells, or obtained by chemical synthesis should also be mentioned here.

A reference to a nucleotide sequence encompasses the complement thereof unless otherwise specified. Thus, a reference to a nucleic acid having a particular sequence should be understood as one which encompasses the complementary strand thereof with the complementary sequence thereof.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader sequence is operably linked to DNA for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

The term "vector" as used herein means a nucleic acid molecule capable of transporting another nucleic acid to which it has been linked. In some embodiments, a vector is a plasmid, i.e., a circular double stranded piece of DNA into which additional DNA segments may be ligated. In some embodiments, a vector is a viral vector, wherein additional DNA segments may be ligated into the viral genome. In some embodiments, vectors are capable of autonomous replication in a host cell into which they are introduced (e.g. bacterial vectors having a bacterial origin site of replication and episomal mammalian vectors). In further embodiments, vectors (e.g. non-episomal mammalian vectors) can be integrated into the genome of a host cell upon introduction into a host cell, and thereby are replicated along with the host gene. Moreover, certain vectors are capable of directing the expression of genes to which they are operatively linked. Such vectors are referred to herein as "recombinant expression vectors" (or simply, "expression vectors").

The term "recombinant host cell" (or simply "host cell") as used herein is intended to refer to a cell into which a recombinant expression vector has been introduced. The present invention relates to host cells, which may include, for example, a vector according to the invention described above. The present invention also relates to host cells that comprise, for example, a nucleotide sequence encoding a heavy chain or antigen-binding portions thereof, a light chain-encoding nucleotide sequence or antigen-binding portions thereof, or both, of the first binding domain and/or second binding domain of a binding molecule of the invention. It should be understood that "recombinant host cell" and "host cell" are intended to refer not only to a particular subject cell but to the progeny of such a cell as well. Since modifications may occur in succeeding generations due to either mutation or environmental influences, such progeny may not, in fact, be identical to a parental cell, however, such cells are still included within the scope of the term "host cell" as used herein.

The term "excipient" is used herein to describe any ingredient other than the compound(s) of the invention.

The term "disease or disorder mediated by GITR" refers to any disease or disorder that is either directly, or indirectly associated with GITR, including etiology, development, progression, persistence or pathology of a disease or disorder.

"Treat", "treating" and "treatment" refer to a method of alleviating or abrogating a biological disorder and/or at least one of attendant symptoms thereof. As used herein, to "alleviate" a disease, disorder or condition means reducing the severity and/or occurrence frequency of the symptoms of a disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

The term "disorder" means any condition that would benefit from treatment with the compound of the present invention. The definition of this term includes chronic and acute disorders or diseases including those pathological conditions that predispose the mammal to the disorder in question.

The terms "cancer" and "cancerous" refer to a physiological condition or describe a physiological condition in mammals that is typically characterized by unregulated growth/proliferation of cells. The definition encompasses both benign and malignant cancerous diseases. Examples of cancerous diseases include, but are not limited to, carcinoma, lymphoma, blastoma, sarcoma, and leukemia. More particular examples of such cancerous diseases include squamous cell cancer, small-cell lung cancer, non-small cell lung cancer, adenocarcinoma of the lung and squamous carcinoma of the lung, peritoneal cancer, hepatocellular cancer, stomach cancer including gastrointestinal cancer, pancreatic cancer, glioblastoma, glioma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, and various head and neck cancers.

The terms "immune response", "autoimmune response" and "autoimmune inflammation" refer, for example, to the action of lymphocytes, antigen-presenting cells, phagocytic cells, granulocytes and soluble macromolecules produced by said cells or liver cells (including antibodies, cytokines and complement produced in the result of selective damage, destruction or elimination of invasive pathogens, cells or tissues infected with pathogens, cancer cells or, in cases of autoimmunity or pathological inflammation, normal cells or tissues from the human body).

"Therapeutically effective amount" is intended to refer to that amount of the therapeutic agent being administered which will relieve to some extent one or more of the symptoms of the disorder being treated.

The term "chronic" use refers to continued (uninterrupted) use of agent(s) as opposed to acute (transient) route of administration so as to sustain the initial therapeutic effect (activity) for a long period of time.

"Intermittent" use refers to treatment that is not carried out consistently without interruptions, but which is rather periodic in nature.

As used herein, the words "comprise," "have," "include," or variations such as "comprises," "comprising," "has," "having," "includes" or "including", and all grammatical variations thereof will be understood to imply the inclusion of a stated integer or group of integers but not the exclusion of any other integer or group of integers.

DETAILED DESCRIPTION OF THE INVENTION

Antibody

The present invention relates to a monoclonal antibody that specifically binds to GITR.

In one aspect, the present invention relates to a monoclonal antibody or antigen-binding fragment thereof that specifically binds to GITR comprising:

(a) a heavy chain variable domain comprising:

(i) CDR1 comprising an amino acid sequence selected from the group:

```
                                     (SEQ ID NO: 1)
            NYGMH
            or
                                     (SEQ ID NO: 12)
            YYWMY;
```

(ii) CDR2 comprising an amino acid sequence selected from the group:

```
                                     (SEQ ID NO: 2)
            VIWFDGSNKFYTDSVKG
            or
                                     (SEQ ID NO: 13)
            AISWNGGRTYYAESMKG;
```

(iii) CDR3 comprising an amino acid sequence selected from the group:

```
                                     (SEQ ID NO: 3)
            ELGGYYYDSSGFRPYYYGMDV
            or
                                     (SEQ ID NO: 14)
            NRYYSDPNYGMNL,
``` and (b) a light chain variable domain comprising:

(i) CDR1 comprising an amino acid sequence selected from the group:

```
                                     (SEQ ID NO: 7)
            RASQSIGSWLA
            or
                                     (SEQ ID NO: 17)
            TGTSTDIGTYKYIS;
```

(ii) CDR2 comprising an amino acid sequence selected from the group:

```
                                     (SEQ ID NO: 8)
            AASTLQR
            or
                                     (SEQ ID NO: 18)
            GVSHRPS;
```

(iii) CDR3 comprising an amino acid sequence selected from the group:

```
                                     (SEQ ID NO: 9)
            QQSHSHPLT
            or
                                     (SEQ ID NO: 19)
            SSYTSSGTVV.
```

In some embodiments, a monoclonal antibody or antigen-binding fragment thereof comprises a heavy chain variable domain comprising CDR 1, 2 and 3 comprising amino acid sequences represented by the sequences of SEQ ID NOs: 1, 2 and 3, respectively.

In some embodiments, a monoclonal antibody or antigen-binding fragment thereof comprises a heavy chain variable domain comprising CDR 1, 2 and 3 comprising amino acid sequences represented by the sequences of SEQ ID NOs: 12, 13 and 14, respectively.

In some embodiments, a monoclonal antibody or antigen-binding fragment thereof comprises a light chain variable domain comprising CDR 1, 2 and 3 comprising amino acid sequences represented by SEQ ID NOs: 7, 8 and 9, respectively.

In some embodiments, a monoclonal antibody or antigen-binding fragment thereof comprises a light chain variable domain comprising CDR 1, 2 and 3 comprising amino acid sequences represented by SEQ ID NOs: 17, 18 and 19, respectively.

In some embodiments, a monoclonal antibody or antigen-binding fragment thereof comprises:

a heavy chain variable domain comprising CDRs 1, 2 and 3 comprising amino acid sequences represented by the sequences of SEQ ID NOs: 1, 2 and 3, respectively;

a light chain variable domain comprising CDRs 1, 2 and 3 comprising amino acid sequences represented by the sequences of SEQ ID NOs: 7, 8 and 9, respectively.

In some embodiments, a monoclonal antibody or antigen-binding fragment thereof comprises:

a heavy chain variable domain comprising CDRs 1, 2 and 3 comprising amino acid sequences represented by the sequences of SEQ ID NOs: 12, 13 and 14, respectively;

a light chain variable domain comprising CDRs 1, 2 and 3 comprising amino acid sequences represented by the sequences of SEQ ID NOs: 17, 18 and 19, respectively.

In some embodiments, a monoclonal antibody or antigen-binding fragment thereof comprises a heavy chain variable domain comprising an amino acid sequence that is at least 90% homologous to the amino acid sequence (SEQ ID NO: 4)
EVQLVQSGGGVVQPGKSLRLSCAASGFTFSNYGMHWVRQ

APGKGLEWVAVIWFDGSNKFYTDSVKGRFTISRDNSKDT

LSLQMNSLRAEDTAVYYCARELGGYYYDSSGFRPYYYGM

DVWGQGTMVTVSS.

In some embodiments, a monoclonal antibody or antigen-binding fragment thereof comprises a heavy chain variable domain comprising the amino acid sequence (SEQ ID NO: 4)
EVQLVQSGGGVVQPGKSLRLSCAASGFTFSNYGMHWVRQ

APGKGLEWVAVIWFDGSNKFYTDSVKGRFTISRDNSKDT

LSLQMNSLRAEDTAVYYCARELGGYYYDSSGFRPYYYGM

DVWGQGTMVTVSS.

In some embodiments, a monoclonal antibody or antigen-binding fragment thereof comprises a heavy chain variable domain comprising an amino acid sequence that is at least 90% homologous to the amino acid sequence (SEQ ID NO: 15)
QVQLVQSGGGLVQPGGSLRLSCAASGFTFSYYWMYWVR

QAPGKGLEWVSAISWNGGRTYYAESMKGRFTISRDNAQ

NTLYLQMNSLKSEDTAVYYCAKNRYYSDPNYGMNLWGK

GTTVTVSS.

In some embodiments, a monoclonal antibody or antigen-binding fragment thereof comprises a heavy chain variable domain comprising the amino acid sequence (SEQ ID NO: 15)
QVQLVQSGGGLVQPGGSLRLSCAASGFTFSYYWMYWVR

QAPGKGLEWVSAISWNGGRTYYAESMKGRFTISRDNAQ

NTLYLQMNSLKSEDTAVYYCAKNRYYSDPNYGMNLWGK

GTTVTVSS.

In some embodiments, a monoclonal antibody or antigen-binding fragment thereof comprises a light chain variable domain comprising an amino acid sequence that is at least 90% homologous to the amino acid sequence (SEQ ID NO: 10)
DVVMTQSPSSVSASVGDRVTITCRASQSIGSWLAWYQQKPGEAPKLLIYA

ASTLQRGVPSRFSGGGYGTEFTLTISSLQPEDFATYFCQQSHSHPLTFGG

GTKVEIK.

In some embodiments, a monoclonal antibody or antigen-binding fragment thereof comprises a light chain variable domain comprising the amino acid sequence (SEQ ID NO: 10)
DVVMTQSPSSVSASVGDRVTITCRASQSIGSWLAWYQQKPGEAPKLLIYA

ASTLQRGVPSRFSGGGYGTEFTLTISSLQPEDFATYFCQQSHSHPLTFGG

GTKVEIK.

In some embodiments, a monoclonal antibody or antigen-binding fragment thereof comprises a light chain variable domain comprising an amino acid sequence that is at least 90% homologous to the amino acid sequence (SEQ ID NO: 20)
QSALTQPASVSGSPGQSITISCTGTSTDIGTYKYISWYQQHPGKAPKLIT

YGVSHRPSGVSDRFSGSKSDNTASLTISGLQAEDEADYYCSSYTSSGTVV

FGGGTKVTVL.

In some embodiments, a monoclonal antibody or antigen-binding fragment thereof comprises a light chain variable domain comprising the amino acid sequence (SEQ ID NO: 20)
QSALTQPASVSGSPGQSITISCTGTSTDIGTYKYISWYQQHPGKAPKLIT

YGVSHRPSGVSDRFSGSKSDNTASLTISGLQAEDEADYYCSSYTSSGTVV

FGGGTKVTVL.

In some embodiments, a monoclonal antibody or antigen-binding fragment thereof comprises:

a heavy chain variable domain comprising an amino acid sequence that is at least 90% homologous to the amino acid sequence (SEQ ID NO: 4)
EVQLVQSGGGVVQPGKSLRLSCAASGFTFSNYGMHWVRQAPGKGLEWVAV

IWFDGSNKFYTDSVKGRFTISRDNSKDTLSLQMNSLRAEDTAVYYCAREL

GGYYYDSSGFRPYYYGMDVWGQGTMVTVSS;

a light chain variable domain comprising an amino acid sequence that is at least 90% homologous to the amino acid sequence (SEQ ID NO: 10)
DVVMTQSPSSVSASVGDRVTITCRASQSIGSWLAWYQQKPGEAPKLLIYA

ASTLQRGVPSRFSGGGYGTEFTLTISSLQPEDFATYFCQQSHSHPLTFGG

GTKVEIK.

In some embodiments, a monoclonal antibody or antigen-binding fragment thereof comprises:

a heavy chain variable domain comprising the amino acid sequence (SEQ ID NO: 4)
EVQLVQSGGGVVQPGKSLRLSCAASGFTFSNYGMHWVRQAPGKGLEWVAV

IWFDGSNKFYTDSVKGRFTISRDNSKDTLSLQMNSLRAEDTAVYYCAREL

GGYYYDSSGFRPYYYGMDVWGQGTMVTVSS;

a light chain variable domain comprising the amino acid sequence (SEQ ID NO: 10)
DVVMTQSPSSVSASVGDRVTITCRASQSIGSWLAWYQQKPGEAPKLLIYA

ASTLQRGVPSRFSGGGYGTEFTLTISSLQPEDFATYFCQQSHSHPLTFGG

GTKVEIK.

In some embodiments, a monoclonal antibody or antigen-binding fragment thereof comprises:
   a heavy chain variable domain comprising an amino acid sequence that is at least 90% homologous to the amino acid sequence of SEQ ID NO:

(SEQ ID NO: 15)
QVQLVQSGGGLVQPGGSLRLSCASGFTFSYYWMYWVRQAPGKGLEWVSAI

SWNGGRTYYAESMKGRFTISRDNAQNTLYLQMNSLKSEDTAVYYCAKNRY

YSDPNYGMNLWGKGTTVTVSS;

a light chain variable domain comprising an amino acid sequence that is at least 90% homologous to the amino acid sequence (SEQ ID NO: 20)
QSALTQPASVSGSPGQSITISCTGTSTDIGTYKYISWYQQHPGKAPKLIT

YGVSHRPSGVSDRFSGSKSDNTASLTISGLQAEDEADYYCSSYTSSGTVV

FGGGTKVTVL.

In some embodiments, a monoclonal antibody or antigen-binding fragment thereof comprises:
   a heavy chain variable domain comprising the amino acid sequence (SEQ ID NO: 15)
QVQLVQSGGGLVQPGGSLRLSCASGFTFSYYWMYWVRQAPGKGLEWVSAI

SWNGGRTYYAESMKGRFTISRDNAQNTLYLQMNSLKSEDTAVYYCAKNRY

YSDPNYGMNLWGKGTTVTVSS;

a light chain variable domain comprising the amino acid sequence (SEQ ID NO: 20)
QSALTQPASVSGSPGQSITISCTGTSTDIGTYKYISWYQQHPGKAPKLIT

YGVSHRPSGVSDRFSGSKSDNTASLTISGLQAEDEADYYCSSYTSSGTVV

FGGGTKVTVL.

In some embodiments, a GITR-specific monoclonal antibody is a full length IgG antibody.

In some embodiments, the monoclonal IgG antibody is of human IgG1, IgG2, IgG3 or IgG4 isotype.

In some embodiments, the monoclonal IgG antibody is of human IgG1 isotype.

In some embodiments, a GITR-specific monoclonal antibody comprises the E358R mutation in the Fc fragment to increase agonist properties, antibody-dependent cellular cytotoxicity (ADCC), but not complement-dependent cytotoxicity (CDC).

In some embodiments, a monoclonal antibody comprises a heavy chain comprising an amino acid sequence that is at least 90% homologous to the sequence (SEQ ID NO: 5)
EVQLVQSGGGVVQPGKSLRLSCAASGFTFSNYGMHWVRQAPGKGLEWVAV

IWFDGSNKFYTDSVKGRFTISRDNSKDTLSLQMNSLRAEDTAVYYCAREL

GGYYYDSSGFRPYYYGMDVWGQGTMVTVSSASTKGPSVFPLAPSSKSTSG

GTAALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHYT

QKSLSLSPGK.

In some embodiments, a monoclonal antibody comprising a heavy chain comprising the amino acid sequence (SEQ ID NO: 5)
EVQLVQSGGGVVQPGKSLRLSCAASGFTFSNYGMHWVRQAPGKGLEWVAV

IWFDGSNKFYTDSVKGRFTISRDNSKDTLSLQMNSLRAEDTAVYYCAREL

GGYYYDSSGFRPYYYGMDVWGQGTMVTVSSASTKGPSVFPLAPSSKSTSG

GTAALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHYT

QKSLSLSPGK.

In some embodiments, a monoclonal antibody comprises a heavy chain comprising an amino acid sequence that is at least 90% homologous to the sequence (SEQ ID NO: 6)
EVQLVQSGGGVVQPGKSLRLSCAASGFTFSNYGMHWVRQAPGKGLEWVAV

IWFDGSNKFYTDSVKGRFTISRDNSKDTLSLQMNSLRAEDTAVYYCAREL

GGYYYDSSGFRPYYYGMDVWGQGTMVTVSSASTKGPSVFPLAPSSKSTSG

GTAALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTIS

KAKGQPRRPQVYTLPPSRDELTKNQVSLTCLVKGFYPSDIAVEWESNGQP

ENNYKTTPPVLDSDGSFFLYSKLTVDKSRWQQGNVFSCSVMHEALHNHYT

QKSLSLSPGK.

In some embodiments, a monoclonal antibody comprises a heavy chain comprising the amino acid sequence (SEQ ID NO: 6)
EVQLVQSGGGVVQPGKSLRLSCAASGFTFSNYGMHWVRQAPGKGLEWVAVI

WFDGSNKFYTDSVKGRFTISRDNSKDTLSLQMNSLRAEDTAVYYCARELGG

YYYDSSGFRPYYYGMDVWGQGTMVTVSSASTKGPSVFPLAPSSKSTSGGTA

ALGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPR

RPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPG

K.

In some embodiments, a monoclonal antibody comprises a light chain comprising an amino acid sequence that is at least 90% homologous to the sequence (SEQ ID NO: 11)
DVVMTQSPSSVSASVGDRVTITCRASQSIGSWLAWYQQKPGEAPKLLIYAA

STLQRGVPSRFSGGGYGTEFTLTISSLQPEDFATYFCQQSHSHPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

In some embodiments, a monoclonal antibody comprises a light chain comprising the amino acid sequence (SEQ ID NO: 11)
DVVMTQSPSSVSASVGDRVTITCRASQSIGSWLAWYQQKPGEAPKLLIYAA

STLQRGVPSRFSGGGYGTEFTLTISSLQPEDFATYFCQQSHSHPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

In some embodiments, a monoclonal antibody comprises:
a heavy chain comprising an amino acid sequence that is at least 90% homologous to the sequence (SEQ ID NO: 5)
EVQLVQSGGGVVQPGKSLRLSCAASGFTFSNYGMHWVRQAPGKGLEWVAVI

WFDGSNKFYTDSVKGRFTISRDNSKDTLSLQMNSLRAEDTAVYYCARELGG

YYYDSSGFRPYYYGMDVWGQGTMVTVSSASTKGPSVFPLAPSSKSTSGGTA

ALGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTIP

PVLDSDGSFFLYSKLTVDKSRWQQGNVFSCSVMHEALHNHYTQKSLSLSPG

K;

a light chain comprising an amino acid sequence that is at least 90% homologous to the sequence (SEQ ID NO: 11)
DVVMTQSPSSVSASVGDRVTITCRASQSIGSWLAWYQQKPGEAPKLLIYAA

STLQRGVPSRFSGGGYGTEFTLTISSLQPEDFATYFCQQSHSHPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

In some embodiments, a monoclonal antibody that specifically binds to GITR is BCD166-01-001.

The monoclonal antibody BCD166-01-001 comprises:
a heavy chain comprising the amino acid sequence (SEQ ID NO: 5)
EVQLVQSGGGVVQPGKSLRLSCAASGFTFSNYGMHWVRQAPGKGLEWVAVI

WFDGSNKFYTDSVKGRFTISRDNSKDTLSLQMNSLRAEDTAVYYCARELGG

YYYDSSGFRPYYYGMDVWGQGTMVTVSSASTKGPSVFPLAPSSKSTSGGTA

ALGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTIP

PVLDSDGSFFLYSKLTVDKSRWQQGNVFSCSVMHEALHNHYTQKSLSLSPG

K;

a light chain comprising the amino acid sequence (SEQ ID NO: 11)
DVVMTQSPSSVSASVGDRVTITCRASQSIGSWLAWYQQKPGEAPKLLIYAA

STLQRGVPSRFSGGGYGTEFTLTISSLQPEDFATYFCQQSHSHPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

In some embodiments, a monoclonal antibody comprises:
a heavy chain comprising an amino acid sequence that is at least 90% homologous to the sequence (SEQ ID NO: 6)
EVQLVQSGGGVVQPGKSLRLSCAASGFTFSNYGMHWVRQAPGKGLEWVAVI

WFDGSNKFYTDSVKGRFTISRDNSKDTLSLQMNSLRAEDTAVYYCARELGG

YYYDSSGFRPYYYGMDVWGQGTMVTVSSASTKGPSVFPLAPSSKSTSGGTA

ALGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVFL

-continued

FPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPR

RPQVYTLPPSRDELTKNQVSLTCLVKGFYPSDIAVEWESNGQPENNYKTIP

PVLDSDGSFFLYSKLTVDKSRWQQGNVFSCSVMHEALHNHYTQKSLSLSPG

K;

a light chain comprising an amino acid sequence that is at least 90% homologous to the sequence (SEQ ID NO: 11)
DVVMTQSPSSVSASVGDRVTITCRASQSIGSWLAWYQQKPGEAPKLLIYAA

STLQRGVPSRFSGGGYGTEFTLTISSLQPEDFATYFCQQSHSHPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

In some embodiments, a monoclonal antibody that specifically binds to GITR is BCD166-02-001.

The difference between BCD166-02-001 and BCD166-01-001 is the E358R mutation in the Fc fragment to increase agonist properties, antibody-dependent cellular cytotoxicity (ADCC), but not complement-dependent cytotoxicity (CDC).

The monoclonal antibody BCD166-02-001 comprises:

a heavy chain comprising the amino acid sequence (SEQ ID NO: 6)
EVQLVQSGGGVVQPGKSLRLSCAASGFTFSNYGMHWVRQAPGKGLEWVAVI

WFDGSNKFYTDSVKGRFTISRDNSKDTLSLQMNSLRAEDTAVYYCARELGG

YYYDSSGFRPYYYGMDVWGQGTMVTVSSASTKGPSVFPLAPSSKSTSGGTA

ALGCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPR

RPQVYTLPPSRDELTKNQVSLTCLVKGFYPSDIAVEWESNGQPENNYKTIP

PVLDSDGSFFLYSKLTVDKSRWQQGNVFSCSVMHEALHNHYTQKSLSLSPG

K;

a light chain comprising the amino acid sequence (SEQ ID NO: 11)
DVVMTQSPSSVSASVGDRVTITCRASQSIGSWLAWYQQKPGEAPKLLIYAA

STLQRGVPSRFSGGGYGTEFTLTISSLQPEDFATYFCQQSHSHPLTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

In some embodiments, a monoclonal antibody comprises a heavy chain comprising an amino acid sequence that is at least 90% homologous to the sequence (SEQ ID NO: 16)
QVQLVQSGGGLVQPGGSLRLSCAASGFTFSYYWMYWVRQAPGKGLEWVSAI

SWNGGRTYYAESMKGRFTISRDNAQNTLYLQMNSLKSEDTAVYYCAKNRYY

SDPNYGMNLWGKGTTVTVSSASTKGPSVFPLAPSSKSTSGGTAALGCLVKD

YFPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKDT

LMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK.

In some embodiments, a monoclonal antibody comprises a heavy chain comprising the amino acid sequence (SEQ ID NO: 16)
QVQLVQSGGGLVQPGGSLRLSCAASGFTFSYYWMYWVRQAPGKGLEWVSAI

SWNGGRTYYAESMKGRFTISRDNAQNTLYLQMNSLKSEDTAVYYCAKNRYY

SDPNYGMNLWGKGTTVTVSSASTKGPSVFPLAPSSKSTSGGTAALGCLVKD

YFPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKDT

LMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK.

In some embodiments, a monoclonal antibody comprises a light chain comprising an amino acid sequence that is at least 90% homologous to the sequence (SEQ ID NO: 21)
QSALTQPASVSGSPGQSITISCTGTSTDIGTYKYISWYQQHPGKAPKLIIY

GVSHRPSGVSDRFSGSKSDNTASLTISGLQAEDEADYYCSSYTSSGTVVFG

GGTKVTVLGQPKAAPSVTLFPPSSEELQANKATLVCLISDFYPGAVTVAWK

ADSSPVKAGVETTTPSKQSNNKYAASSYLSLTPEQWKSHRSYSCQVTHEGS

TVEKTVAPTECS.

In some embodiments, a monoclonal antibody comprises a light chain comprising the amino acid sequence (SEQ ID NO: 21)
QSALTQPASVSGSPGQSITISCTGTSTDIGTYKYISWYQQHPGKAPKLIIY

GVSHRPSGVSDRFSGSKSDNTASLTISGLQAEDEADYYCSSYTSSGTVVFG

GGTKVTVLGQPKAAPSVTLFPPSSEELQANKATLVCLISDFYPGAVTVAWK

ADSSPVKAGVETTTPSKQSNNKYAASSYLSLTPEQWKSHRSYSCQVTHEGS

TVEKTVAPTECS.

In some embodiments, a monoclonal antibody comprises:

a heavy chain comprising an amino acid sequence that is at least 90% homologous to the sequence (SEQ ID NO: 16)
QVQLVQSGGGLVQPGGSLRLSCAASGFTFSYYWMYWVRQAPGKGLEWVSA
ISWNGGRTYYAESMKGRFTISRDNAQNTLYLQMNSLKSEDTAVYYCAKNR
YYSDPNYGMNLWGKGTTVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSP
GK.

a light chain comprising an amino acid sequence that is at least 90% homologous to the sequence (SEQ ID NO: 21)
QSALTQPASVSGSPGQSITISCTGTSTDIGTYKYISWYQQHPGKAPKLII
YGVSHRPSGVSDRFSGSKSDNTASLTISGLQAEDEADYYCSSYTSSGTVV
FGGGTKVTVLGQPKAAPSVTLFPPSSEELQANKATLVCLISDFYPGAVTV
AWKADSSPVKAGVETTTPSKQSNNKYAASSYLSLTPEQWKSHRSYSCQVT
HEGSTVEKTVAPTECS.

In some embodiments, a monoclonal antibody that specifically binds to GITR is BCD166-01-014.

The monoclonal antibody BCD166-01-014 comprises:

a heavy chain comprising the amino acid sequence
(SEQ ID NO: 16)
QVQLVQSGGGLVQPGGSLRLSCAASGFTFSYYWMYWVRQAPGKGLEWVSA
ISWNGGRTYYAESMKGRFTISRDNAQNTLYLQMNSLKSEDTAVYYCAKNR
YYSDPNYGMNLWGKGTTVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSP
GK.
a light chain comprising the amino acid sequence
(SEQ ID NO: 21)
QSALTQPASVSGSPGQSITISCTGTSTDIGTYKYISWYQQHPGKAPKLII
YGVSHRPSGVSDRFSGSKSDNTASLTISGLQAEDEADYYCSSYTSSGTVV
FGGGTKVTVLGQPKAAPSVTLFPPSSEELQANKATLVCLISDFYPGAVTV
AWKADSSPVKAGVETTTPSKQSNNKYAASSYLSLTPEQWKSHRSYSCQVT
HEGSTVEKTVAPTECS.

Nucleic Acid Molecules

The present invention also relates to nucleic acid molecules, in particular to sequences encoding a monoclonal antibody that specifically binds to GITR according to the invention, as described herein, optionally including any peptide linker sequence, which are connected therewith.

A reference to a nucleotide sequence encompasses the complement thereof unless otherwise specified. Thus, a reference to a nucleic acid having a particular sequence should be understood as one which encompasses the complementary strand thereof with the complementary sequence thereof. The term "polynucleotide" as used herein means a polymeric form of either nucleotides that are at least 10 bases in length, or ribonucleotides, or deoxyribonucleotides or a modified form of either type of nucleotide. The term includes single and double stranded forms.

In one aspect, the present invention relates to a nucleic acid molecule comprising a nucleotide sequence encoding an amino acid sequence selected from SEQ ID NOs: 1-21. A nucleic acid molecule can also comprise any combination of said nucleotide sequences.

In one aspect, the present invention relates to nucleic acid comprising a nucleotide sequence encoding a monoclonal antibody or antigen-binding fragment thereof that specifically binds to GITR, and comprises:

(a) a heavy chain variable domain comprising:

(i) CDR1 comprising an amino acid sequence selected from the group:

(SEQ ID NO: 1)
NYGMH
or
(SEQ ID NO: 12)
YYWMY;

(ii) CDR2 comprising an amino acid sequence selected from the group:

(SEQ ID NO: 2)
VIWFDGSNKFYTDSVKG
or
(SEQ ID NO: 13)
AISWNGGRTYYAESMKG;

(iii) CDR3 comprising an amino acid sequence selected from the group:

(SEQ ID NO: 3)
ELGGYYYDSSGFRPYYYGMDV
or
(SEQ ID NO: 14)
NRYYSDPNYGMNL, and (b) a light chain variable domain comprising:

(i) CDR1 comprising an amino acid sequence selected from the group:

(SEQ ID NO: 7)
RASQSIGSWLA
or
(SEQ ID NO: 17)
TGTSTDIGTYKYIS;

(ii) CDR2 comprising an amino acid sequence selected from the group:

```
                                    (SEQ ID NO: 8)
AASTLQR
or (SEQ ID NO: 18)
GVSHRPS;
```

(iii) CDR3 comprising an amino acid sequence selected from the group:

```
                                    (SEQ ID NO: 9)
QQSHSHPLT
or (SEQ ID NO: 19)
SSYTSSGTVV.
```

In some embodiments, a nucleic acid molecule comprises a nucleotide sequence that encodes monoclonal antibody or an antigen-binding fragment thereof comprising a heavy chain variable domain comprising CDRs 1, 2, and 3 comprising amino acid sequences represented by the sequences of SEQ ID NOs: 1, 2 and 3, respectively.

In some embodiments, a nucleic acid molecule comprises a nucleotide sequence that encodes monoclonal antibody or an antigen-binding fragment thereof comprising a heavy chain variable domain comprising CDRs 1, 2, and 3 comprising amino acid sequences represented by the sequences of SEQ ID NOs: 12, 13 and 14, respectively.

In some embodiments, a nucleic acid molecule comprises a nucleotide sequence encoding monoclonal antibody or an antigen-binding fragment thereof comprising a light chain variable domain comprising CDRs 1, 2, and 3 comprising amino acid sequences represented by the sequences of SEQ ID NOs: 7, 8 and 9, respectively.

In some embodiments, a nucleic acid molecule comprises a nucleotide sequence encoding monoclonal antibody or an antigen-binding fragment thereof comprising a light chain variable domain comprising CDRs 1, 2, and 3 comprising amino acid sequences represented by the sequences of SEQ ID NOs: 17, 18 and 19, respectively.

In some embodiments, a nucleic acid molecule comprises a nucleotide sequence encoding monoclonal antibody or antigen-binding fragment thereof comprising:
   a heavy chain variable domain comprising CDRs 1, 2 and 3 comprising amino acid sequences represented by the sequences of SEQ ID NOs: 1, 2 and 3, respectively;
   a light chain variable domain comprising CDRs 1, 2 and 3 comprising amino acid sequences represented by the sequences of SEQ ID NOs: 7, 8 and 9, respectively.

In some embodiments, a nucleic acid molecule comprises a nucleotide sequence encoding monoclonal antibody or antigen-binding fragment thereof comprising:
   a heavy chain variable domain comprising CDRs 1, 2 and 3 comprising amino acid sequences represented by the sequences of SEQ ID NOs: 12, 13 and 14, respectively;
   a light chain variable domain comprising CDRs 1, 2 and 3 comprising amino acid sequences represented by the sequences of SEQ ID NOs: 17, 18 and 19, respectively.

In some embodiments, a nucleic acid molecule comprises a nucleotide sequence encoding monoclonal antibody or an antigen-binding fragment thereof comprising a heavy chain variable domain comprising an amino acid sequence that is at least 90% homologous to the amino acid sequence of SEQ ID NO: 4.

In some embodiments, a nucleic acid molecule comprises a nucleotide sequence encoding monoclonal antibody or an antigen-binding fragment thereof comprising a heavy chain variable domain comprising the amino acid sequence of SEQ ID NO: 4.

In some embodiments, a nucleic acid molecule comprises a nucleotide sequence encoding monoclonal antibody or an antigen-binding fragment thereof comprising a heavy chain variable domain comprising an amino acid sequence that is at least 90% homologous to the amino acid sequence of SEQ ID NO: 15.

In some embodiments, a nucleic acid molecule comprises a nucleotide sequence encoding monoclonal antibody or an antigen-binding fragment thereof comprising a heavy chain variable domain comprising the amino acid sequence of SEQ ID NO: 15.

In some embodiments, a nucleic acid molecule comprises a nucleotide sequence encoding monoclonal antibody or an antigen-binding fragment thereof comprising a light chain variable domain comprising an amino acid sequence that is at least 90% homologous to the amino acid sequence of SEQ ID NO: 10.

In some embodiments, a nucleic acid molecule comprises a nucleotide sequence encoding monoclonal antibody or an antigen-binding fragment thereof comprising a light chain variable domain comprising the amino acid sequence of SEQ ID NO: 10.

In some embodiments, a nucleic acid molecule comprises a nucleotide sequence encoding monoclonal antibody or an antigen-binding fragment thereof comprising a light chain variable domain comprising an amino acid sequence that is at least 90% homologous to the amino acid sequence of SEQ ID NO: 20.

In some embodiments, a nucleic acid molecule comprises a nucleotide sequence encoding monoclonal antibody or an antigen-binding fragment thereof comprising a light chain variable domain comprising the amino acid sequence of SEQ ID NO: 20.

In some embodiments, a nucleic acid molecule comprises a nucleotide sequence encoding monoclonal antibody or antigen-binding fragment thereof comprising:
   a heavy chain variable domain comprising an amino acid sequence that is at least 90% homologous to the amino acid sequence of SEQ ID NO: 4;
   a light chain variable domain comprising an amino acid sequence that is at least 90% homologous to the amino acid sequence of SEQ ID NO: 10.

In some embodiments, a nucleic acid molecule comprises a nucleotide sequence encoding monoclonal antibody or antigen-binding fragment thereof comprising:
   a heavy chain variable domain comprising the amino acid sequence of SEQ ID NO: 4;
   a light chain variable domain comprising the amino acid sequence of SEQ ID NO: 10.

In some embodiments, a nucleic acid molecule comprises a nucleotide sequence encoding monoclonal antibody or antigen-binding fragment thereof comprising:
   a heavy chain variable domain comprising an amino acid sequence that is at least 90% homologous to the amino acid sequence of SEQ ID NO: 15;
   a light chain variable domain comprising an amino acid sequence that is at least 90% homologous to the amino acid sequence of SEQ ID NO: 20.

In some embodiments, a nucleic acid molecule comprises a nucleotide sequence encoding monoclonal antibody or antigen-binding fragment thereof comprising:

a heavy chain variable domain comprising the amino acid sequence of SEQ ID NO: 15;
a light chain variable domain comprising the amino acid sequence of SEQ ID NO: 20.

In some embodiments, the nucleic acid molecule comprises a nucleotide sequence encoding a monoclonal antibody that specifically binds to GITR which is a full-length IgG antibody.

In some embodiments, a nucleic acid molecule comprises a nucleotide sequence encoding a monoclonal IgG antibody which is of human IgG1, IgG2, IgG3 or IgG4 isotype.

In some embodiments, a nucleic acid molecule comprises a nucleotide sequence encoding a monoclonal IgG antibody which is of human IgG1 isotype.

In some embodiments, a nucleic acid molecule comprises a nucleotide sequence encoding a monoclonal antibody that specifically binds to GITR which includes the E358R mutation in the Fc fragment to increase agonist properties, antibody-dependent cellular cytotoxicity (ADCC), but not complement-dependent cytotoxicity (CDC).

In some embodiments, a nucleic acid molecule comprises a nucleotide sequence encoding a monoclonal antibody comprising a heavy chain comprising an amino acid sequence that is at least 90% homologous to the sequence of SEQ ID NO: 5.

In some embodiments, a nucleic acid molecule comprises a nucleotide sequence encoding a monoclonal antibody comprising a heavy chain comprising the amino acid sequence of SEQ ID NO: 5.

In some embodiments, a nucleic acid molecule comprises a nucleotide sequence encoding a monoclonal antibody comprising a heavy chain comprising an amino acid sequence that is at least 90% homologous to the sequence of SEQ ID NO: 6.

In some embodiments, a nucleic acid molecule comprises a nucleotide sequence encoding a monoclonal antibody comprising a heavy chain comprising the amino acid sequence of SEQ ID NO: 6.

In some embodiments, a nucleic acid molecule comprises a nucleotide sequence encoding a monoclonal antibody comprising a light chain comprising an amino acid sequence that is at least 90% homologous to the sequence of SEQ ID NO: 11.

In some embodiments, a nucleic acid molecule comprises a nucleotide sequence encoding a monoclonal antibody comprising a light chain comprising the amino acid sequence of SEQ ID NO: 11.

In some embodiments, a nucleic acid molecule comprises a nucleotide sequence encoding a monoclonal antibody that comprises:
a heavy chain comprising an amino acid sequence that is at least 90% homologous to the sequence of SEQ ID NO: 5;
a light chain comprising an amino acid sequence that is at least 90% homologous to the sequence of SEQ ID NO: 11.

In some embodiments, a nucleic acid molecule comprises a nucleotide sequence encoding a monoclonal antibody that comprises:
a heavy chain comprising the amino acid sequence of SEQ ID NO: 5;
a light chain comprising the amino acid sequence of SEQ ID NO: 11.

In some embodiments, a nucleic acid molecule comprises a nucleotide sequence encoding a monoclonal antibody that comprises:
a heavy chain comprising an amino acid sequence that is at least 90% homologous to the sequence of SEQ ID NO: 6;
a light chain comprising an amino acid sequence that is at least 90% homologous to the sequence of SEQ ID NO: 11.

In some embodiments, a nucleic acid molecule comprises a nucleotide sequence encoding a monoclonal antibody that comprises:
a heavy chain comprising the amino acid sequence of SEQ ID NO: 6;
a light chain comprising the amino acid sequence of SEQ ID NO: 11.

In some embodiments, a nucleic acid molecule comprises a nucleotide sequence encoding a monoclonal antibody comprising a heavy chain comprising an amino acid sequence that is at least 90% homologous to the sequence of SEQ ID NO: 16.

In some embodiments, a nucleic acid molecule comprises a nucleotide sequence encoding a monoclonal antibody comprising a heavy chain comprising the amino acid sequence of SEQ ID NO: 16.

In some embodiments, a nucleic acid molecule comprises a nucleotide sequence encoding a monoclonal antibody comprising a light chain comprising an amino acid sequence that is at least 90% homologous to the sequence of SEQ ID NO: 21.

In some embodiments, a nucleic acid molecule comprises a nucleotide sequence encoding a monoclonal antibody comprising a light chain comprising the amino acid sequence of SEQ ID NO: 21.

In some embodiments, a nucleic acid molecule comprises a nucleotide sequence encoding a monoclonal antibody that comprises:
a heavy chain comprising an amino acid sequence that is at least 90% homologous to the sequence of SEQ ID NO: 16;
a light chain comprising an amino acid sequence that is at least 90% homologous to the sequence of SEQ ID NO: 21.

In some embodiments, a nucleic acid molecule comprises a nucleotide sequence encoding a monoclonal antibody that comprises:
a heavy chain comprising the amino acid sequence of SEQ ID NO: 16;
a light chain comprising the amino acid sequence of SEQ ID NO: 21.

In some embodiments, a nucleic acid is DNA.

In any of the above embodiments, nucleic acid molecules can be isolated.

A nucleic acid molecule of the invention can be isolated from any source that produces a monoclonal antibody that specifically binds to GITR. In certain embodiments, a nucleic acid molecule of the invention can be synthesized, rather than isolated.

In one embodiment of the invention, nucleic acid molecules encoding VH (SEQ ID NO: 4 or SEQ ID NO: 15) or VL (SEQ ID NO: 10 or SEQ ID NO: 20) domains are transformed into antibody genes along the entire length by virtue of insertion into an expression vector already encoding heavy chain constant (CH) or light chain constant (CL) domains, respectively, such that the VH segment is operatively linked to the CH segment(s) within the vector, and/or the VL segment is operatively linked to the CL segment within the vector. In another embodiment of the invention, nucleic acid molecules encoding VH and/or VL domains are transformed into genes along the entire length of antibody by virtue of linking, e.g. ligating, a nucleic acid molecule encoding VH and/or VL domains to a nucleic acid molecule encoding CH and/or CL domains using standard molecular biological techniques. Nucleic acid molecules encoding the entire length of heavy and/or light chains may then be expressed from a cell into which they have been introduced.

Nucleic acid molecules may be used to express a large quantity of a recombinant monoclonal antibody that specifically binds to GITR.

Vector

In another aspect, the present invention relates to a vector suitable for the expression of any of nucleotide sequences described herein.

The present invention relates to vectors comprising nucleic acid molecules that encode any of the amino acid sequences of a monoclonal antibody that specifically binds to GITR or portions thereof (e.g. heavy chain sequences of a first binding domain and/or heavy and/or light chain sequences of a second binding domain), as described herein. The invention further relates to vectors comprising nucleic acid molecules encoding fusion proteins, modified antibodies, antibody fragments.

In some embodiments, a monoclonal antibody that specifically binds to GITR according to the invention is expressed by inserting a DNA partially or fully encoding the sequence of a first or second binding domain (e.g. light and heavy chain sequences where a binding domain comprises light and heavy chain sequences), obtained as described above, in expression vectors such that the genes are operatively linked to necessary expression control sequences, such as transcriptional and translational control sequences. Expression vectors include plasmids, retroviruses, adenoviruses, adeno-associated viruses (AAV), plant viruses, such as cauliflower mosaic virus, tobacco mosaic virus, cosmids, YACs, EBV derived episomes, and the like. DNA molecules may be ligated into a vector such that transcriptional and translational control sequences within the vector serve their intended function of regulating the transcription and translation of the DNA. An expression vector and expression control sequences may be chosen to be compatible with the expression host cell used. DNA molecules partially or fully encoding the sequences of first and second binding domains (for example, heavy and light chain sequences where a binding domain comprises a heavy and light chain sequence) can be introduced into individual vectors. In one embodiment, any combination of said DNA molecules is introduced into the same expression vector. DNA molecules can be introduced into an expression vector by standard methods (e.g. ligation of complementary restriction sites on an antibody gene fragment and vector, or blunt end ligation if no restriction sites are present).

A suitable vector is one that encodes functionally complete human CH or CL immunoglobulin sequences, with appropriate restriction site engineering so that any VH or VL sequence can easily be inserted and expressed, as described above. HC- and LC-encoding of genes in such vectors may contain intron sequences, resulting in enhanced overall antibody protein yields by stabilizing the corresponding mRNA. The intron sequences are flanked by splice donor and splice acceptor sites, which determine where RNA splicing will occur. Location of intron sequences can be either in variable or constant regions of antibody chains, or in both variable and constant regions when multiple introns are used. Polyadenylation and transcription termination may occur at a native chromosomal site downstream of coding regions. A recombinant expression vector can also encode a signal peptide that facilitates secretion of an antibody chain from a host cell. An antibody chain gene may be cloned into a vector such that the signal peptide is linked in-frame to the amino terminus of an immunoglobulin chain. The signal peptide can be an immunoglobulin signal peptide or a heterologous signal peptide (i.e., a signal peptide from a non-immunoglobulin protein).

In addition to antibody chain genes, the recombinant vector expression of the invention can carry regulatory sequences that control the expression of antibody chain genes in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g. the major late promoter adenovirus (AdMLP)), polyomavirus and strong mammalian promoters such as native immunoglobulin promoter or actin promoter. For further description of viral control elements and sequences thereof, see, e.g. U.S. Pat. Nos. 5,168,062, 4,510,245 and 4,968,615. Methods for expressing binding molecules, such as antibodies in plants, including a description of promoters and vectors, as well as transformation of plants are known in the art. See, e.g. U.S. Pat. No. 6,517,529. Methods for expressing polypeptides in bacterial cells or fungal cells, e.g. yeast cells, are also well known in the art.

In addition to antibody chain genes and regulatory sequences, the recombinant expression vectors of the invention may carry additional sequences, such as sequences that regulate replication of a vector in host cells (e.g. origins of replication) and selectable marker genes. The selectable marker gene facilitates the selection of host cells into which a vector has been introduced (see e.g. U.S. Pat. Nos. 4,399,216, 4,634,665 and 5,179,017). For example, typically the selectable marker gene confers resistance to medicinal agents, such as G418, hygromycin or methotrexate, on a host cell into which a vector has been introduced. For example, selectable marker genes include a dihydrofolate reductase (DHFR) gene (for use in dhfr-host cells during methotrexate selection/amplification), a neo gene (for G418 selection), and a glutamate synthetase gene.

The term "expression control sequence" as used herein is intended to refer to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "control sequences" is intended to include at least all components, the presence of which is essential for expression and processing, and can also include additional components, the presence of which is advantageous, for example, leader sequences and fusion partner sequences.

Host Cells

A further aspect of the present invention relates to methods for obtaining a monoclonal antibody that specifically binds to GITR according to the invention. One embodiment of the invention relates to a method for obtaining a monoclonal antibody that specifically binds to GITR, as defined herein, which comprises the production of a recombinant host cell capable of expressing a monoclonal antibody that specifically binds to GITR, culturing of said host cell under conditions suitable for expression/production of a monoclonal antibody that specifically binds to GITR, and isolation of a resulting monoclonal antibody that specifically binds to GITR. A monoclonal antibody that specifically binds to GITR produced by such expression in such recombinant host cells is referred to herein as "a recombinant monoclonal antibody that specifically binds to GITR". The invention also relates to the progeny of cells from such host cells, and a monoclonal antibody that specifically binds to GITR produced analogously.

Nucleic acid molecules encoding a monoclonal antibody that specifically binds to GITR according to the invention and vectors comprising these nucleic acid molecules can be used for transfection of a suitable mammalian or cell thereof, plant or cell thereof, bacterial or yeast host cell. Transformation can be by any known technique for introducing polynucleotides into a host-cell. Methods for introduction of heterologous polynucleotides into mammalian cells are well known in the art and include dextran-mediated transfection, cationic polymer-nucleic acid complex transfection, calcium phosphate precipitation, polybrene-mediated transfection, protoplast fusion, encapsulation of the polynucleotide(s) in liposomes, and direct microinjection of DNA into nuclei. In addition, nucleic acid molecules may be introduced into mammalian cells by viral vectors. Methods for transfecting cells are well known in the art. See, e.g. U.S. Pat. Nos. 4,399,216, 4,912,040, 4,740,461 and 4,959,455. Methods for transforming plant cells are well known in the art, including, e.g. Agrobacterium-mediated transformation, biolistic transformation, direct injection, electroporation and viral transformation. Methods of transforming bacterial and yeast cells are also well known in the art.

Mammalian cell lines used as hosts for transformation are well known in the art and include a plurality of immortalized cell lines available. These include, e.g. Chinese hamster ovary (CHO) cells, NS0 cells, SP2 cells, HEK-293T cells, FreeStyle 293 cells (Invitrogen), NIH-3T3 cells, HeLa cells, baby hamster kidney (BHK) cells, African green monkey kidney cells (COS), human hepatocellular carcinoma cells (e.g. Hep G2), A549 cells, and a number of other cell lines. Cell lines are selected by determining which cell lines have high expression levels and provide for necessary characteristics of protein produced. Other cell lines that may be used are insect cell lines, such as Sf9 or Sf21 cells. When recombinant expression vectors encoding a monoclonal antibody that specifically binds to GITR are introduced into mammalian host cells, the antibodies are produced by culturing the host cells for a period of time sufficient to allow for expression of the antibodies in host cells or, more preferably, secretion of the antibodies into the culture medium in which the host cells are grown. A monoclonal antibody that specifically binds to GITR can be reconstituted from a culture medium using standard protein purification techniques. Plant host cells include, e.g. *Nicotiana, Arabidopsis*, duckweed, corn, wheat, potato, etc. Bacterial host cells include *Escherichia* and *Streptomyces* species. Yeast host cells include *Schizosaccharomyces pombe, Saccharomyces cerevisiae* and *Pichia pastoris*.

Furthermore, level of production of a monoclonal antibody that specifically binds to GITR according to the invention from a production cell line can be enhanced using a number of known techniques. For example, the glutamine synthetase gene expression system (the GS system) is a common approach for enhancing expression under certain conditions. The GS system is discussed in whole or part in connection with EP No. 0216846, 0256055, 0323997 and 0338841.

It is likely that a monoclonal antibody that specifically binds to GITR of various cell lines or transgenic animals will have a different glycosylation profile as compared to each other. However, monoclonal antibody that specifically binds to GITR encoded by nucleic acid molecules described herein, or comprising amino acid sequences provided herein are part of the present invention, regardless of the glycosylation of the binding molecules, and, in general, regardless of the presence or absence of post-translational modifications.

Preparation of Antibodies

The invention also relates to methods and processes for obtaining a monoclonal antibody that specifically binds to GITR and antigen-binding fragments thereof.

Monoclonal Antibodies

Monoclonal antibodies may be prepared using the hybridoma method first described by Kohler, et al. Nature 256, 1975, p. 495, or may be prepared using recombinant DNA methods (U.S. Pat. No. 4,816,567).

In a hybridoma method, a mouse, or other appropriate host animal, such as a hamster, is immunized according to the above method to elicit lymphocytes that produce or are capable of producing antibodies that will specifically bind to protein used for immunization. According to another embodiment, lymphocytes can be obtained as a result of in vitro immunization. After immunization, the lymphocytes are fused with a myeloma cell line using a suitable fusing agent, such as polyethylene glycol, to produce a hybridoma cell.

The hybridoma cells, obtained in the above manner, may be cultured in a suitable culture medium that preferably contains one or more substances that inhibit the growth or survival of the unfused parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), i.e. substances which prevent the growth of HGPRT-deficient cells.

Preferred cells, used as component for myeloma cell fusion, are those that fuse efficiently, support stable high level production of antibodies by the selected antibody-producing cells, and are sensitive to a medium where the unfused parental cells are selected. Preferred myeloma cell lines are murine myeloma lines, such as those derived from MOPC-21 and MPC-11 mouse tumors available from the Salk Institute Cell Distribution Center, San Diego, California, USA, and SP-2 or X63-Ag8-653 cells available from the American Type Culture Collection, Rockville, Maryland, USA. Human myeloma and mouse-human heteromyeloma cell lines also have been described for the production of monoclonal antibodies (Kozbor, J. Immunol., 133, 1984, p. 3001).

Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal e.g, by intraperitoneal (i.p.) injection of the cells into mice.

The monoclonal antibodies secreted by the subclones can be separated from the culture medium, ascites fluid, or serum by conventional antibody purification techniques such as, for example, affinity chromatography (e.g. using protein A- or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g. by using oligonucleotide probes that are capable of specific binding to genes encoding the heavy and light chains of murine antibodies). The hybridoma cells serve as a preferred source of such DNA. Once isolated, the DNA may be placed into expression vectors, which are then transfected into host cells, such as E. coli cells, simian COS cells, Chinese Hamster Ovary (CHO) cells, or myeloma cells, that do not produce antibody protein without being transfected, to obtain the synthesis of monoclonal antibodies in the recombinant host cells.

In a further embodiment of the invention, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992), as well as combinatorial infection and in vivo recombination as a strategy for constructing very large phage libraries (Waterhouse et al., Nucl. Acids. Res. 21:2265-2266 (1993). Thus, these techniques are viable alternatives to traditional monoclonal antibody hybridoma techniques for isolation of monoclonal antibodies.

DNA that encodes an antibody may be modified, for example, so as to produce chimeric or fusion antibody polypeptides, for example, by substituting heavy chain and light chain (CH and CL) constant region sequences for the homologous murine sequences (U.S. Pat. No. 4,816,567 and Morrison, et al., Proc. Natl. Acad. Sci. USA: 81:6851 (1984), or by covalently fusing the immunoglobulin coding sequence with all or part of the coding sequence of a non-immunoglobulin polypeptide (heterologous polypeptide). The non-immunoglobulin polypeptide sequences can be substituted for the constant regions of antibody, or they can be substituted for the variable domains of antigen-binding center of antibody to create a chimeric bivalent antibody comprising one antigen-binding site having specificity for an antigen and another antigen-binding site having specificity for a different antigen.

Human Antibodies and Methodology Based on Phage Display Library

It is now possible to produce transgenic animals (e.g. mice) that are capable, after immunization, of producing a full range of human antibodies without endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies after antigen challenge (U.S. Pat. Nos. 5,545,806, 5,569,825, 5,591,669 (all of GenPharm); 5545807; and WO 97/17852).

Alternatively, phage display technology (McCafferty et al., Nature, 348:552-553 (1990) can be used to obtain human antibodies and antibody fragments in vitro from immunoglobulin variable (V) region gene repertoire from immunized donor bodies. According to this technique, antibody V-region genes are cloned in-frame with either a major or minor coat protein gene of a filamentous bacteriophage, such as M13 or fd, and displayed as functional antibody fragments on the surface of a phage particle. Because the filamentous particle contains a single-stranded DNA copy of the phage genome, selections based on the functional properties of the antibody also result in selection of a gene encoding an antibody exhibiting said properties. Thus, the phage mimics some of B-cell properties. Phage display can be performed in a variety of formats. Several sources of V-gene segments can be used for phage display. Clackson et al., Nature, 352:624-628 (1991) isolated various arrays of anti-oxazolone antibodies from a small random combinatorial library of V genes derived from the spleen of immunized mice. A repertoire of V genes from unimmunized human donors can be constructed and antibodies against a diverse array of antigens (including self-antigens) can be isolated essentially following the techniques described by Marks et al., J. Mol. Biol. 222:581-597 (1991).

As described above, human antibodies may also be generated by in vitro activated B cells (see U.S. Pat. Nos. 5,567,610 and 5,229,275).

Antibody Fragments

In certain circumstances, it is advisable to use antibody fragments rather than whole antibodies. The small sizes of the fragments contributes to rapid clearance thereof and may contribute to better penetration into dense tumors.

Various techniques have been developed for the production of antibody fragments. Traditionally, these fragments were derived via proteolytic digestion of intact antibodies. However, these fragments can now be obtained directly by recombinant host cells. Fab, Fv and ScFv antibody fragments can be expressed in and secreted from E. coli, thus allowing to facilitate the production of large amounts of these fragments. Antibody fragments can be isolated from the antibody phage libraries described above. According to another embodiment, Fab'-SH fragments can be directly isolated from E. coli and chemically coupled to form $F(ab')_2$ fragments (Carter et al., Bio/Technology 10:163-167 (1992). According to another approach, $F(ab')_2$ fragments can be isolated directly from recombinant host cell culture. Fab and $F(ab')_2$ with increased in vivo half-life retaining epitope binding receptor residues are described in U.S. Pat. No. 5,869,046. Other techniques for the production of antibody fragments will be apparent to those skilled in the art. In other embodiments of the invention, the antibody of choice is a single chain Fv fragment (scFv) (see WO 93/16185; U.S. Pat. Nos. 5,571,894 and 5,587,458). Fv and scFv are the only species with intact binding sites that are devoid of constant regions; as a result, they are suitable for reduced nonspecific binding during in vivo use. scFv fusion proteins may be constructed to yield fusion of an effector protein at either N- or C-terminus of an scFv. The antibody fragment may also be a "linear antibody", e.g. as described in U.S. Pat. No. 5,641,870. Such linear antibody fragments may be monospecific or bispecific.

Pharmaceutical Compositions

In another aspect, the invention provides a pharmaceutical composition comprising a monoclonal antibody that specifically binds to GITR as an active ingredient (or as the only active ingredient).

A pharmaceutical composition may include at least one monoclonal antibody that specifically binds to GITR and at least one of components selected from the group consisting of pharmaceutically acceptable and pharmacologically compatible excipients.

A pharmaceutical composition may include at least one monoclonal antibody that specifically binds to GITR and one or more additional binding molecules (e.g. antibodies) that target one or more of the corresponding surface receptors. In some embodiments of the invention, compositions are intended to improve, prevent, or treat disorders that may be associated with GITR.

"Pharmaceutical composition" means a composition comprising a monoclonal antibody that specifically binds to GITR according to the invention and at least one of components selected from the group consisting of pharmaceutically acceptable and pharmacologically compatible excipients, such as fillers, solvents, diluents, carriers, auxiliary, distributing agents, delivery agents, preservatives, stabilizers, emulsifiers, suspending agents, thickeners, prolonged delivery controllers, the choice and proportions of which depend on the type and route of administration and dosage. Pharmaceutical compositions of the present invention and methods of preparation thereof will be undoubtedly apparent to those skilled in the art. Pharmaceutical compositions should preferably be manufactured in compliance with the GMP (Good Manufacturing Practice) requirements. The composition may comprise a buffer composition, tonicity agents, stabilizers and solubilizers. Prolonged action of a composition may be achieved by agents slowing down absorption of active pharmaceutical ingredient, for example, aluminum monostearate and gelatine. Examples of suitable carriers, solvents, diluents and delivery agents include water, ethanol, polyalcohols and their mixtures, oils, and organic esters for injections.

"Medicament (drug)" is a compound or a mixture of compounds as a pharmaceutical composition in the form of tablets, capsules, powders, lyophilisates, injections, infusion, ointments and other ready forms intended for restoration, improvement or modification of physiological functions in humans and animals, and for treatment and preventing of diseases, for diagnostics, anesthesia, contraception, cosmetology and others. Any method for administering peptides, proteins or antibodies which is accepted in the art may be suitably employed for a monoclonal antibody that specifically binds to GITR according to the invention.

The term "pharmaceutically acceptable" refers to one or more compatible liquid or solid components that are suitable for administration in a mammal, preferably a human.

The term "excipient" is used herein to describe any ingredient other than the above ingredients of the invention. These are substances of inorganic or organic nature which are used in the pharmaceutical manufacturing in order to give drug products the necessary physicochemical properties.

The terms "buffer", "buffer composition", "buffering agent" refers to a solution, which is capable of resisting changes in pH by the action of its acid-base conjugate components, and which allows the drug of a monoclonal antibody that specifically binds to CD20 to resist changes in pH. Generally, the pharmaceutical composition preferably has a pH in the range from 4.0 to 8.0. Examples of buffers used include, but are not limited to, acetate, phosphate, citrate, histidine, succinate, etc. buffer solutions.

The terms "tonic agent", "osmolyte" or "osmotic agent", as used herein, refer to an excipient that can increase the osmotic pressure of a liquid antibody formulation. "Isotonic" drug is a drug that has an osmotic pressure equivalent to that of human blood. Isotonic drugs typically have an osmotic pressure from about 250 to 350 mOsm/kg. Isotonic agents used include, but are not limited to, polyols, saccharides and sucrose, amino acids, metal salts, for example, sodium chloride, etc.

"Stabilizer" refers to an excipient or a mixture of two or more excipients that provide the physical and/or chemical stability of the active agent. Stabilizers include amino acids, for example, but are not limited to, arginine, histidine, glycine, lysine, glutamine, proline; surfactants, for example, but are not limited to, polysorbate 20 (trade name: Tween® 20), polysorbate 80 (trade name: Tween® 80), polyethylene-polypropylene glycol and copolymers thereof (trade names: Poloxamer, Pluronic, sodium dodecyl sulfate (SDS); antioxidants, for example, but are not limited to, methionine, acetylcysteine, ascorbic acid, monothioglycerol, sulfurous acid salts, etc.; chelating agents, for example, but are not limited to, ethylenediaminetetraacetic acid (EDTA), diethylenetriaminepentaacetic acid (DTPA), sodium citrate, etc.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition of the invention can be manufactured, packaged, or widely sold in the form of a single unit dose or a plurality of single unit doses in the form of a ready formulation. The term "single unit dose" as used herein refers to discrete quantity of a pharmaceutical composition containing a predetermined quantity of an active ingredient. The quantity of the active ingredient typically equals the dose of the active ingredient to be administered in a subject, or a convenient portion of such dose, for example, half or a third of such dose.

Pharmaceutical compositions according to the present invention are typically suitable for parenteral administration as sterile formulations intended for administration in a human body through the breach in skin or mucosal barriers, bypassing the gastrointestinal tract by virtue of injection, infusion and implantation. For example, parenteral administration includes, inter alia, subcutaneous, intraperitoneal, intramuscular, intrasternal, intravenous, intraarterial, intrathecal, intraventricular, intraurethral, intracranial, intrasynovial, transdermal injection or infusions; and kidney dialytic infusion techniques. Intra-tumor delivery, for example, intra-tumor injection, can also be employed. Regional perfusion is also provided. Preferred embodiments of the invention include intravenous and subcutaneous routes. Any method for administering peptides or proteins, which is accepted in the art, may be suitably employed for a monoclonal antibody that specifically binds to GITR according to the invention.

Injectable formulations may be prepared, packaged, or sold, without limitation, in unit dosage form, such as in ampoules, vials, in plastic containers, pre-filled syringes, autoinjection devices. Formulations for parenteral administration include, inter alia, suspensions, solutions, emulsions in oily or aqueous bases, pastes, and the like.

In another embodiment, the invention provides a composition for parenteral administration comprising a pharmaceutical composition which is provided in dry (i.e. powder or granular) form for reconstitution with a suitable base (e.g. sterile pyrogen-free water) prior to administration. Such formulation may be prepared by, for example, lyophilisation process, which is known in the art as freeze drying, and which involves freezing a product followed by removal of solvent from frozen material.

A monoclonal antibody that specifically binds to GITR according to the invention can also be administered intranasally or by inhalation, either alone, as a mixture with a suitable pharmaceutically acceptable excipient from an inhaler, such as a pressurised aerosol container, pump, spray, atomiser, or nebuliser, wherein a suitable propellant is used or not used, or as nasal drops, or spray.

Dosage forms for parenteral administration may be formulated to be immediate or modified release. Modified release formulations include delayed-, sustained-, pulsed-, controlled-, targeted and programmed release.

Therapeutic Use of a Monoclonal Antibody that Specifically Binds to GITR According to the Invention In one aspect, a monoclonal antibody that specifically binds to GITR according to the invention is useful in the treatment of disorders that are associated with (mediated by) GITR activity.

In one aspect, the subject of treatment, or patient, is a mammal, preferably a human subject. Said subject may be either male or female, of any age.

In some embodiments, said monoclonal antibody or antigen-binding fragment thereof that specifically binds to GITR is used for treating a disease or disorder mediated by GITR, where the disease or disorder is selected from the group comprising: cervical cancer, head and neck cancer, stomach cancer, breast cancer, renal cell cancer, CRC (colorectal cancer), (OC) ovarian cancer, NSCLC (non-small cell lung cancer).

In the case of a tumor (for example, cancer), the therapeutically effective amount of an antibody or fragment thereof (for example, an antibody or fragment thereof that specifically binds to GITR) may reduce the number of cancer cells; reduce the initial tumor size; inhibit (i.e., slow to some extent and preferably stop) cancer cell infiltration into peripheral organs; inhibit (i.e., slow to some extent and preferably stop) tumor metastasis; inhibit to some extent tumor growth; and/or relieve to some extent one or more of the symptoms associated with the disorder. The antibody or fragment thereof may to some extent prevent growth and/or kill existing cancer cells, it may be cytostatic and/or cytotoxic. For cancer therapy, in vivo efficacy can, for example, be measured by assessing survival, time to tumor progression (TTP), tumor response rate to treatment (RR), duration of response and/or quality of life.

As used herein, the terms "co-administration", "co-administered" and "in combination with", referring to a monoclonal antibody that specifically binds to GITR and one or more different therapeutic agents, are intended to mean, refer to or include the following:

1) simultaneous administration of such combination of a monoclonal antibody that specifically binds to GITR according to the invention and therapeutic agent to a patient in need of treatment, when such components are formulated together into a single dosage form which releases said components at substantially the same time to said patient, 2) simultaneous administration of such combination of a monoclonal antibody that specifically binds to GITR according to the invention and therapeutic agent to a patient in need of treatment, when such components are formulated apart from each other into separate dosage forms which are taken at substantially the same time by said patient, whereupon said components are released at substantially the same time to said patient, 3) sequential administration of such combination of a monoclonal antibody that specifically binds to GITR according to the invention and therapeutic agent to a patient in need of treatment, when such components are formulated apart from each other into separate dosage forms which are taken at consecutive times by said patient with a significant time interval between each administration, whereupon said components are released at substantially different times to said patient; and 4) sequential administration of such combination of a monoclonal antibody that specifically binds to GITR according to the invention and therapeutic agent to a patient in need of treatment, when such components are formulated together into a single dosage form which releases said components in a controlled manner, whereupon they are concurrently, consecutively, or jointly released at the same and/or different times to said patient, where each portion may be administered by either the same or different routes.

A monoclonal antibody that specifically binds to GITR according to the invention can be administered without further therapeutic treatment, i.e., as an independent therapy. Furthermore, treatment by a monoclonal antibody that specifically binds to GITR according to the invention may comprise at least one additional therapeutic treatment (combination therapy). In some embodiments of the invention, a monoclonal antibody that specifically binds to CD20 may be administered jointly or formulated with another medication/preparation for the treatment of a cancer.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound used to treat a malignant tumor. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g. bullatacin and bullatacinone); delta-9-tetrahydrocannabinol (dronabinol MARINOL®); beta-lapachone; lapachol; colchicines; betulinic acid; camptothecin (including the synthetic analogue topotecan (HYCAMTIN®), CPT-11

(irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (e.g. cryptophycin 1 and cryptophycin 8); dolastatin; duocarmycin (including the synthetic analogues, KW-2189 and CB1-TM1); eleutherobin; pancratistatin; sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g. calicheamicin, e.g. calicheamicin gamma II and calicheamicin omega II (see, e.g. Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXOL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamideglycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (e.g. T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g. paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®), FILDESIN®), and vinorelbine (NAVELBINE®); etoposide (VP16); ifosfamide; mitoxantrone; leucovorin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN®); bisphosphonates such asclodronate (for example, BONEFOS® or OSTAC®), etidronate (DIDROCAL®), NE-58095, zoledronic acid/zoledronate (ZOMETA®), alendronate (FOSAMAJX®), pamidronate (AREDIA®), tiludronate (SKELID®), or risedronate (ACTONEL®); troxacitabine (1,3-dioxolane nucleoside cytosine analog); antisense oligonucleotides, particularly those that inhibit expression of genes in signaling pathways implicated in aberrant cell proliferation, such as for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g. LURTOTECAN®); rmRH (e.g. ABARELIX®); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE®); CCI-779; tipifarnib (Rl 1577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate or inhibit hormone action on tumors, such as anti-estrogens with mixed agonist/antagonist profile, including, tamoxifen (NOLVADEX®), 4-hydroxytamoxifen, toremifene (FARESTON®), idoxifene, droloxifene, raloxifene (EVTSTA®), trioxifene, keoxifene, and selective estrogen receptor modulators (SERMs), such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors, such as formestane and exemestane (AROMASIN®), and nonsteroidal aromatase inhibitors, such as anastrazole (AREVIIDEX®), letrozole (FEMARA®) and aminoglutethimide, and other aromatase inhibitors including vorozole (RIVISOR®), megestrol acetate (MEGASE®), fadrozole, imidazole; lutenizing hormone-releasing hormone agonists, including leuprolide (LUPRON® and ELIGARD®), goserelin, buserelin, and tripterelin; sex steroids, including progestins, such as megestrol acetate and medroxyprogesterone acetate, estrogens, such as diethylstilbestrol and premarin, and androgens/retinoids such as fluoxymesterone, all transretinoic acid and fenretinide; onapristone; anti-progesterones; estrogen receptor down-regulators (ERDs); anti-androgens, such as flutamide, nilutamide and bicalutamide; testolactone; and pharmaceutically acceptable salts, acids or derivatives of any of the above; as well as combinations of two or more of the above.

Other therapeutic agents that can be used in combination with an antibody that specifically binds to GITR according to the invention can be inhibitors of growth factor function, for example, such inhibitors include growth factor antibodies and growth factor receptor antibodies (for example, the anti-erbB2 antibody trastuzumab [Herceptin], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp11-29); antiangiogenic agents such as those which inhibit the effects of vascular endothelial growth factor, [for example, the anti-vascular endothelial cell growth factor antibody bevacizumab (Avastin)], anti-vascular endothelial growth factor receptor antibodies, such as anti-KDR antibodies and anti-flt1 antibodies; antisense therapies, for example those which are directed to the targets listed above, such as ISIS 2503, an anti-ras antisense or G3139 (Genasense), an anti bcl2 antisense; gene therapy approaches, including, for example, approaches to replace aberrant genes, such as aberrant p53 or aberrant BRCA1 or BRCA2, GDEPT (gene-directed enzyme pro-drug therapy), approaches such as those using cytosine deaminase, thymidine kinase or a bacterial nitroreductase enzyme and approaches to increase patient tolerance to chemotherapy or radiotherapy, such as multi-drug resistance gene therapy; immunotherapy approaches, including, for example, treatment with Alemtuzumab (campath-1H), a monoclonal antibody directed at CD52, or treatment with antibodies directed at CD22, ex vivo and in vivo approaches to increase the immunogenicity of patient tumour cells, transfection with cytokines such as interleukin 2, interleukin 4 or granulocyte macrophage colony stimulating factor, approaches to decrease T cell anergy, such as treatment with monoclonal antibodies inhibiting CTLA-4 function, approaches using transfected immune cells, such as cytokine transfected dendritic cells, approaches using cytokine transfected tumour cell lines and approaches using anti idiotypic antibodies, adoptive T cells transfer using T cells that have been non-specifically activated or targeted to a specific antigen of interest ex vivo; inhibitors of protein degradation, such as proteasome inhibitor, such as Velcade (bortezomib); biotherapeutic therapeutic approaches, for example, those which use peptides or proteins (such as antibodies or soluble external receptor domain constructions), which either sequester receptor ligands, block ligand binding to receptor or decrease receptor signalling (for example, due to enhanced receptor degradation or lowered expression levels).

Other therapeutic agent that can be used in combination with an antibody that specifically binds to GITR according to the invention can be an antibody selected from the group comprising: anti-PD1 antibodies, anti-PD-L1 antibodies, anti-CTLA4 antibodies, anti-4-1BB antibodies, anti-OX40 antibodies or combinations thereof.

Other therapeutic agent that can be used in combination with an antibody that specifically binds to GITR according to the invention can be a therapeutically active antitumour compound selected from the group of activators of innate or adaptive immunity.

It is meant that a monoclonal antibody that specifically binds to GITR according the invention may be used in the methods of treatment as described above, may be used in the treatment as described above, and/or may be used in the manufacture of a medication for treatment as described above.

Doses and Routes of Administration

A monoclonal antibody that specifically binds to GITR according to the invention will be administered in an amount that is effective in treatment of the condition in question, i.e. in doses and during the periods of time required to achieve the desired result. A therapeutically effective amount may vary according to factors such as the particular condition being treated, the age, sex and weight of the patient, and whether the monoclonal antibody that specifically binds to GITR is being administered as a stand-alone treatment or in combination with one or more additional drugs or treatments.

Dosage regimens may be adjusted to provide the optimum response. For example, a single bolus may be administered, several divided doses may be administered over time or the dose may be proportionally reduced or increased as indicated by the exigencies of the therapeutic situation. It is especially advantageous to formulate parenteral compositions in a unit dosage form for ease of administration and uniformity of dosage. A unit dosage form as used herein is intended to refer to physically discrete units suited as unitary dosages for patients/subjects to be treated; each unit contains a predetermined quantity of active compound calculated to produce the desired therapeutic effect in association with the desired pharmaceutical carrier. Specification for the unit dosage forms of the invention is typically dictated by and directly dependent on (a) the unique characteristics of a chemotherapeutic agent and particular therapeutic or prophylactic effect to be achieved, and (b) the limitations inherent in the art of compounding such an active compound for the treatment of sensitivity in the subjects.

Thus, a skilled artisan would appreciate, based upon the disclosure provided herein, that the doses and dosage regimen are adjusted in accordance with methods well-known in the therapeutic arts. That is, the maximum tolerable dose can be readily established, and the effective amount providing a detectable therapeutic effect to a patient may also be determined, as can the temporal requirements for administering each agent to provide a detectable therapeutic effect to a patient. Thus, while certain dose and administration regimens are exemplified herein, these examples in no way limit the doses and administration regimen that may be provided to a patient in practicing the embodiments of the invention.

It is to be noted that dosage values may vary with the type and severity of the condition to be alleviated, and may include single or multiple doses. Furthermore, it is to be understood that for any particular subject, specific dosage regimens should be adjusted over time according to the individual need and the judgment of a medical professional administering or supervising the administration of the compositions, and that dosage ranges set forth herein are exemplary only and are not intended to limit the scope or practice of the claimed compositions. Further, the dosage regimen with the compositions of this invention may be based on a variety of factors, including the type of disease, the age, weight, sex, medical condition of the patient, the severity of the condition, the route of administration, and the particular monoclonal antibody that specifically binds to GITR employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the person skilled in the art. Methods for determining appropriate dosages and regimens are well-known in the art and would be understood by a skilled artisan once provided the ideas disclosed herein.

Examples of suitable administration methods are provided above.

It is believed that a suitable dose of a monoclonal antibody that specifically binds to GITR according to the invention will be in the range of 0.1-200 mg/kg, preferably 0.1-100 mg/kg, including about 0.5-50 mg/kg, for example about 1-20 mg/kg. A monoclonal antibody that specifically binds to GITR may be administered, e.g. in a dose of at least 0.25 mg/kg, such as at least 0.5 mg/kg, including at least 1 mg/kg, e.g. at least 1.5 mg/kg, such as at least 2 mg/kg, e.g. at least 3 mg/kg, including at least 4 mg/kg, e.g. at least 5 mg/kg; and for example up to a maximum of 50 mg/kg, including up to a maximum of 30 mg/kg, e.g. up to a maximum of 20 mg/kg, including up to a maximum of 15 mg/kg. The administration will typically be repeated in appropriate time intervals, such as once a week, once every two weeks, once every three weeks or once every four weeks, and for as long as deemed appropriate by a responsible physician, who may, in some cases, increase or reduce the dose if necessary.

Diagnostic Use and Compositions

A monoclonal antibody that specifically binds to GITR according to the invention is also used in diagnostic processes (e.g. in vitro, ex vivo). For example, the present monoclonal antibody that specifically binds to GITR according to the invention can be used for detecting or measuring the level of GITR in samples obtained from a patient (e.g. tissue sample or a sample of body fluid, such as an inflammatory exudate, blood, serum, intestinal fluid, saliva or urine). Suitable methods for detection and measurement include immunoassays, such as flow cytometry, enzyme-linked immunosorbent assay (ELISA), chemiluminescent assay, radioimmunoassay, and immunohistology. The invention further includes kits, for example, diagnostic kits comprising a monoclonal antibody that specifically binds to GITR described herein.

EXAMPLES

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the essence and scope of the appended embodiments.

Materials and General Methods

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered according to EU numbering (Edelman, G. M., et al., Proc. Natl. Acad. Sci. Natl. Acad. Sci. USA 63 (1969) 78-85; Kabat, E. A., et al., Sequences of Proteins of Immunological Interest, 5th ed., Public Health Service, National Institutes of Health, Bethesda, MD, (1991).

Recombinant DNA Techniques

Standard methods were used to manipulate DNA as described in Sambrook, J. et al, Molecular cloning: A laboratory manual; Cold Spring Harbor Laboratory Press, Cold Spring Harbor, New York, 1989. The molecular biological reagents were used according to the manufacturer protocols.

Gene Synthesis

Desired gene segments were prepared from oligonucleotides made by chemical synthesis. The gene segments of 300-4000 kb long, which were flanked by singular restriction sites, were assembled by annealing and ligation of oligonucleotides including PCR amplification and subsequently cloned via the indicated restriction sites. The DNA sequences of the subcloned gene fragments were confirmed by DNA sequencing.

DNA Sequence Determination

DNA sequences were determined by Sanger sequencing.

DNA and Protein Sequence Analysis and Sequence Data Management

The Infomax's Vector NT1 Advance suite version 8.0 was used for sequence creation, mapping, analysis, annotation and illustration.

Expression Vectors

For the expression of the described antibodies and antigens, variants of expression plasmids intended for expression in prokaryotic cells (*E. coli*), transient expression in eukaryotic cells (e.g. in CHO cells) were applied. Beside the antibody expression cassette the vectors comprised: an origin of replication which allows replication of said plasmid in *E. coli*, genes which confer resistance in *E. coli* to various antibiotics (e.g. to ampicillin and kanamycin).

The fusion genes comprising the described antibody chains as described below were generated by PCR and/or gene synthesis and assembled with known recombinant methods and techniques by connection of the according nucleic acid segments, e.g. using unique restriction sites in the corresponding vectors. The subcloned nucleic acid sequences were verified by DNA sequencing. For transient transfections, larger quantities of the plasmids were prepared by plasmid preparation from transformed *E. coli* cultures.

Example 1

Figure 2:
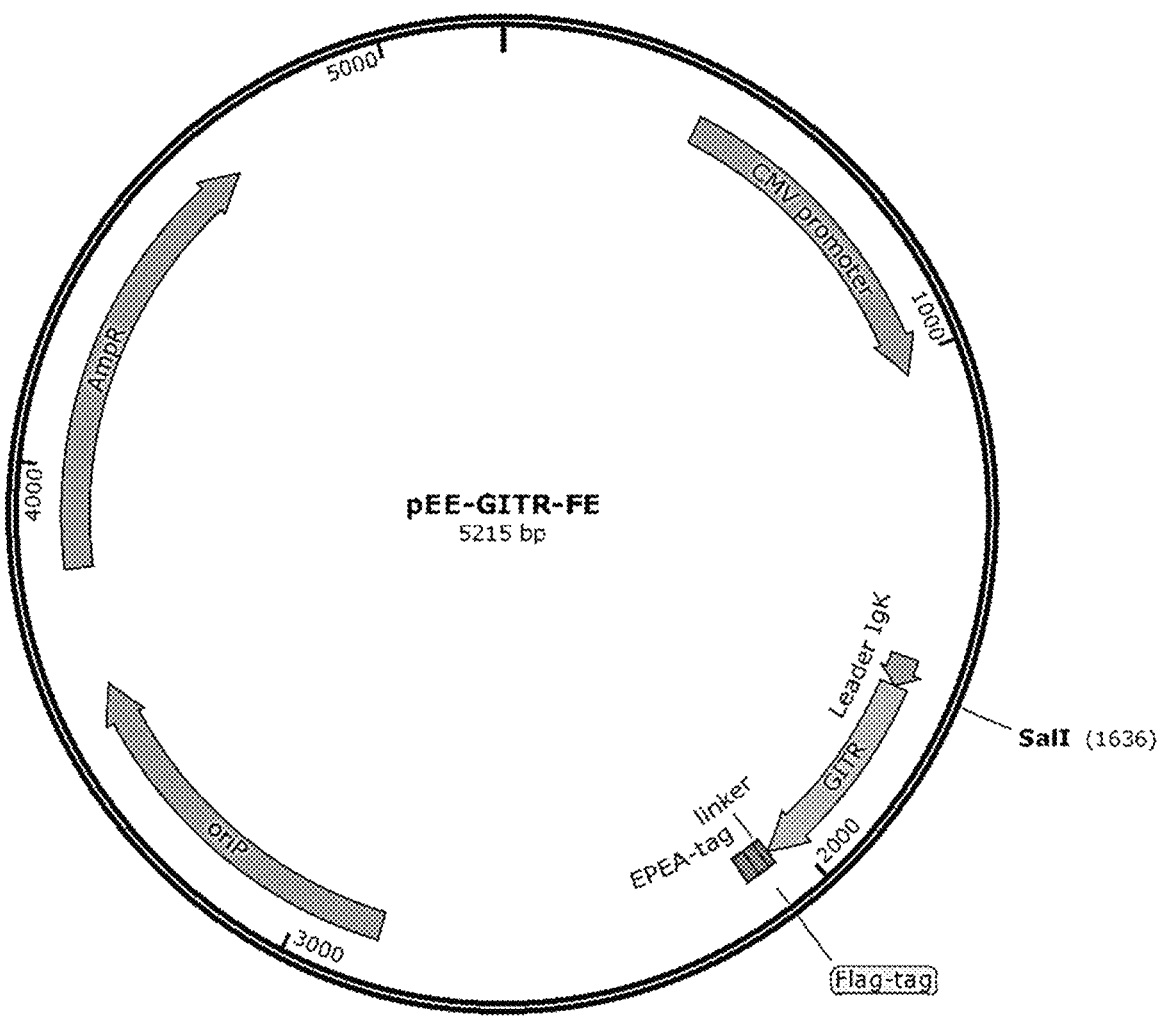
FIG. 2. Plasmid for protein production pEE-GITR-Fc.
Figure 3:
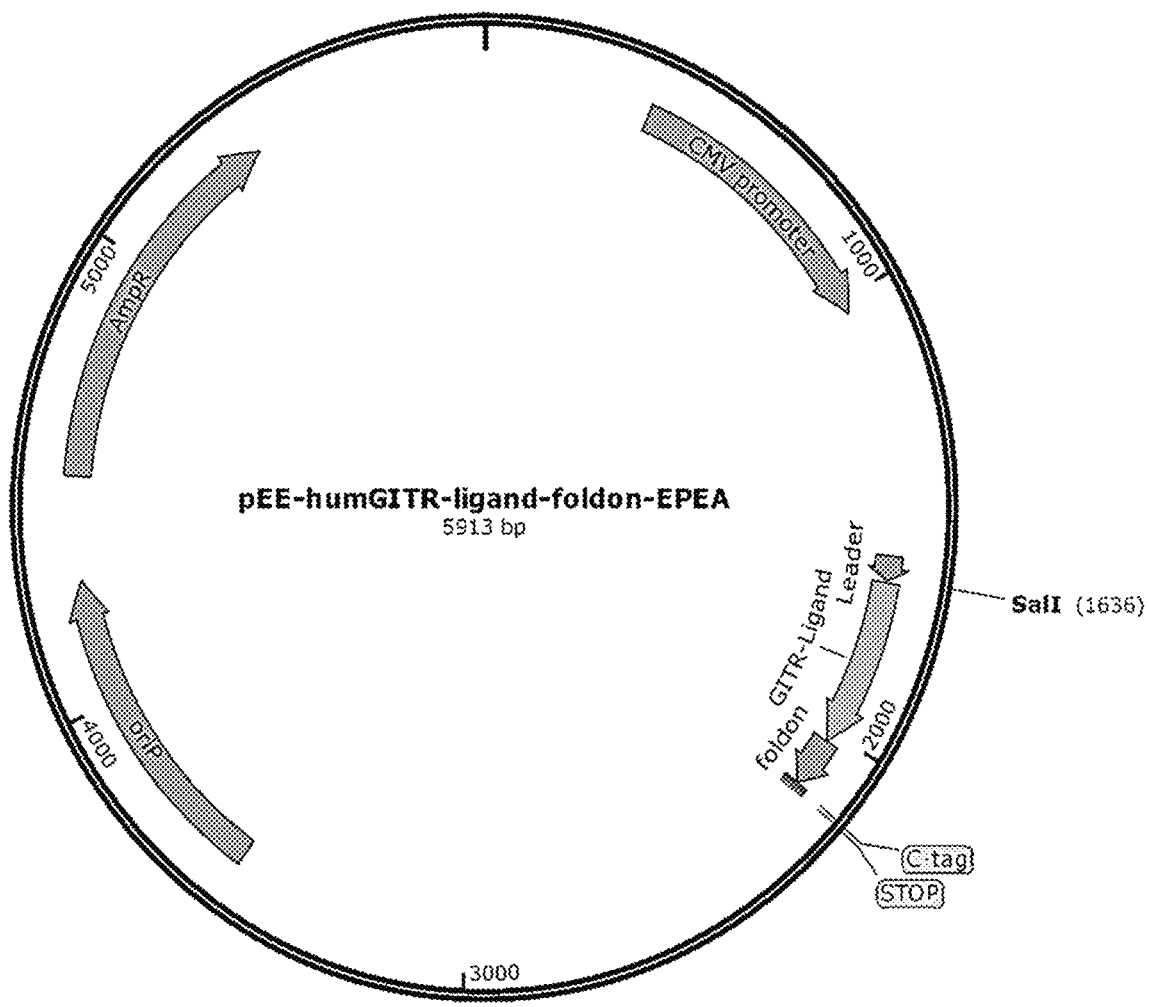
FIG. 3. Map of plasmid pEE-humGITR-ligand-foldon-EPEA.

Production of Recombinant Antigens and Antibodies in Suspension Culture of Mammalian Cells To prepare recombinant antigens based on the sequence of extracellular portion of human GITR and orthologs, we generated a number of constructs comprising the antigen extracellular domain human GITR, mcyGITR *Macaca mulatta* and musGITR *Mus musculus*. Gene sequences were synthesized by PCR from matrix, encoding full-length human GITR antigen from the plasmid vector RDC0359 and assembled from synthetic oligonucleotides for GITR ortholog genes. GITR gene sequence was cloned into plasmid for protein production in Fc IgG1 *Lama glama*-tagged mammalian cells (FIG. 1) at SalI/NotI restriction sites. Furthermore, antigen sequence is separated from Fc by protease labile site of TEV protease; the site was also used to cleave Fc fragment by treatment with TEV protease and to obtain a tagless version of antigen. The sequence was also cloned into plasmid containing FLAG-EPEA-tag (C-tag GE Healthcare) at C-terminus of protein (FIG. 2) at SalI/NotI restriction sites. Furthermore, recombinant human GITR-ligand (GITRL) was cloned in a similar fashion into plasmid containing homotrimeric foldon [1] domain and EPEA-tag at C-terminus of GITRL (FIG. 3). The required quantities of plasmids were produced in *E. Coli* cells and purified using Maxiprep Qiagen kit.

Antibodies and antigens were generated in established cell line obtained from Chinese hamster ovary cells (CHO-K1) according to published protocols [Biotechnol Bioeng. 2005 Sep. 20; 91(6):670-677, Liao Metal., 2004; Biotechnol Lett. 2006 June; 28(11):843-848; Biotechnol Bioeng. 2003

Nov. 5; 84(3):332-342]. Cells constitutively expressing the EBNA1 (Epstein-Barr virus nuclear antigen 1) protein gene were used. Suspension culture was conducted in flasks on orbital shaker using serum-free media from Life Technologies Corporation and in accordance with manufacturer's guidelines. For transient expression, cells at a concentration of $2*10^6$/ml were transfected by means of linear polyethyleneimine (PEI MAX, Polysciences). DNA/PEI ratio was 1:3-1:10. In 5-7 days after transfection, cell culture was centrifuged at 2000 g for 20 min and filtered through 0.22 μm filter. Target proteins were isolated from culture liquid by affine HPLC.

Recombinant GITR and GITRL proteins comprising an EPEA-tag (glutamic acid-proline-glutamic acid-alanine) at protein C-terminus were isolated and purified from culture liquid using CaptureSelect C-tag Affinity Matrix sorbent. The culture liquid was passed through a chromatographic column pre-filled with 5 ml of C-tag sorbent, the column was then washed with 25 ml of PBS to remove non-specifically binding components. Bound antigen was eluted under mild conditions using 20 mM Tris, 2M MgCl2 pH7.0-7.4. Then protein was then dialyzed into PBS (pH 7.4) using a semi-permeable dialysis membrane, filtered (0.22 μm), transferred into tubes and stored at −70° C.

Recombinant GITR-TEV-Fc antigen was isolated and purified from culture liquid on Protein A column for affine HPLC. Cleared culture liquid was passed through 5 ml HiTrap rProtein A Sepharose FF column (GE Healthcare) equilibrated with phosphate buffered saline (PBS, pH 7.4). Then, the column was washed with 5 column volumes of PBS to remove non-specifically binding components. Bound antigen was eluted using 0.1 M glycine buffer (pH 3). The principal protein elution peak was collected and brought to neutral pH with 1 M Tris buffer (pH 8). All stages were conducted under 110 cm/h flow rate. Protein was then dialyzed into PBS (pH 7.4) using SnakeSkin Dialysis Tubing technique, filtered (0.22 μm), transferred into tubes and stored at −70° C.

Figure 4:
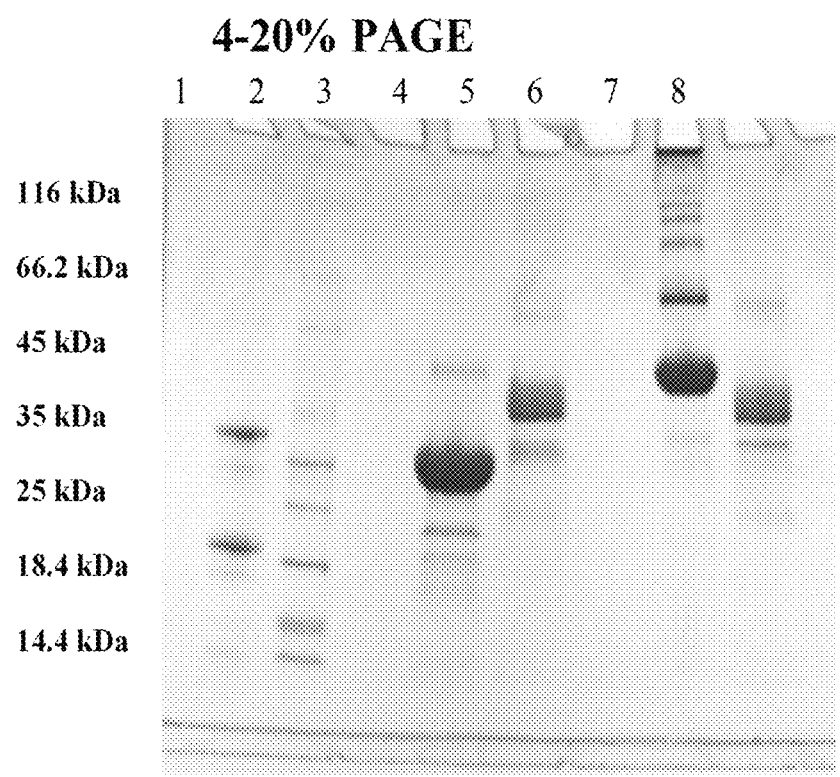
FIG. 4. SDS-PAGE (4-20% gel)
1. Actemra® 2.5 mg
2. Fermentas unstained PW marker
3. —
4. GITR-TEV-Fc-lama+β-ME 10 ml
5. Angiopoetin 2-H6F+β-ME 10 ml
6. —
7. GITR-TEV-Fc-lama −β-ME 10 ml
8. Angiopoetin 2-H6F−β-ME 10 ml FIG. 5. SDS gel electrophoresis
1. Fermentas unstained PW marker
2. —
3. hGITR ligand–EPEA medium before purification 5 ml
4. hGITR ligand–EPEA medium after purification 5 ml
5. hGITR ligand–EPEA FIG. 6. Scheme of synthesis of human naive combinatorial library.
Figure 5:
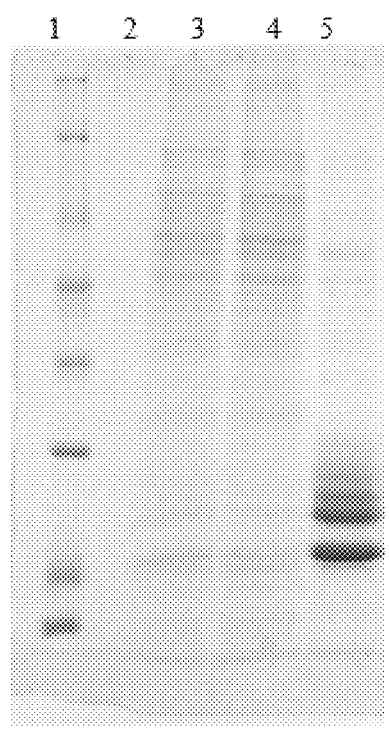

All recombinant IgG antibodies were purified on a 1 ml Hi Trap rProteinA FF column (GE Healthcare) in accordance with the procedure aforementioned for antigens. Purity of resulting protein solution was evaluated by SDS gel electrophoresis (examples are shown in FIGS. 4 and 5).

Example 2

Construction of a Naive Human Antibody Fab-Library MeganLib™

Total RNA of B lymphocytes from blood samples from more than one thousand individual human donors was isolated using RNeasy Mini Kit according to the suggested protocol (QIAGEN). RNA concentration assay was performed using Nanovue kit (GE Healthcare), the quality of isolated RNA was tested by means of 1.5% agarose gel electrophoresis.

Reverse transcription reaction was conducted using MMLV RT kit (Evrogen) according to the recommended protocol using MMuLV reverse transcriptase and random hexamer oligonucleotides as primers.

Reverse transcription products were used as a matrix in a two-stage polymerase chain reaction to obtain variable domain genes flanked by restriction sites; reaction was performed using oligonucleotide kit according to protocols by [J Biol Chem. 1999 Jun. 25; 274(26): 18218-30].

Figure 6:
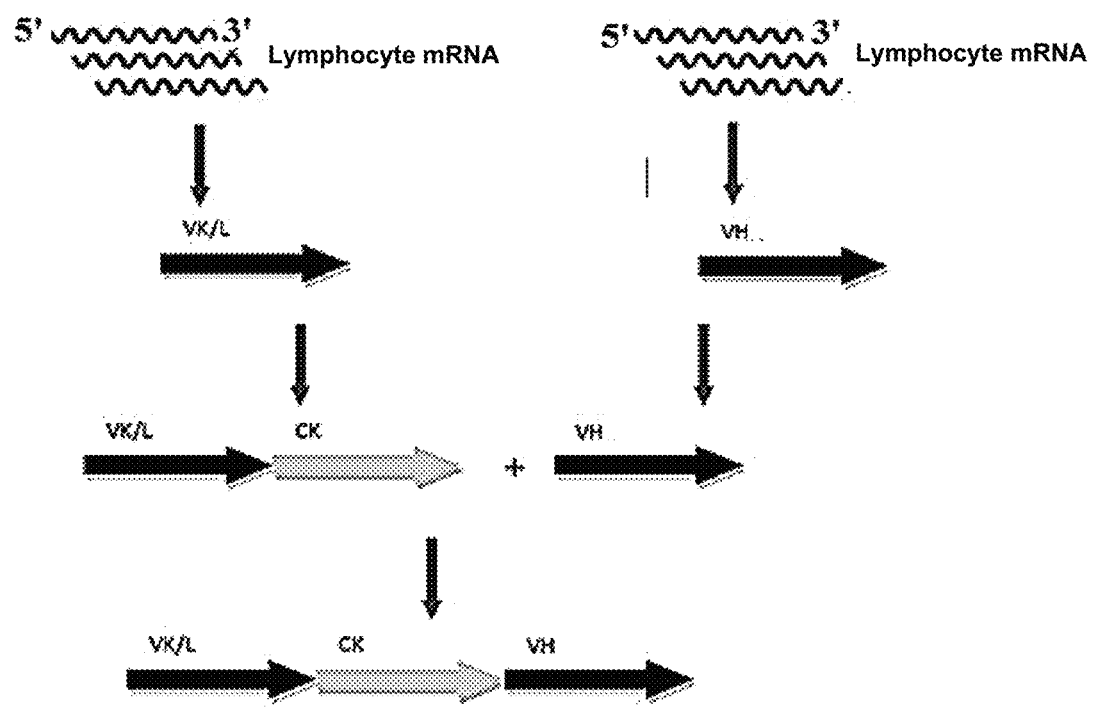
Figure 7:
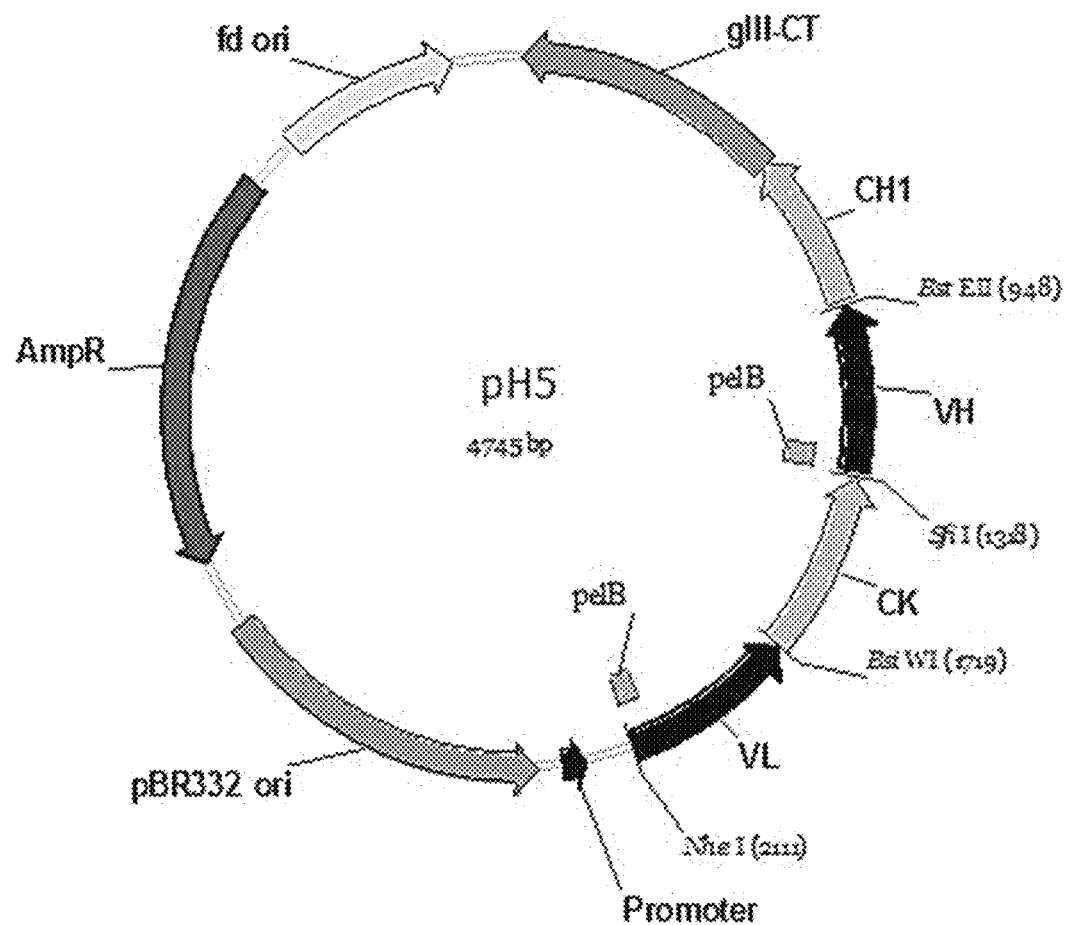
FIG. 7. Map of phagemid pH5 used for cloning Fab phage display libraries.

The resulting DNA preparation VL-CK-VH (FIG. 6) was treated with NheI/Eco91I restriction endonucleases and ligated into the original phagemid pH5 (FIG. 7). Ligation products were transformed into SS320 strain electrocompetent cells prepared in accordance with protocols [Methods Enzymol. 2000; 328: 333-63.]. Repertoire of combinatorial phage Fab display library MeganLib™ was $10^{11}$ transformants. Fab library phage products were prepared in accordance with the earlier described procedure [J Mol Biol. 1991 Dec. 5; 222(3): 581-97].

Example 3

Construction of Immune Fab Libraries of Hybrid Llama-Human Antibodies (CHARM).

Total RNA of B lymphocytes from individual blood samples of *Lama Glama* immunized with recombinant GITR antigens, which exhibited maximum specific serum titer, was isolated using RNeasy Mini Kit according to the suggested protocol (QIAGEN). RNA concentration assay was performed using Nanovue kit (GE Healthcare), the quality of isolated RNA was tested by means of 1.5% agarose gel electrophoresis.

Reverse transcription reaction was conducted using MMLV RT kit (Evrogen) according to the recommended protocol using MMuLV reverse transcriptase and random hexamer oligonucleotides as primers.

Reverse transcription products were used as a matrix in a two-stage polymerase chain reaction to obtain variable domain genes flanked by restriction sites; reaction was performed using oligonucleotide kit according to protocols by [J Biol Chem. 1999 Jun. 25; 274(26): 18218-30].

The resulting DNA preparation VL-CK-VH (FIG. 6) was treated with NheI/Eco91I restriction endonucleases and ligated into the original phagemid pH5 (FIG. 7). Ligation products were transformed into SS320 strain electrocompetent cells prepared in accordance with protocols [Methods Enzymol. 2000; 328: 333-63.]. Repertoire of combinatorial phage Fab display library MeganLib™ was $10^{11}$ transformants. Fab library phage products were prepared in accordance with the earlier described procedure [J Mol Biol. 1991 Dec. 5; 222 (3): 581-97]. Table 1 shows summary table of immune library products.

TABLE 1

| Item no. | Code | Name | Library variant/ beionging to species | Repertoire, CFU | Concentratin, units/ml |
|---|---|---|---|---|---|
| 1 | Lib1-60 | BCD166_ ILKalifVHH.bph | Kalif llama immune monodomain library under the GITR project (plasmid pSCK) | $5 \times 10E^8$ | $2 \times 10E^{13}$ |

TABLE 1-continued

| Item no. | Code | Name | Library variant/ belonging to species | Repertoire, CFU | Concentratin, units/ml |
|---|---|---|---|---|---|
| 2 | Lib1-61 | BCD166_ILBlackVHH.bph | Black llama immune monodomain library under the GITR project (plasmid pSCK) | $5 \times 10E^8$ | $2 \times 10E^{13}$ |
| 3 | Lib1-62 | BCD166_Ch_L_VH_ILBlack.bph | Black llama λ-Fab Charm Lib under the GITR project (plasmid pH6) | $5 \times 10E^7$ | $4 \times 10E^{13}$ |
| 4 | Lib1-63 | BCD166_Ch_K_VH_ILBlack.bph | Black llama κ-Feb Charm Lib under the GITR project (plasmid pH6) | $5 \times 10E^7$ | $4 \times 10E^{13}$ |
| 5 | Lib1-64 | BCD166_Ch_L_VH_ILKalf.bph | Kalif llama λ-Fab Charm Lib under the GITR project (plasmid pH6) | $5 \times 10E^7$ | $3 \times 10E^{13}$ |
| 6 | Lib1-65 | BCD166_Ch_K_VH_ILKalif.bph | Kalif llama κ-Fab Charm Lib under the GITR project (plasmid pH6) | $5 \times 10E^7$ | $4.7 \times 10E^{13}$ |

Example 4

Selection of Phage Antibody Fab-Libraries

Specific anti-GITR human phage Fab antibodies were obtained from the combinatorial phage Fab display library MeganLib™ and immune CHARM libraries described in Examples 2 and 3. Selection was performed on recombinant human G1CR antigens by phage display [Nat Biotechnol. 1996 March; 14(3):309-14; J Mol Biol. 1991 Dec. 5; 222 (3): 581-97].

Selection of immune phage libraries was performed on EIA/RIA Tube High Binding 5 ml immunotube. Antigen (0.5 ml 2 µg/ml) was sorbed in carbonate buffer (0.1 M NaHCO$_3$, pH 9.5) overnight at +4 C. Tubes were then washed with PBST (10 mM phosphate buffered saline pH 7.3-7.5, 137 mM NaCl and 2.7 mM KCl, 0.1% Polysorbate 20), and total volume (5 ml) of 0.5% milk powder in PBST was added for blocking. The blocking was alternated from round to round; for example, if 0.5% milk in PBST was used in the 1st round, then 1% BSA in PBST was used in the 2nd one. Tubes were incubated for 1 h at room temperature on a shaker. Tubes were washed with PBST, and 2 ml/tube of blocking buffer and phage libraries were added thereto to a concentration of about $2*10^{12}$ phage particles per ml. We incubated them with phages for 1-2 hours at room temperature. In further rounds, we used 4 ml of phage supernatant from a previous round, which was pre-clarified in a centrifuge at 17,000 g for 10-15 minutes. Tubes were washed 20 times with PBST. Phages were eluted from surface of tubes with 0.5 ml of 0.1 M glycine buffer pH 2.2: glycine buffer was added to the tubes, and the solution was lightly stirred for 15 minutes at room temperature. Phage solution was then transferred to clean, non-sorbing tubes with 100 µl of 1M TrisHCl pH8.0 for neutralization. Tubes were kept in ice until the cells were infected.

After selection, M13 bacteriophage is cultured using *E. coli* TG1 strain as a host. Amplification is carried out by infecting the host strain culture with phages followed by growing for 12-15 hours.

After selection, 0.5-1 ml of phages was mixed with a cell culture (OD$_{600}$=0.3-0.4) and incubated for 1.5 hours at 37° C. Then, cells were spun down at 3,000-4,000 rpm for 10-15 minutes, resuspended in 1 ml of medium and plated on Petri dishes containing an antibiotic for selection (ampicillin). Colonies were grown in a thermostat at 30 C. After 12-15 hours, we calculated the number of colonies and cells were washed from dishes with 5-10 ml of LB medium. 100 µl of cell suspension was added to 20 ml of antibiotic medium (ampicillin). We increased density to OD600=0.35-0.5 by 37. K07 phage helper was added at 1 µl/10 ml of culture (1010 particles/ml) and incubated at 37 C for 1.5 hours without shaking. Then, an equal volume of medium with single-dose ampicillin (100 µg/ml) and double-dose kanamycin (40 µg/ml) and double-dose IPTG (0.2 mM) was added to the cell culture. The cell culture was loaded into a shaker, and phages were cultured for 4-5 hours at 30 C. The cell culture was centrifuged for 25-30 min at 17,000 g, supernatant was collected in tubes. The resulting supernatant was then used in the next round of selection, or phage was isolated by precipitation for further storage.

Phages were isolated by the following method: ⅙ of volume of solution comprising 20% of polyethyleneglycol and 2.5 M sodium chloride was added to supernatant and stirred intensively. The solution was incubated in ice for at least 3 hours. The solution was then centrifuged for 10 minutes at 8,000 g, the resulting precipitate comprising phages was diluted in 1 ml of TBS buffer (Tris-borate buffer).

After 2-3 rounds, bacteriophages were isolated, we analyzed specific binding of polyclonal phage to human GITR, and non-specific antigens.

Example 5

Analysis of Polyclonal Phages from 2nd and 3rd Rounds of Selection.

After 3 rounds of selection of 2 naive MeganLib libraries and 6 immune libraries on target antigen, we examined specific and non-specific binding of polyclonal phages from 2nd and 3rd rounds using ELISA.

The target GITR antigen was sorbed overnight in a carbonate buffer (0.1 M NaHCO$_3$, pH 9.5) onto the plastic surface of the ELISA plate to analyze for the presence of specifically binding phages (2 µg/ml), or GCSF, hIL6R-Fc, interferon alfa-2b, Rituximab (2 µg/ml) to analyze for non-specifically binding phages. Plates were then washed with PBST (10 mM phosphate buffered saline pH 7.3-7.5, 137 mM NaCl and 2.7 mM KCl, 0.1% Polysorbate 20), then 300 µl/well of 0.5% milk powder in PBST was added for blocking. The plates were incubated for 1 h at room temperature on a shaker. The plates were washed with PBST, and 50 µl/well of phage solutions from 2nd and 3rd rounds of selection diluted with blocking buffer at 1:2 to 1:256 was added to the plates. The plates were incubated for 1 h at room temperature on a shaker. The plates were washed with PBST, and coated with anti-M13 horseradish peroxidase conjugated antibody in blocking buffer. After 1 hour incubation, the plates were washed, 50 µl/well of reaction substrate (H2O2—0.02% and TMB) in acetate buffer pH 5.0 was added. The plates were incubated at room temperature in dark until a slight background appeared in the negative controls (but for not more than 20 minutes). The reaction was quenched by adding 25 µl/well of 10% H2SO4, OD in wells was measured at 450 nm.

The assay revealed specific (5× the background signal) binding of 1 human naive Fab library and 6 immune Fab CHARM libraries after 3rd round of selection on target antigen and absence of significant (less than 2× the background signal) non-specific binding.

Figure 8:
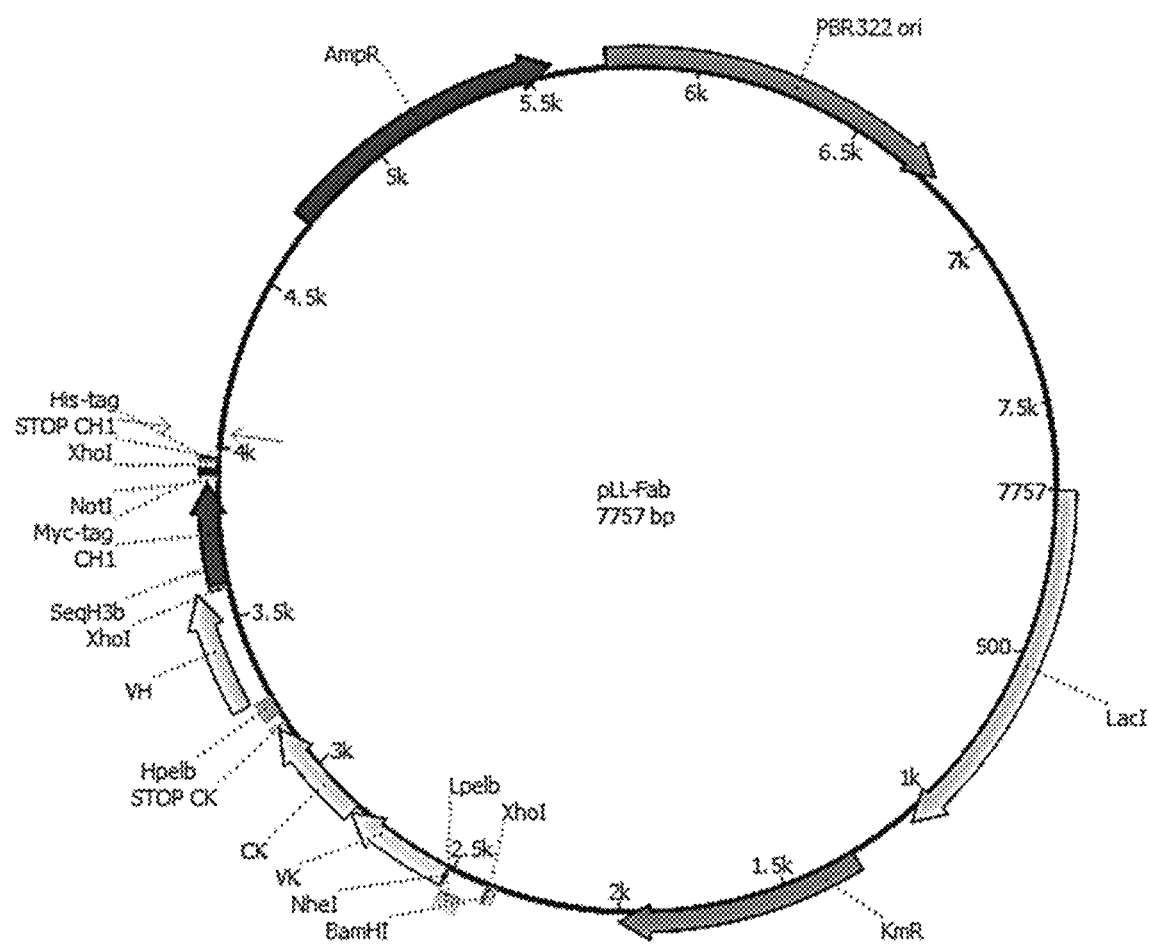
FIG. 8. Map of expression plasmid pLL for production of secreted Fabs.

The antibody variable domains genes from these libraries were recloned into expression vector pLL-Fab (FIG. 8) to produce a secretable soluble form of Fab in *E. coli* cells.

Example 6

Screening of Fabs that Specifically Bind Human GITR

ELISA was used to detect Fabs that specifically bind human GITR, which are secreted into the medium from monoclones produced in *E. coli* according to Example 5. Fab with a published sequence, Fab-gitr3215 (patent application), was used as a positive control. For specific binding assay, ELISA well plates (medium binding, Greiner bio one) were coated with 50 µl/well of GITR (0.2 µg/ml in 1× carbonate buffer), sealed and incubated overnight at 4° C. All further stages were performed in accordance with standard ELISA protocols using a high-performance automated platform based on robotic systems such as Genetix Qpix2xt (Molecular Devices) and Tecan Freedom EVO 200 (Tecan). Non-specific binding was blocked by adding a blocking buffer BB (200 µl 0.5% fat-free milk in PBS). Plates were incubated on a shaker for 1 h at room temperature. After washing with PBS-Tween®, each cell was coated with 50 µl of test Fab-containing cell supernatant mixed with the equal volume of BB. Plates were incubated on a shaker for 1 hour at room temperature; further, each plate well was 3 times washed with PBS-Tween® buffer. After washing, each well was coated (50 µl/well) with anti-human Fab HRP-conjugated secondary antibody (Pierce-ThermoScientific) in PBS-Tween® (1:5000). Plates were shaken on a rotation shaker (50 min at room temperature) and then 3 times washed with PBS-Tween® buffer as described above. Colorimetric signal was developed by adding TMB (50 µl/well) until saturation (average of 3-5 min); further color development was blocked by adding a stop solution (30 µl/well, 10% sulfuric acid). Color signal was measured at 450 nm using an appropriate Tecan-Sunrise plate reader (Tecan). Antibody binding level was proportional to color signal production. Clones, in which the color signal 5× exceeded the background signal and was comparable to that of the control antibody Fab-gitr3215, were examined by ELISA to detect non-specific binding.

Example 7

Non-Specific Binding Assay of Selected Fab—Other Antigen Interactions

ELISA was also employed to assay non-specific binding of Fab fragments in question to other antigens. The study was performed as described above, but IL6R-Fc, INFα2b, PCSK9-VG-FE, PD-1-Fc (2.5 µg/ml in 1× carbonate buffer) were used as immobilization antigens. GITR-TEV-Fc (0.2 µg/ml in 1× carbonate buffer) was used as a specific binding control. All further stages were conducted in accordance with the standard ELISA protocol using a high-performance automated platform based on robotic systems such as Genetix Qpix2xt (Molecular Devices) and Tecan Freedom EVO 200 (Tecan). Clones, in which the color signal of nonspecific binding did not exceed the background signal and had 5× lower values as compared to those of specific binding, were considered positive and their genes were sequenced for the determination of antibody variable domain gene sequence and determination of uniqueness. As a result of sequencing, we selected 30 unique sequences for conversion to a full-length IgG1 antibody format.

Example 8

Production of Recombinant Antibodies in Suspension Culture of Mammalian Cells

Figure 9:
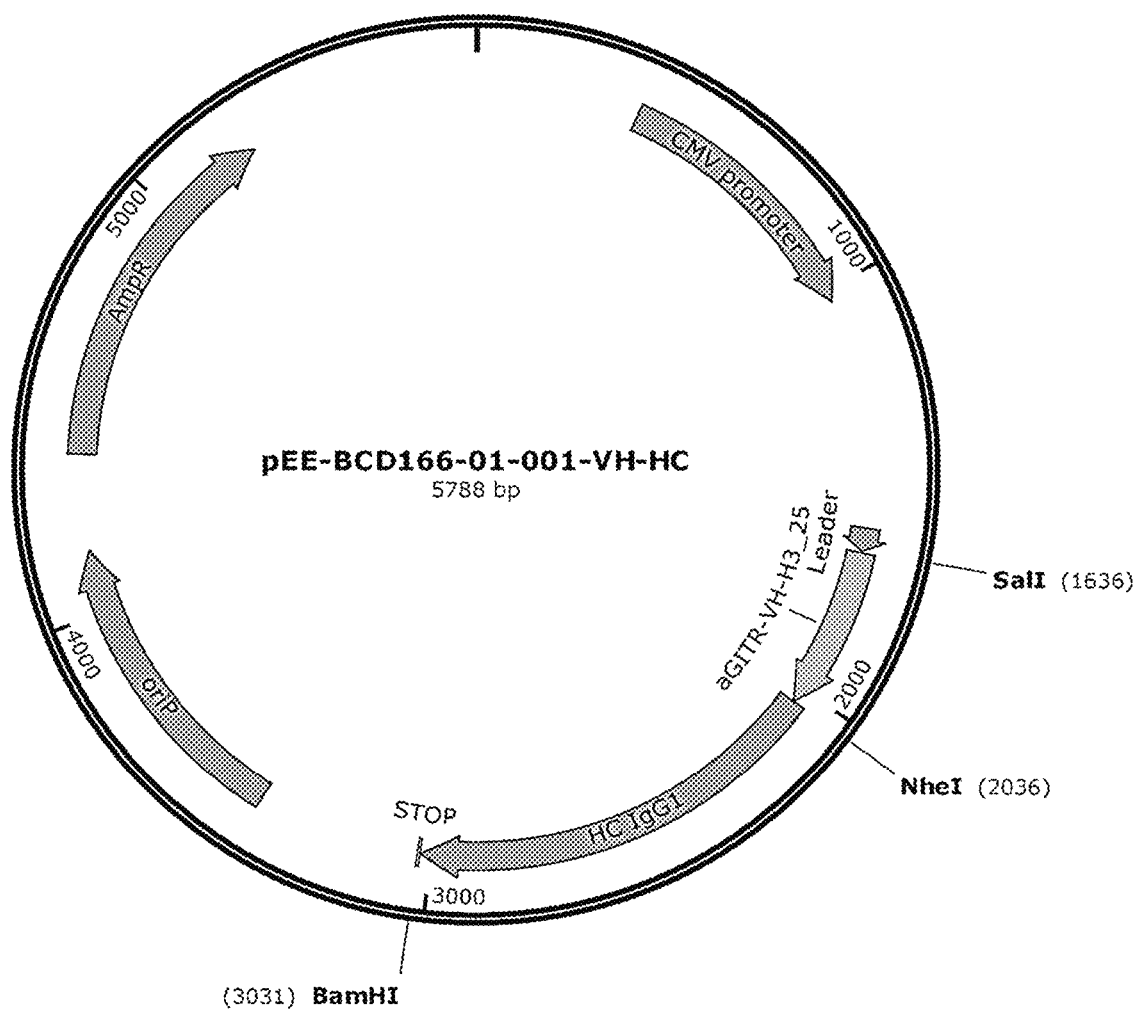
FIG. 9. Map of expression vector pEE-BCD166-01-001-VH-HC encoding the heavy chain of antibodies for transient antibody production in mammalian cells FIG. 10. Map of expression vector pEE-BCD166-01-001-VK-CK encoding the light chain of antibodies for transient antibody production in mammalian cells FIG. 11. SDS-PAGE in 12% GEL+β-ME
1. Actemra® 5 ml
2. Fermentas unstained PW marker
3. —
4. anti-GITR antibody lot #1161 medium before purification 5 ml 5. anti-GITR antibody lot #1161 medium after purification 5 ml
6. anti-GITR antibody lot #1161 5 ml
7. anti-GITR antibody lot #1162 5 ml
8. anti-GITR antibody lot #1163 5 ml
9. anti-GITR antibody lot #1164 5 ml
10. anti-GITR antibody lot #1165 5 ml
11. anti-GITR antibody lot #1166 medium before purification 5 ml
12. anti-GITR antibody lot #1166 medium after purification 5 ml
13. anti-GITR antibody lot #1166 5 ml
14. anti-GITR antibody lot #1167 5 ml FIG. 12. SDS-PAGE in 12% GEL+β-ME
1. Fermentas unstained PW marker
2. anti-GITR antibody lot #1208 medium before purification 10 ml
3. anti-GITR antibody lot #1208 medium after purification 10 ml
4. anti-GITR antibody lot #1208 5 ml
5. anti-GITR antibody lot #1209 5 ml
6. anti-GITR antibody lot #1210 5 ml
7. anti-GITR antibody lot #1211 5 ml
8. anti-GITR antibody lot #1212 5 ml
9. anti-GITR antibody lot #1213 5 ml
10. anti-GITR antibody lot #1214 medium before purification 10 ml
11. anti-GITR antibody lot #1214 medium after purification 10 ml
12. anti-GITR antibody lot #1214 5 ml FIG. 13. A graph showing the results of examination of specific agonist activity of anti-GITR monoclonal antibodies of lots 1161 (BCD166-01-01), 1210 BCD166-01-011) and 1213 BCD166-01-014) in a reporter cell line assay.
Figure 10:
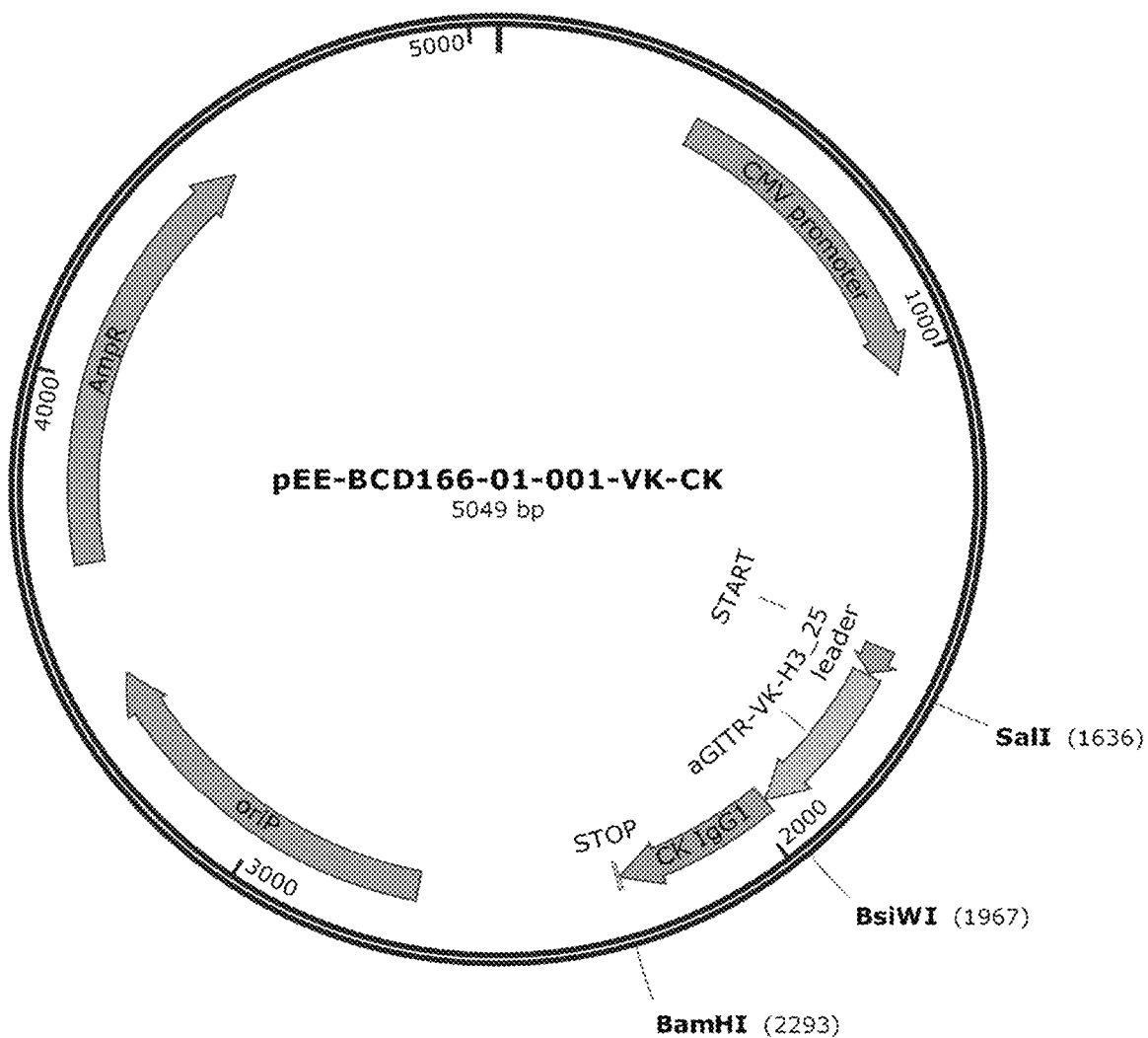

Antibody variable domain genes from Example 7 were cloned according to standard methods. To this end, we generated PCR products containing antibody heavy and light chain variable domain genes. The heavy chain variable domain was cloned into vector pEE-Hc IgG1 at SalI/NheI restriction sites, which schematic map is shown in FIG. 9. The light chain variable domain was ligated into vector pEE-CK at SalI/BsiWI restriction sites, which schematic map is shown in FIG. 10.

Antibodies were generated in established cell line obtained from Chinese hamster ovary cells (CHO-K1) according to published protocols [Biotechnol Bioeng. 2005 Sep. 20; 91(6):670-677, Liao Metal, 2004; Biotechnol Lett. 2006 June; 28(11):843-848; Biotechnol Bioeng. 2003 Nov. 5; 84(3):332-342]. Cells constitutively expressing the EBNA1 (Epstein-Barr virus nuclear antigen 1) protein gene were used.

The CHO-K1-S cell line cells were used to generate antibodies in a transient expression system. Cells were cultured in baffled flasks (125, 250, 500, 1000 and 3000 ml) in a mixture of CHO-S-SFM II and FreeStyle CHO (1:1) media supplemented with 4 mM glutamine, 0.05 mg/ml gentamicin and 10 µg/ml ciprofloxacin in orbital shakers-incubators at +37 C, 5% CO2, and 110 or 150 rpm depending on a flask size. Cells were subcultured 3 times a week, plating density 0.2*106 cells/ml.

For transfection, cells were inoculated the day before transfection at a density of 0.8*106 cells/ml, transfection was performed one day later using a cell culture at a density of 2*106 cells/ml. RPMI-1640 medium supplemented with 2 mM glutamine and 0.05 mg/ml of gentamicin was used to prepare the transfection mixture. Vectors were diluted separately in the medium at 0.75 µg/ml, a transfection agent, polyethyleneimine (PEI), was diluted separately at PEI: DNA 7:1 by weight. The dilutions of vectors and PEI were mixed and incubated for 10 minutes at room temperature, the transfection mixture was then introduced to the cells, and the cells were cultured under standard conditions.

The next day after transfection, a mixture of CHO-S-SFM II and FreeStyle CHO (1:1) media supplemented with 0.05 mg/ml of gentamicin and 10 µg/ml of ciprofloxacin, 1 mM sodium valproate and 10% feeding F12.7 was added to the cells, the cells were cultured in orbital shaker-incubators at +34 C, 5% CO2 and 110 or 150 rpm depending on a flask size. On day 3-4 after transfection, 10% feeding F12.7 was added to the cells.

On day 7 after transfection, cell fluid samples were selected to measure the concentration of protein being produced on Protein-A Biosense chips using OctetRed 96 according to the ForteBio protocol (Table 2). Recombinant antibodies were isolated and purified from culture liquid using Protein A affine HPLC column. Cleared culture liquid was passed through 1 ml HiTrap rProtein A FF column (GE Healthcare) that was equilibrated with phosphate buffered saline (PBS, pH 7.4). Then the column was washed with 5 column volumes of PBS to remove any non-specifically binding components. Bound antibody was eluted using 0.1 M glycine buffer (pH 3). The principal protein elution peak was collected and brought to neutral pH with 1 M Tris buffer (pH 8). All stages were conducted under 110 cm/h flow rate. The protein was then dialyzed into PBS (pH 7.4) by means of SnakeSkin Dialysis Tubing technique, filtered (0.22 µm), transferred into tubes and stored at −70° C.

Figure 11:
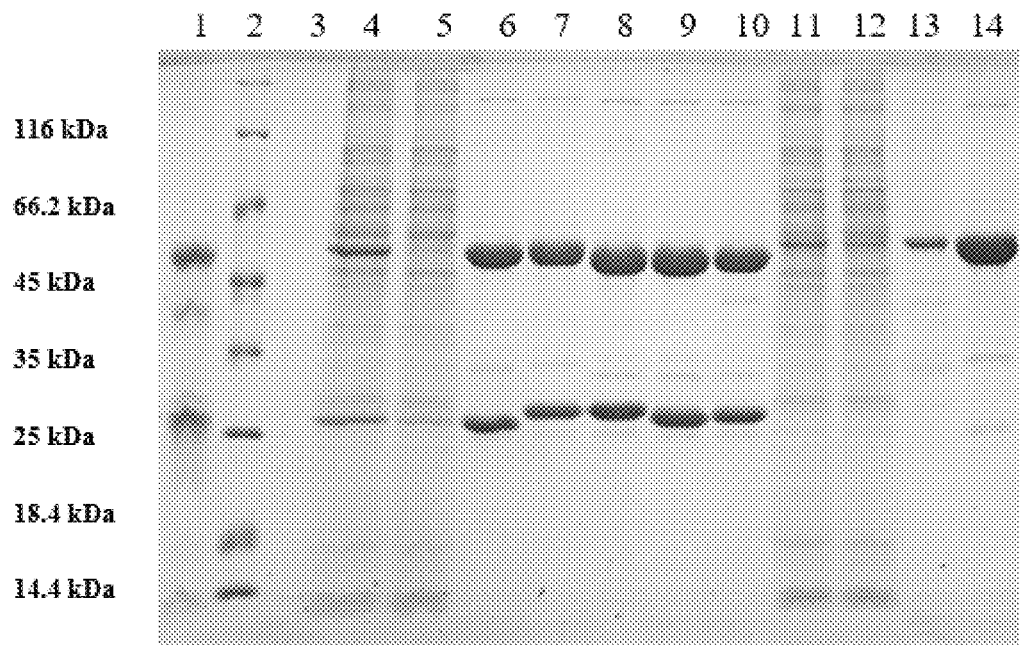
Figure 12:
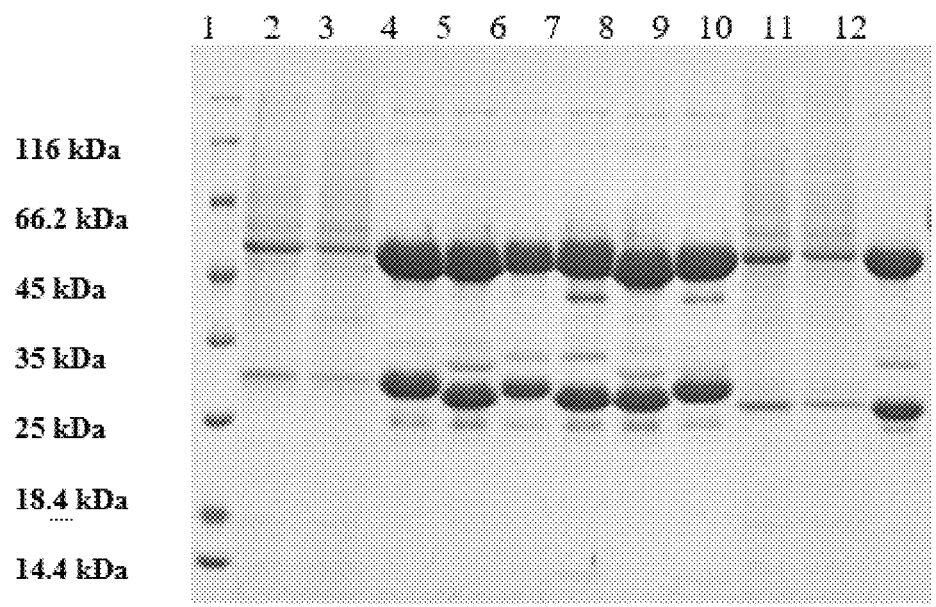

Purity of the resulting protein solution was evaluated by SDS gel electrophoresis (FIGS. 11 and 12). All antibodies comply with purity level required for examining physico-chemical properties and activity in cellular assays.
Table 2.

TABLE 2

| Lot # | Protein name | Concentration of antibodies measured by OCTETRED96 (mg/l) |
|---|---|---|
| 1161 | BCD166-NHVKITSe13-5-H3-25 | 147.0 |
| 1162 | BCD166-NHVKSe13-1-C1-9 | 127.9 |
| 1163 | BCD166-NHVKSe13-1-A1-1 | 119.5 |
| 1164 | BCD166-SPF2Se13-a-F1-38 | 148.0 |
| 1165 | BCD166-SPF2Se13-4-G8-43 | 138,0 |
| 1208 | BCD166-01_VH_ChLVHILBSe12_MP1_A9_3-HC(DEL)_VL_ChLVHILBSe12_MP1_A9_3-CL | 145.4 |
| 1209 | BCD166-01_VH_ChLVHILBSe12_MP1_B11_20-HC(DEL)_VL_ChLVHILBSe12_MP1_B11_20-CL | 163.0 |
| 1210 | BCD166-01_VH_ChLVHILBSe12_MP1_F10_16-HC(DEL)_VL_ChLVHILBSe12_MP1_F10_16-CL | 52.0 |
| 1211 | BCD166-01_VH_ChKVHILKSe13_MP2_B9_57-HC(DEL)_VK_ChKVHILKSe13_MP2_B9_57-CK | 125.2 |
| 1212 | BCD166-01_VH_ChKVHILKS e13_MP2_D2_5-HC(DEL)_VL_ChKVHILKSe13_MP2_D2_5-CL | 136.0 |
| 1213 | BCD166-01_VH_ChLVHILKSe12_MP2_G15-HC(DEL)_VL_ChLVHILKSe12_MP2_G1_5-CL | 109.0 |
| 1214 | BCD166-01_VH_ChKVHILKSe13_MP2_H8_55-HC(DEL)_VK_ChKVHILKSe13_MP2_H8_55-CK | 187.4 |

Example 9

Kinetic Assay of Anti-GITR IgG1 Antibody-Human GITR Interaction

Binding affinity constants for anti-GITR antibody-human/rhesus macaque/cynomolgus monkey GITR interactions were determined using OctetRed 96 according to manufacturer (ForteBio) protocol. Antigen 25 µg/ml was non-specifically immobilized onto the surface of amine-reactive sensors of the second generation (AR2G) (ForteBio, using standard protocol according to manufacturer's instructions for preparation and immobilization of AR2G sensors). of anti-GITR antibodies The antibodies were added at a concentration The assay was conducted at 30° C. using PBS comprising 0.1% Tween®-20 and 0.1% BSA as a working butter.

The resulting sensograms, after subtracting a reference signal, were analyzed using Octet Data Analysis software (Version 8.0) in accordance with the standard procedure and using 1:1 interaction model. The resulting affinity constants are shown in Table 3. All tested antibodies show high affinity and specificity for human GITR.

TABLE 3

Affinity constants for anti-GITR antibody - human GITR interactions.

| No. | Name | Lot # | KD (M) |
|---|---|---|---|
| 1 | BCD166-NHVKITSe13-5-H3-25 | 1161 | $6.38E^{-11}$ |
| 2 | BCD166-NHVKSe13-1-C1-9 | 1162 | $6.81E^{-10}$ |
| 3 | BCD166-NHVKSe13-1-A1-1 | 1163 | $1.96E^{-10}$ |
| 4 | BCD166-SPF2Se13-4-F1-36 | 1164 | $5.76E^{-10}$ |
| 5 | BCD166-SPF2Se13-4-G8-43 | 1165 | $3.30E^{-11}$ |
| 7 | BCD166-01_VH_ChLVHILBSe12_MP1_A9_3-HC(DEL)_VL_ChLVHILBSe12_MP1_A9_3-CL | 1208 | $7.37E^{-11}$ |
| 8 | BCD166-01_VH_ChLVHILBSe12_MP1_B11_20-HC(DEL)_VL_ChLVHILBSe12_MP1_B11_20-CL | 1209 | $6.54E^{-10}$ |
| 9 | BCD166-01_VH_ChLVHILBSe12_MP1_F10_16-HC(DEL)_VL_ChLVHILBSe12_MP1_F10_16-CL | 1210 | $1.84E^{-11}$ |
| 10 | BCD166-01_VH_ChKVHILKSe13_MP2_B9_57-HC(DEL)_VK_ChKVHILKSe13_MP 2_B9_57-CK | 1211 | $3.13E^{-11}$ |

TABLE 3-continued

Affinity constants for anti-GITR antibody - human GITR interactions.

| No. | Name | Lot # | KD (M) |
|---|---|---|---|
| 11 | BCD166-01_VH_ChKVHILKSel3_MP2_D2 5-HC(DEL)_VL_ChKVHILKSel3_MP2_D2_5-CL | 1212 | $<1.0E^{-12}$ |
| 12 | BCD166-01_VH_ChLVHILKSe12_MP2_G1_5-HC(DEL)_VL_ChLVHILKSe12_MP2_G1_5-CL | 1213 | $8.50E^{-09}$ |

TABLE 3-continued

Affinity constants for anti-GITR antibody - human GITR interactions.

| No. | Name | Lot # | KD (M) |
|---|---|---|---|
| 13 | BCD166-01_VH_ChKVHILKSe13_MP2_H8_55-HC(DEL)_VK_ChKVHILKSe13_MP2_H8_55-CK | 1214 | $1.98E^{-10}$ |

Example 10

Determination of Anti-GITR Specific Agonist Activity.

For the assay, we used HEK293-GITR-NFkB-Luc cell line generated on the basis of Hek-293 cell line, stably expressing GITR on the surface and containing the firefly luciferase encoding gene under control of NFkB promoter.

The assay was conducted in a 96-well culture plate. The suspension in each well contained HEK293-GITR-NFkB-Luc cells and the test antibody at a concentration as indicated in the graph. All suspension components were prepared in a nutrient cell culture medium. After adding all the components, the plate was incubated at 37° C., 5% $CO_2$ and then, using a luminescence assay kit and a plate reader, the luciferase intensity in the wells was measured.

Figure 13:
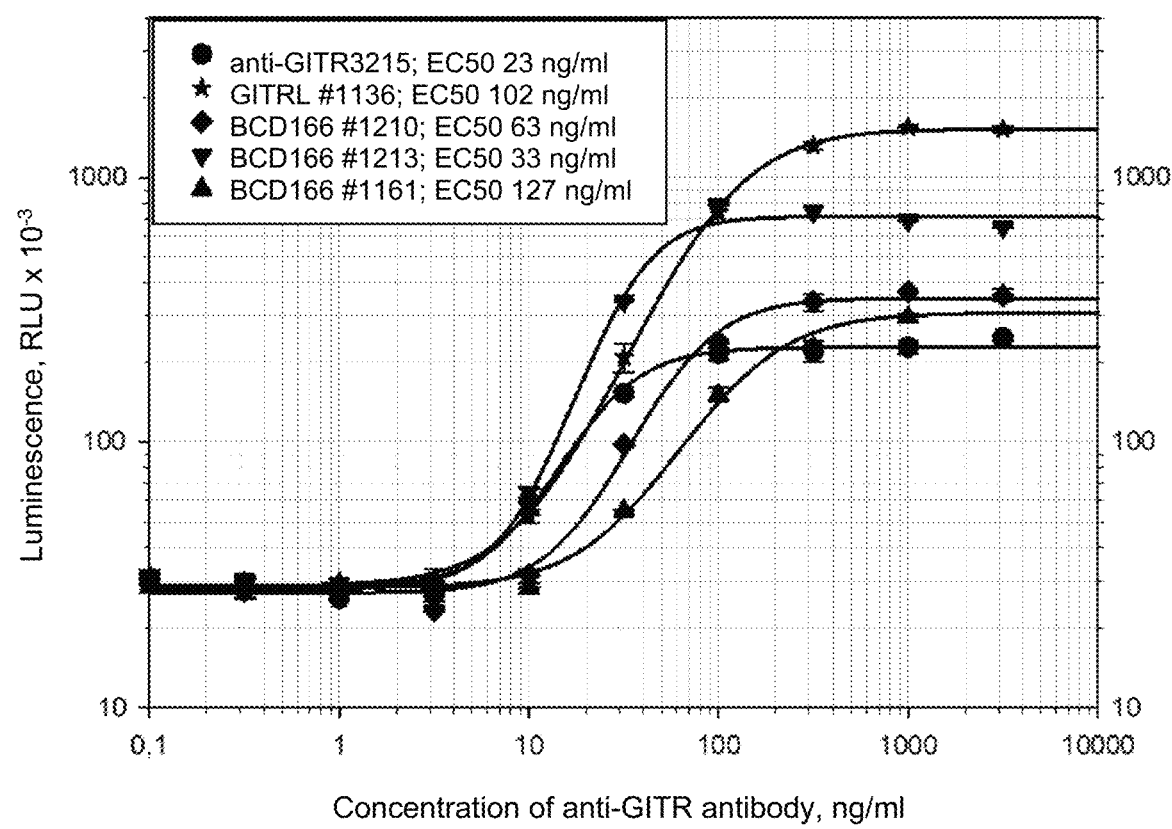

Examination of specific activity of anti-GITR monoclonal antibodies revealed (FIG. 13) that the antibodies of lots 1161, 1210 and 1213 are functionally active and exhibit significant agonist activity with an upper plateau comparable to that of both the control antibody anti-GITR3215 antibody and GITRL. These antibodies were renamed according to Table 4.

TABLE 4

| No. | Old name | Lot # | New name |
|---|---|---|---|
| 1 | BCD166-NHVKITSe13-5-H3-25 | 1161 | BCD166-01-01 |
| 3 | BCD166-01_VH_ChLVHILBSe12_MP1_F10_16-HC(DEL)_VL_ChLVHILBSe12_MP1_F10_16-CL | 1210 | BCD166-01-011 |
| 2 | BCD16601_VH_ChKLVHILKSe12_MP2_G1_5-HC(DEL)_VL_ChLVHILKSe12_MP2_G1_5-CL | 1213 | BCD166-01-014 |

Example 11

Figure 14:
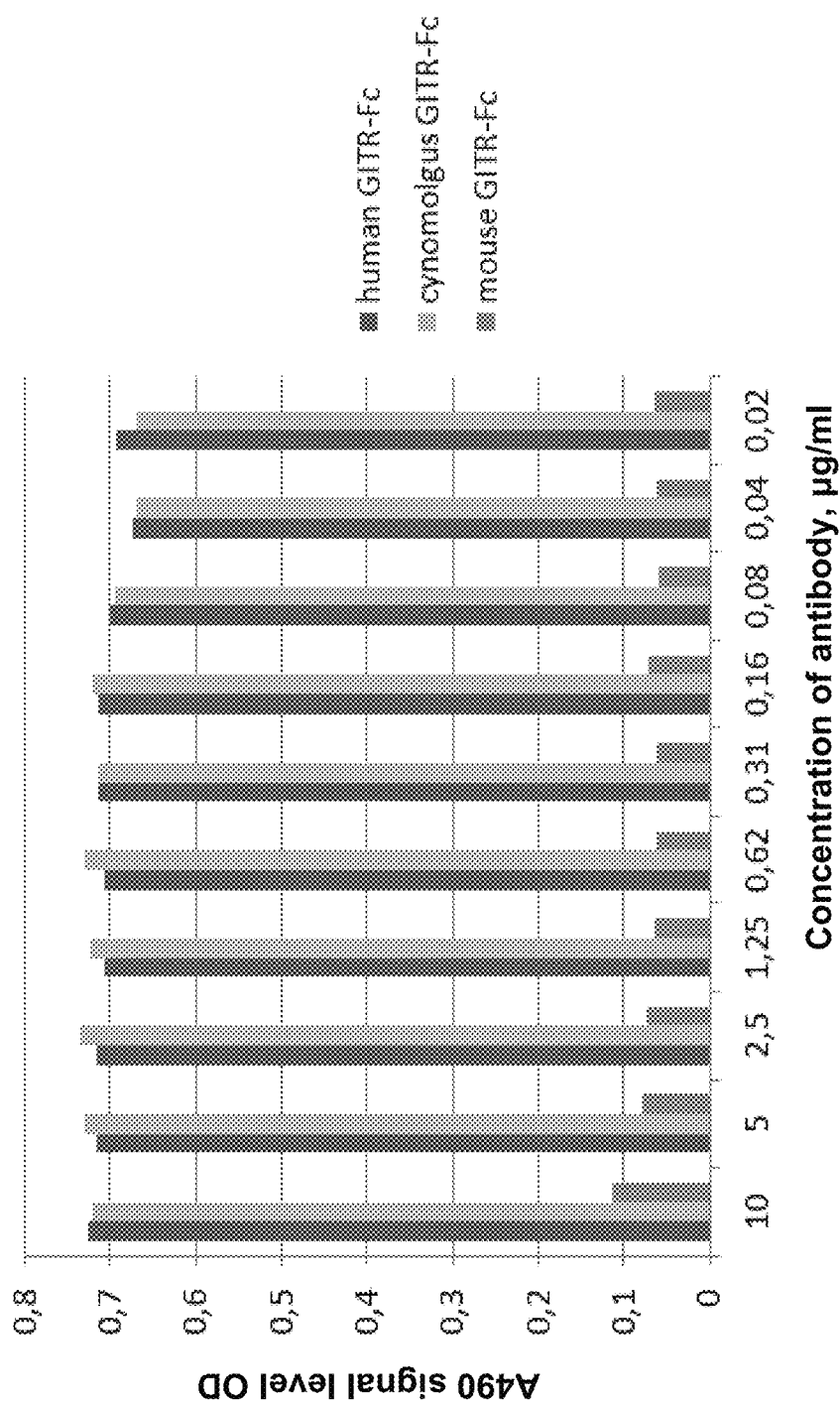
FIG. 14. A graph showing the results of examination of specific binding of BCD166-01-01 antibody to human GITR, mouse GITR, and cynomolgus monkey GITR.
Figure 15:
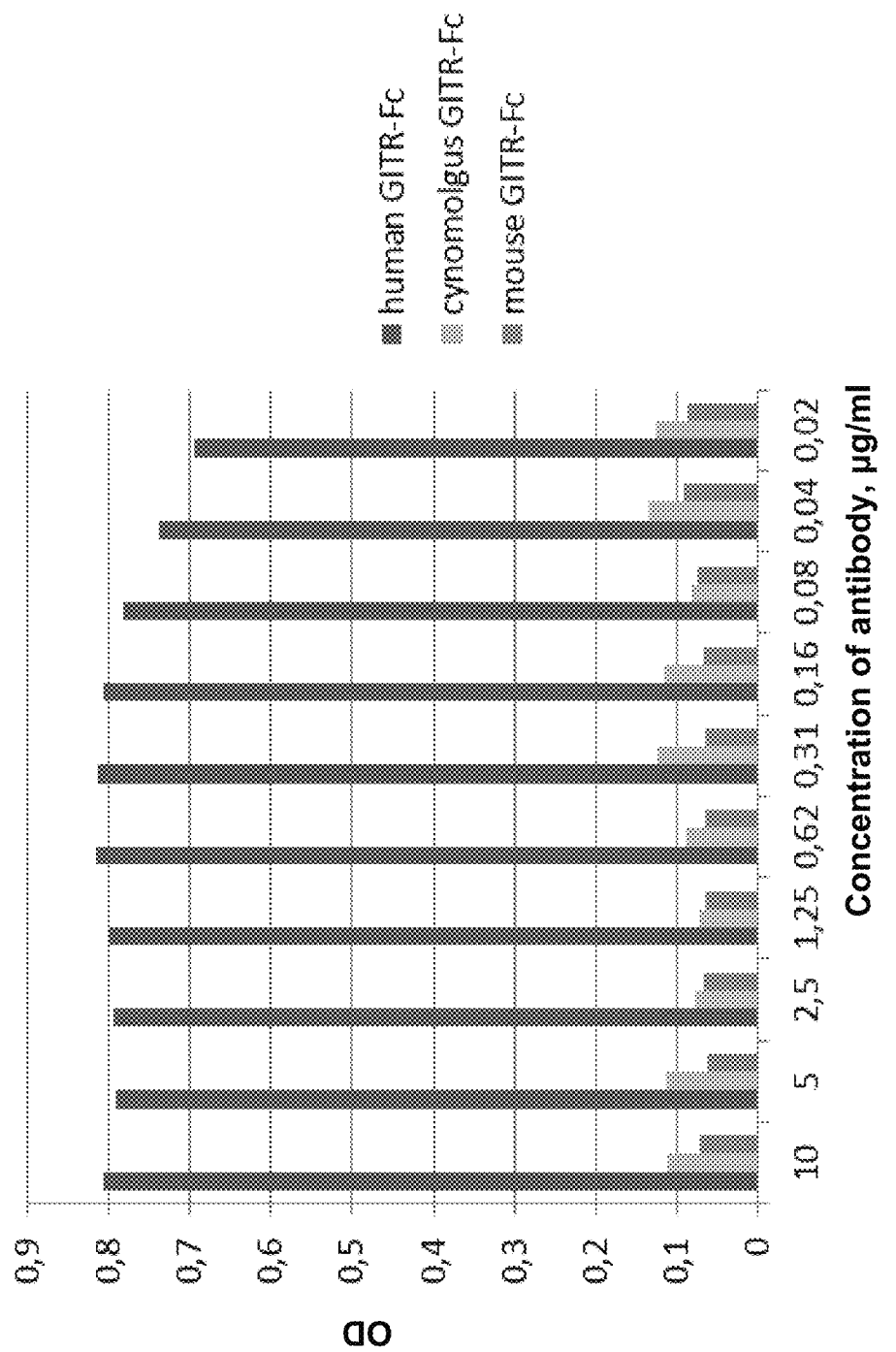
FIG. 15. A graph showing the results of examination of specific binding of BCD166-01-011 antibody to human GITR, mouse GITR, and cynomolgus monkey GITR.
Figure 16:
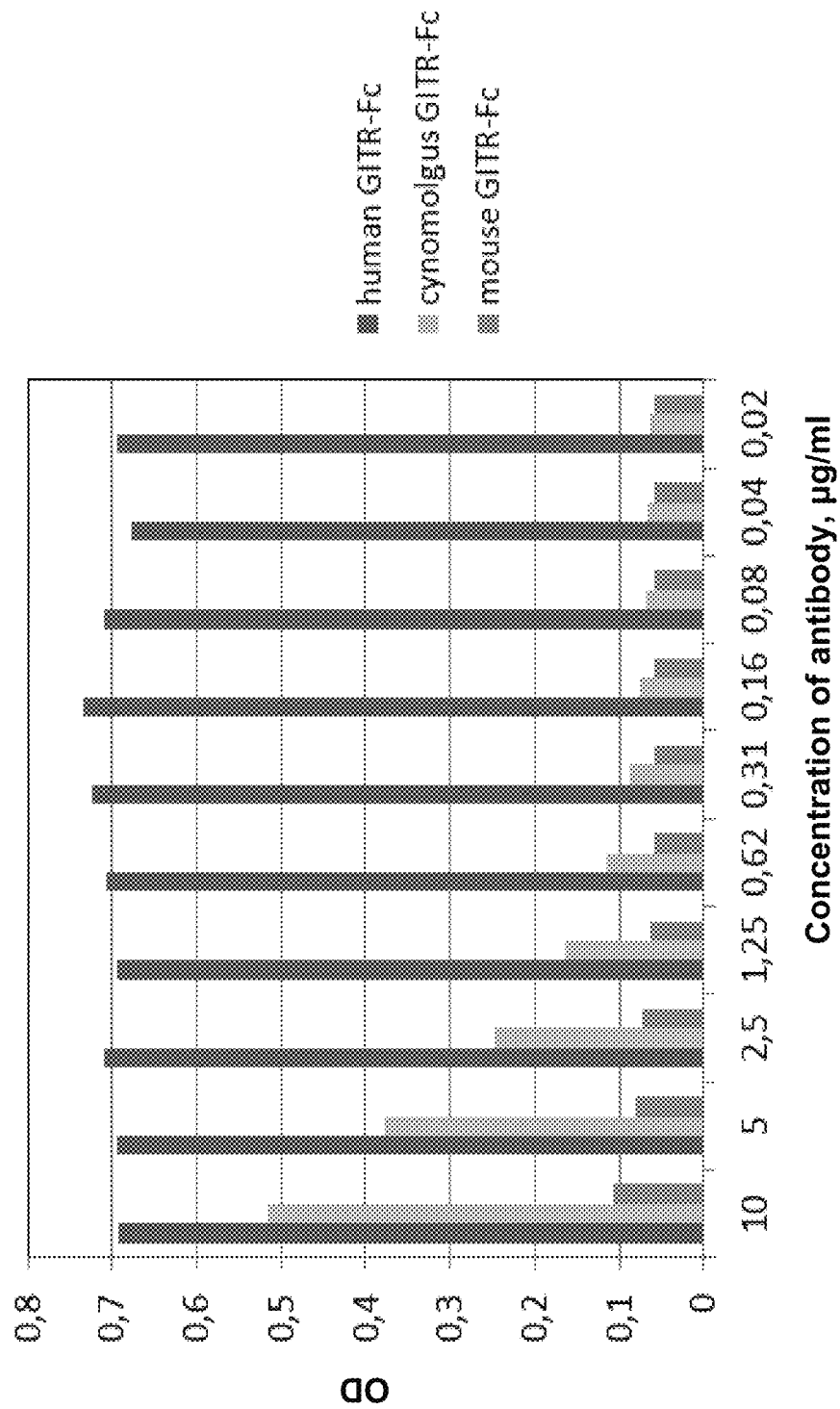
FIG. 16. A graph showing the results of examination of specific binding of BCD166-01-014 antibody to human GITR, mouse GITR, and cynomolgus monkey GITR.

Enzyme-Linked Immunoassay of Interactions Between Anti-GITR Antibodies and GITR from Different Organisms ELISA was used to measure relative affinity of antibodies against GITR-Fc from different organisms. For binding assay, ELISA plate wells (medium binding from Greiner bio one) were coated with 50 µl of human/cynomolgus/murine GITR-Fc (0.5 µg/ml in 1× carbonate buffer), sealed and incubated overnight at 4° C. All further steps were performed in accordance with the standard ELISA protocol described in Example 6. Anti-GITR antibody BCD166-01-01 specifically bound to the human and cynomolgus monkey GITRs and did not bind to the murine GITR (FIG. 14). Antibody BCD166-01-011 specifically bound to the human GITR, but did not exhibit binding to the cynomolgus monkey and murine GITRs (FIG. 15). Antibody BCD166-01-014 specifically bound to the human GITR, while binding to the cynomolgus monkey GITR was much weaker, and absolutely no binding was observed for the murine GITR (FIG. 16). Therefore, candidate BCD166-01-011 was excluded from further study due to the lack of apparent specificity for the monkey GITR. Candidates BCD166-01-01 and BCD166-01-014 were finalized for further development.

Example 12

Kinetic Assay of Anti-GITR IgG1 Antibody—*Macaca mulatta* GITR/*Macaca* Cynomolgus GITR Interactions Binding affinity constants for anti-GITR antibodies and rhesus macaque/cynomolgus monkey GITR were obtained using OctetRed 96 according to manufacturer's (ForteBio) protocol. Antigen 25 µg/ml was non-specifically immobilized onto the surface of amine-reactive sensors of the second generation (AR2G) (ForteBio, using standard protocol according to manufacturer's instructions for preparation and immobilization of AR2G sensors). of anti-GITR antibodies The antibodies were added at a concentration The assay was conducted at 30° C. using PBS comprising 0.1% Tween®-20 and 0.1% BSA as a working buffer.

The resulting sensograms, after subtracting a reference signal, were analyzed using Octet Data Analysis software (Version 8.0) in accordance with the standard procedure and using 1:1 interaction model. The resulting affinity constants are shown in Tables 5 and 6. All tested antibodies exhibit high affinity and specificity for monkey GITR, thus providing the basis for further research on this relevant in vivo animal model.

TABLE 5

Affinity constants of anti-GITR antibody - macaca mulatta GITR interactions.

| | Name of anti-GITK antibody | Lot # | KD (M) |
|---|---|---|---|
| 1 | BCD166-01-01 | 1285 | $9.24E^{-11}$ |
| 2 | BCD166-01-014 | 1284 | $1.92E^{-10}$ |

TABLE 6

Affinity constants of anti-GITR antibody - macaca Cynomolgus GITR interactions.

| | Name of anti-GITR antibody | Lot # | KD (M) |
|---|---|---|---|
| 1 | BCD166-01-01 | 1285 | $5.42E^{-10}$ |
| 2 | BCD166-01-014 | 1284 | $5.53E^{-08}$ |

Example 13

In Vitro Cellular Assay for Determination of Anti-GITR Specific Agonist Activity of Wild and Mutant Candidates with Enhanced Agonist Activity.

For possible enhancement of agonist activity of anti-GITR antibody BCD166-01-01, a human derivative, and based on the study of such substitutions resulting in antibody oligomerization in WO2005047327, WO2006104989 (A2), WO2007005612 (A2) and Science. 2014 Mar. 14; 343 (6176):1260-3, the E358R mutation was selected and introduced into the IgG1 Fc region of antibody. It has been shown that such a mutation can lead to oligomerization of antibody on cell surfaces after binding to antigen, and enhance various effector functions, such as ADCC, ADCP, CDC, as well as pharmacokinetics (PK). The aim was to obtain an antibody with enhanced agonist ability, ADCC, but not CDC. Mutagenesis was performed according to standard genetic engineering protocols, the recombinant antibody was synthesized according to Example 8. The antibody was named and is referred to hereinafter as BCD166-02-01. Two parent antibodies BCD166-01-01, BCD166-01-014 were also assayed.

The assay was performed in the same fashion as that of Example 10.

Figure 17:
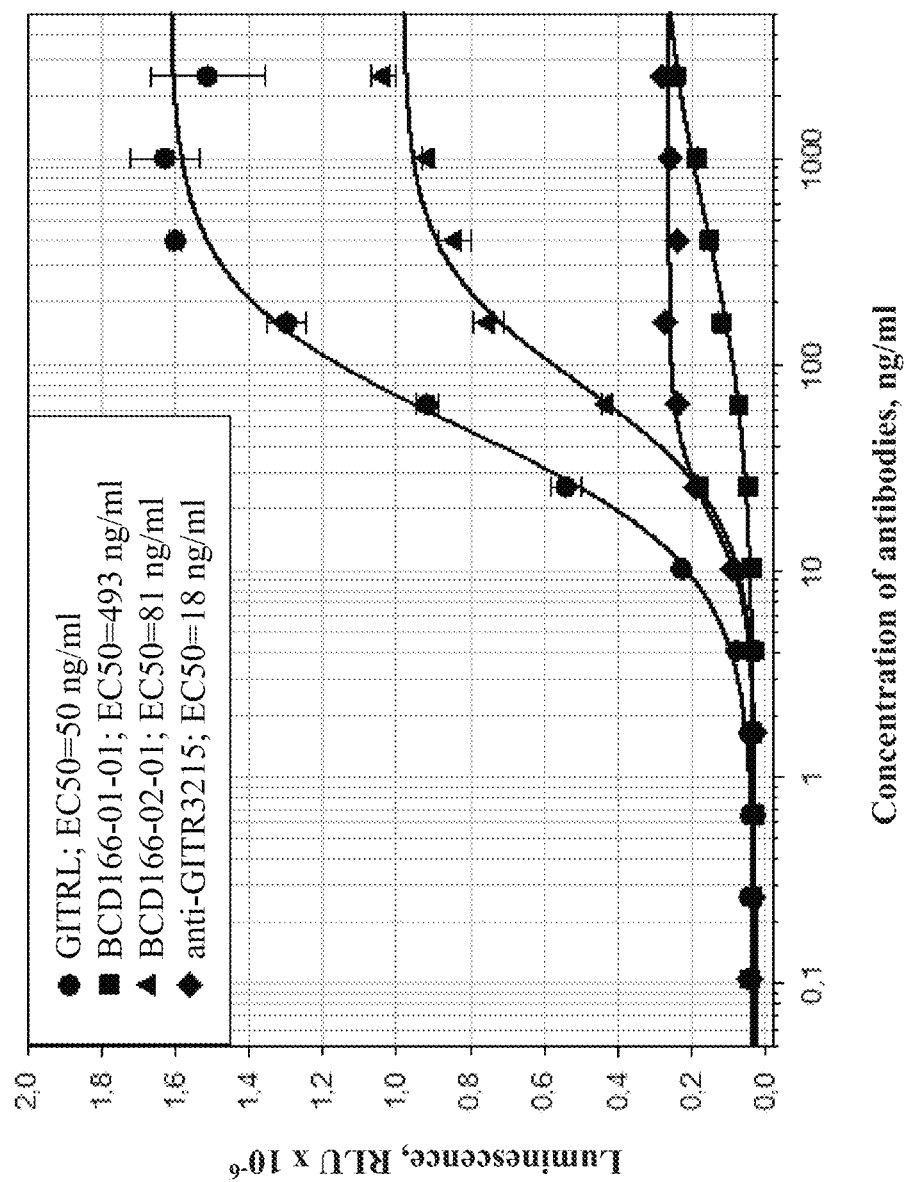
FIG. 17. A graph showing the results of level of activation in a cell agonist assay of BCD166-01-01, BCD166-02-01, BCD166-01-014 in question.

The results shown in FIG. 17 indicate a 5-fold increase in the level of activation in cell agonist assay of test BCD166-02-01 as compared to precursor BCD166-01-01, to which the E358R mutation was introduced, which arises from antigen-dependent oligomerization of anti-GITR antibody BCD166-02-01 on the target cell. Moreover, not only the level of the upper plateau of activation naturally increased, but also the EC50 value increased more than 20 times in the direction of gain.

Example 14

In Vitro Cellular Assay for Antibody-Dependent Cell-Mediated Cytotoxicity (ADCC) of Anti-GITR Antibodies.

In the assay, we studied ADCC activity for candidates BCD166-02-01. Two antibodies BCD166-01-01, BCD166-01-014 were also assayed. Furthermore, by analogy to candidate BCD166-01-01, the E358R mutation was introduced into candidate BCD166-01-014 (which was called BCD166-02-014) to increase ADCC activity relative to that of the wild form.

In the assay, we used Jurkat-NFAT-Luc-CD16 cell line created based on Jurkat cell line, stably expressing CD16 on the surface and containing the firefly luciferase encoding gene under control of NFAT promoter; and Hek-293-GITR cell line created based on Hek-293 cell line, stably expressing GITR on the surface.

The assay was conducted in a 96-well culture plate. The suspension in each well contained Jurkat-NFAT-Luc-CD16 effector cells and Hek-293-GITR target cells, as well as the test antibodies at a concentration as indicated in the graph. All suspension components were prepared in a nutrient cell culture medium. After adding all the components, the plates were incubated at 37° C., 5% CO2 and then, using a luciferase assay kit and a plate reader, we measured the luminescence intensity in the wells.

Figure 18:
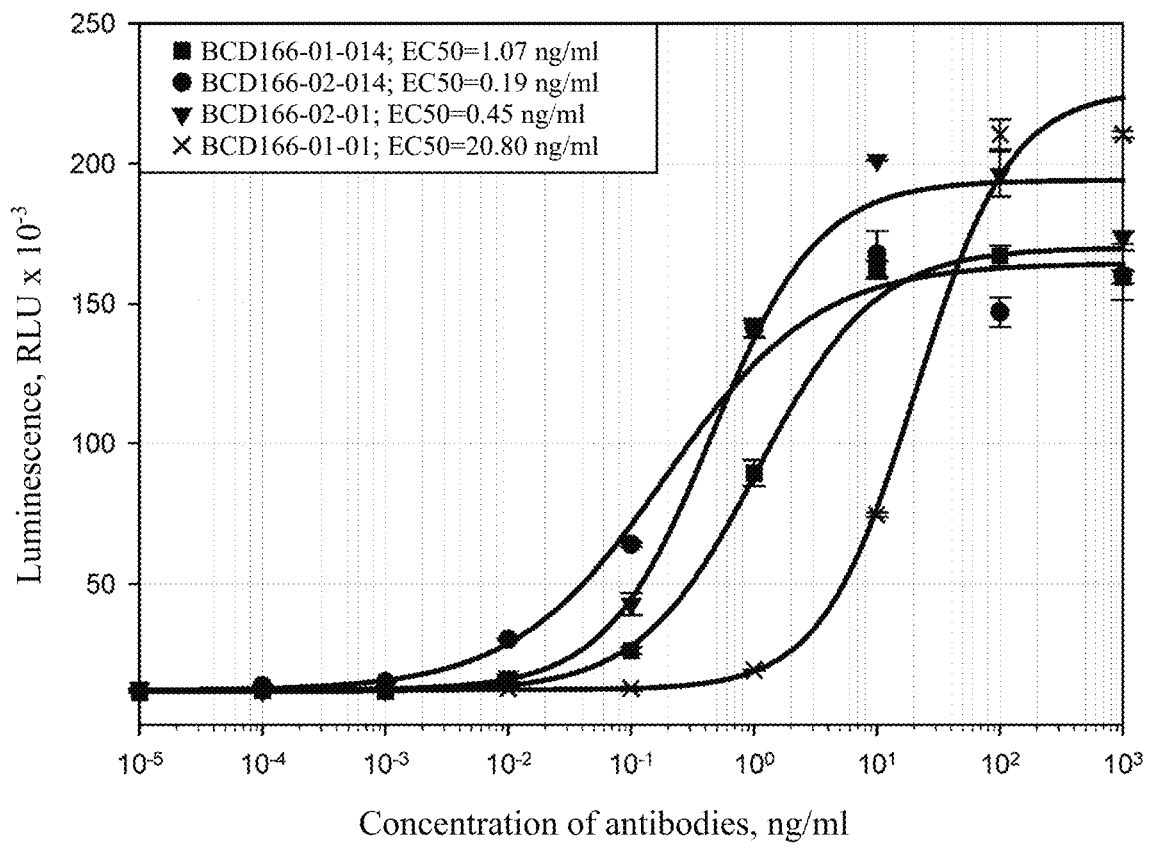
FIG. 18. A graph showing the results of EC50 value in ADCC assay of BCD166-02-01, BCD166-01-01, BCD166-01-014, BCD166-02-014 in question.

The results shown in FIG. 18 indicate a 40-fold increase in the EC50 value in ADCC assay of test BCD166-02-01 as compared to that of precursor BCD166-01-01, to which the E358R mutation was introduced, which arises from antigen-dependent oligomerization of anti-GITR antibody BCD166-02-01 on the target cell. A 5-fold increase in the EC50 value was also reliably detected in ADCC assay of test BCD166-02-14 as compared to that of precursor BCD166-01-14, to which the E358R mutation was introduced. The aggregate data clearly indicate a significant positive effect of the E358R substitution in the Fc portion of IgG1 antibodies on different effector characteristics necessary for the production of a highly active GITR agonist.

Example 15

In Vitro Cellular Assay for Complement-Dependent Cytotoxicity (CDC) of Anti-GITR Antibodies.

In the assay, we studied antibodies BCD166-01-01, BCD166-01-014, BCD166-02-01 and control anti-GITR-3215 antibody.

The assay was conducted in a 96-well culture plate. The suspension in each well comprised HEK-293-GITR cells, as well as test antibodies at an indicated concentration and human serum complement. The plate containing the described suspension was incubated for 4 h at 37° C., 5% $CO_2$. Further, alamar blue solution was added to each well, the plate was then incubated at 37° C., 5% $CO_2$. Further, using a plate reader, fluorescence intensity was measured in wells (excitation wavelength of 544 nm, emission wavelength of 590 nm).

Figure 19:
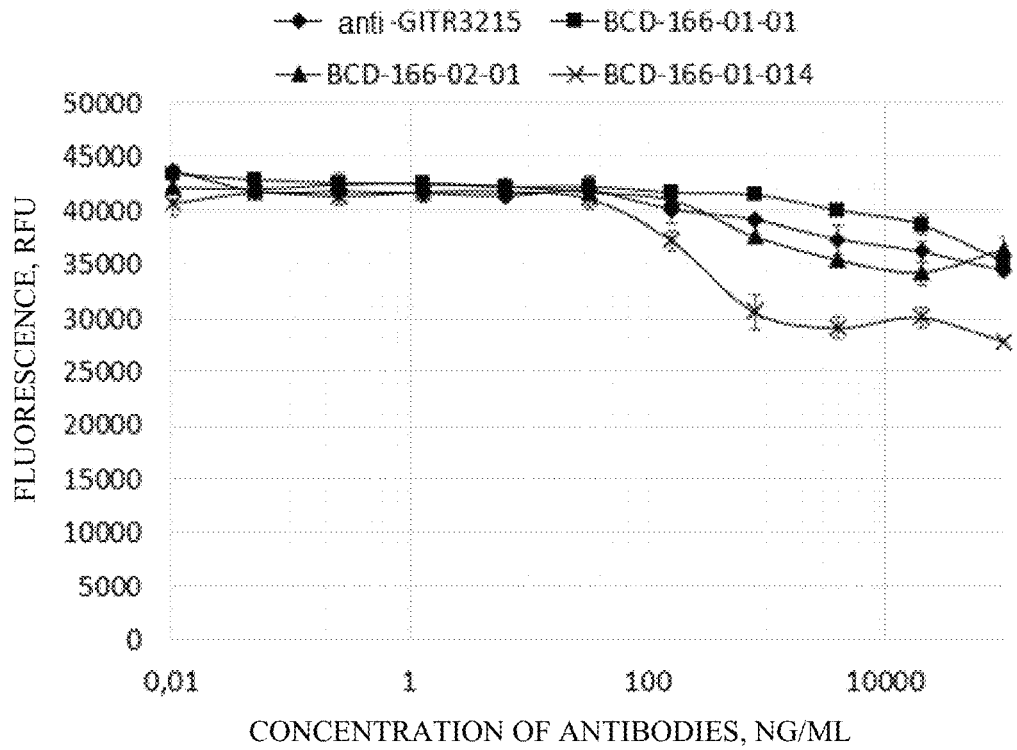
FIG. 19. A graph showing the results of CDC level of BCD166-01-01, BCD166-02-01, BCD166-01-014 in question.
Figure 20:
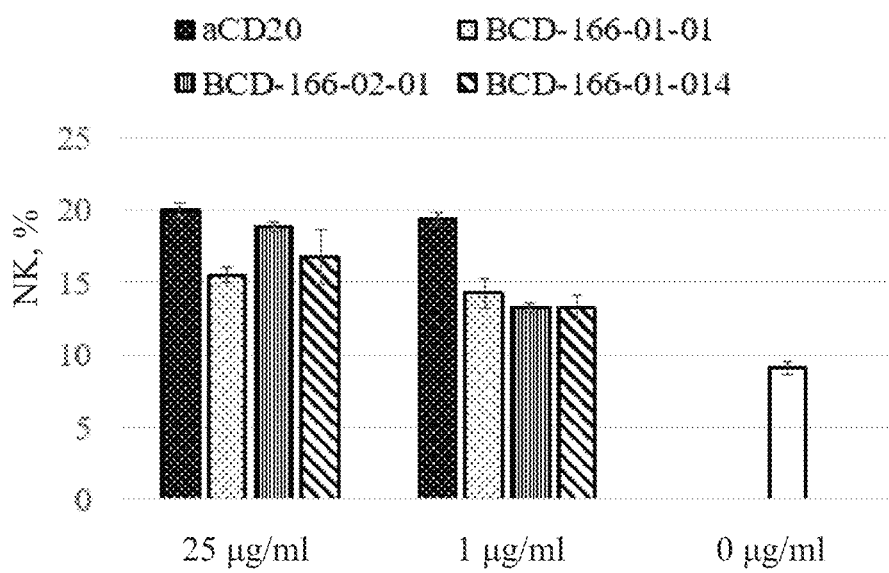
FIG. 20. A graph showing the results of the effect of anti-GITR candidates in question on responder cells (NK) as compared to negative control.
Figure 21:
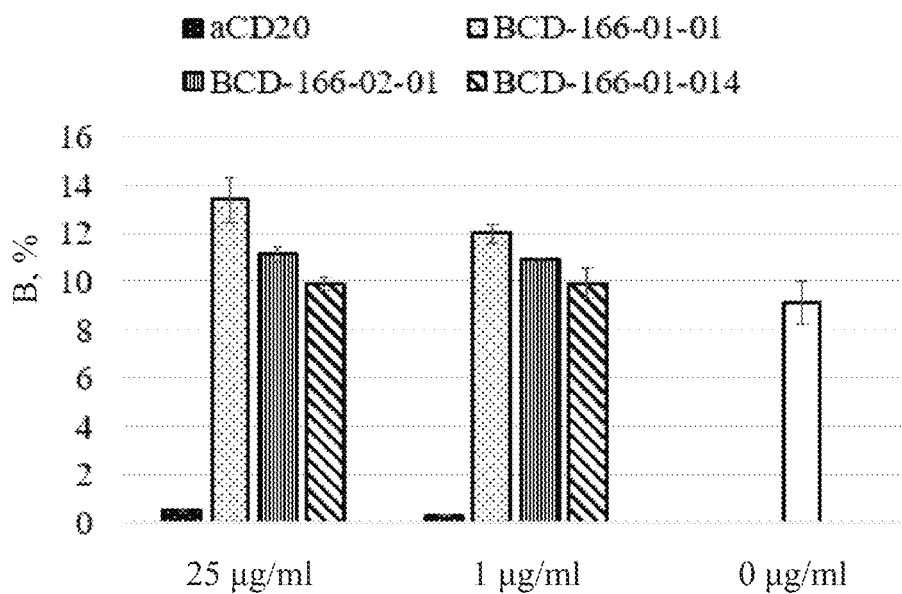
FIG. 21. A graph showing the results of effect of anti-GITR candidates in question on responder cells (B) as compared to negative control.
Figure 22:
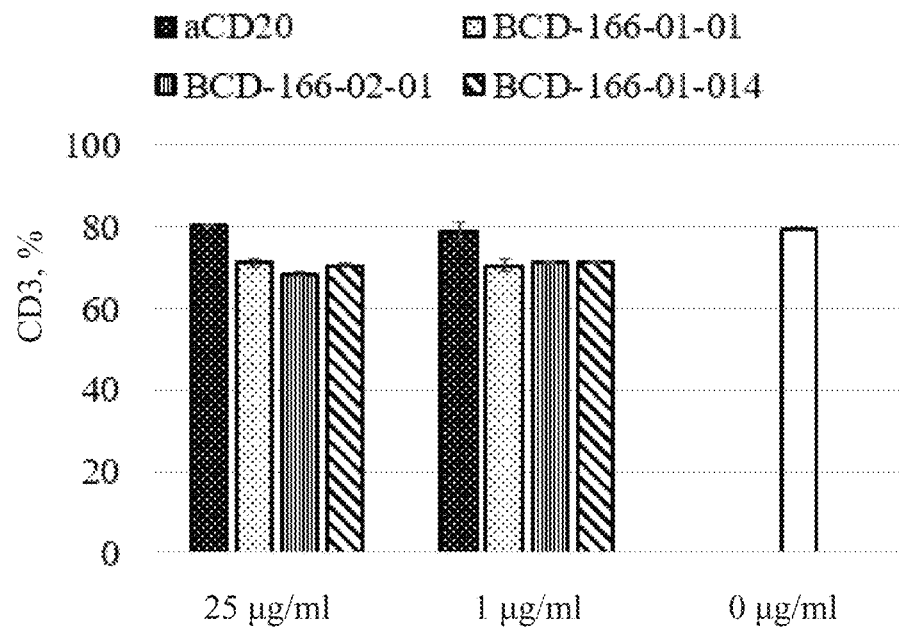
FIG. 22. A graph showing the results of effect of anti-GITR candidates in question on responder cells (CD3) as compared to negative control.
Figure 23:
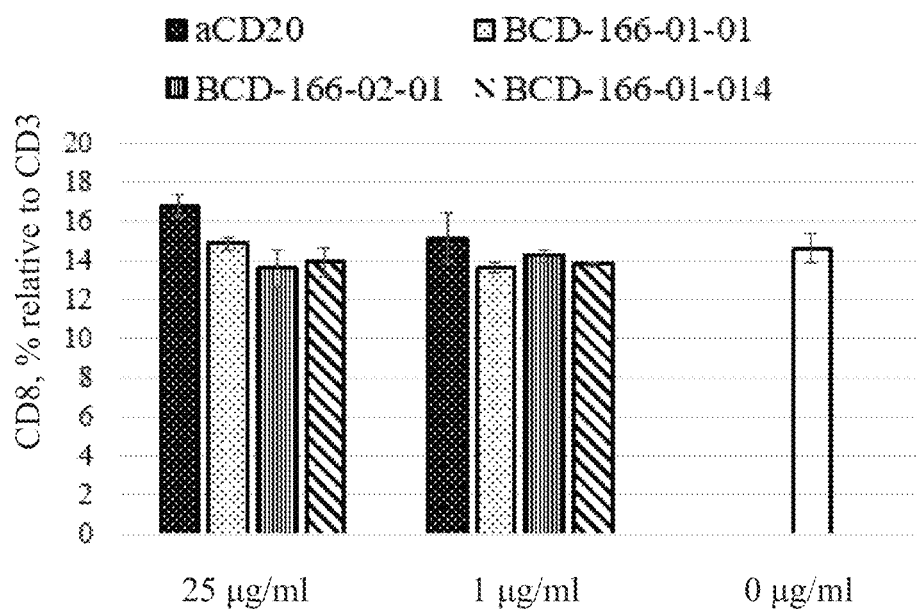
FIG. 23. A graph showing the results of effect of anti-GITR candidates in question on responder cells (CD8+ T cells) as compared to negative control.
Figure 24:
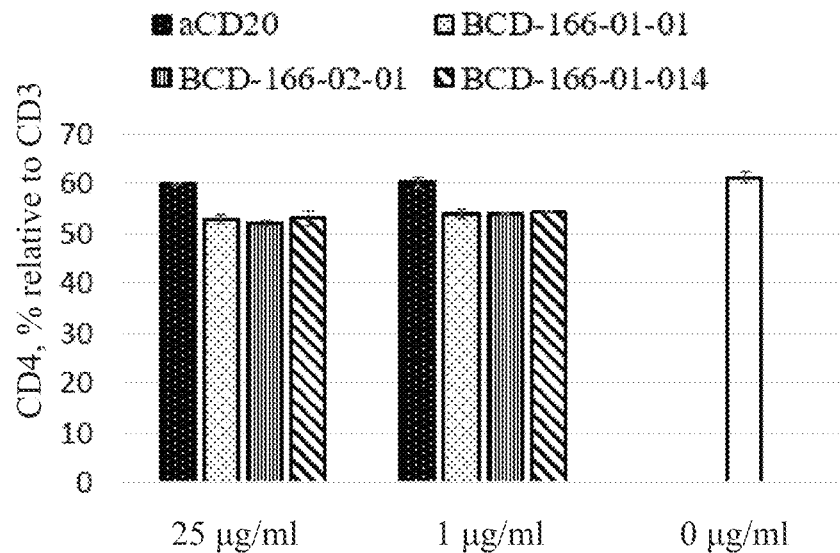
FIG. 24. A graph showing the results of effect of anti-GITR candidates in question on responder cells (CD4+ T cells) as compared to negative control.

The results shown in FIG. 19 indicate insignificant CDC activity, i.e. not more than 10% to a concentration of 1 µg/ml, which is the limit concentration for estimating a therapeutic dose contemplated for use in humans, for antibodies BCD166-01-01, BCD166-02-01 and control anti-GITR-3215 antibody. For candidate BCD166-01-14, CDC activity at a concentration of 1 µg/ml was about 30% lysis, thus indicating an apparent effect, but possibly modest in vivo. The aggregate data clearly indicate an insignificant effect of the E358R substitution in the Fc portion of anti-GITR IgG1 antibody candidates.

Example 16

In Vitro Cellular Cytotoxicity Assay of Anti-GITR Candidates.

The assay was conducted to evaluate the negative or positive effect of test anti-GITR candidates on the change in number of different populations of responder cells. In the assay, we studied antibodies BCD166-01-01, BCD166-01-014, BCD166-02-01 and control anti-CD20 antibody (rituximab).

PBMCs were isolated from whole blood from healthy donors by Ficoll density gradient centrifugation. The assay was conducted in a 96-well culture plate. The suspension in each well contained PBMCs and antibody as indicated in the graph at a concentration of 25, 1 and 0 µg/ml. After mixing PBMCs and antibodies, the plate was incubated for 16 h at 37° C., 5% CO2. Then, the proportion of CD56+, CD19+, CD3+, CD4+ and CD8+ subpopulations of PBMCs in suspensions was measured by direct staining of the suspensions with fluorescent-labeled antibodies against the corresponding CDs and subsequent cell analysis using a flow cytofluorometer. For CD56+, CD19+, CD3+ cells, the graphs show the proportion thereof relative to all cells of test suspension, whereas for CD4+, CD8+, the graphs show the proportion thereof relative to CD3+ cells. The results shown in FIGS. 20-24 indicate a non-significant negative effect of test anti-GITR candidates, i.e. not more than 10% reduction in number of responder cells as compared to the negative control. In the case of NK cell population, we observed about 30-70% increase in cell number depending on the dose. The control anti-CD20 antibody, however, also showed an increase in NK cell percentage, but virtually natural complete depletion of CD20+ B cell population. Thus, all candidates in question do not exhibit non-specific in vitro cytotoxicity toward human blood cells.

Example 17

In Vitro Cellular Assay for Antibody-Dependent Depletion of Human nTreg Cell Population.

ADCC-dependent depletion of $GITR^+$ nTreg cell population is contemplated to be one of the main contemplated mechanisms for the therapeutic anti-oncogenic effect of anti-GITR antibodies. In the assay, we studied antibodies BCD166-01-01, BCD166-01-014, BCD166-02-01 and control anti-CTLA4 antibody (ipilimumab).

Peripheral blood mononuclear cells (PBMCs) were isolated from whole blood from healthy donors by Ficoll density gradient centrifugation. PBMCs were enriched for nTregs using "CD4+CD25+ Regulatory T Cell Isolation Kit, human" (Miltenyi Biotec, Germany). The resulting cells were activated using magnetic beads with immobilized anti-CD3 and anti-CD28 antibodies.

NK cells were isolated from PBMCs using "NK Cell Isolation Kit, human" (Miltenyi Biotec, Germany).

Antibody solutions, NK cell suspension and nTreg suspension were added to a culture plate. The plate was incubated at 37° C., 5% $CO_2$ for 16 hours.

Samples of cell suspensions were stained using fluorescent-labeled antibodies against CD3, CD4, CD25, FoxP3 (Biolegend, USA). Samples of stained cell suspensions were analyzed by flow cytofluorometry.

Figure 25:
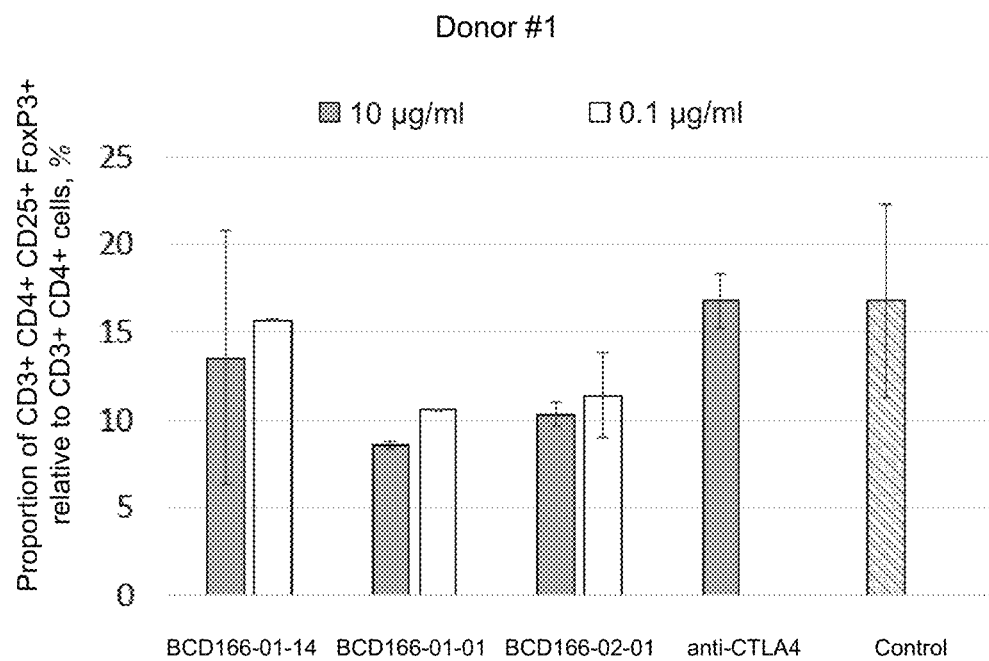
FIG. 25. Analysis of antibody-dependent nTreg depletion under effect of anti-GITR candidates in question for donor 1 cell material.
Figure 26:
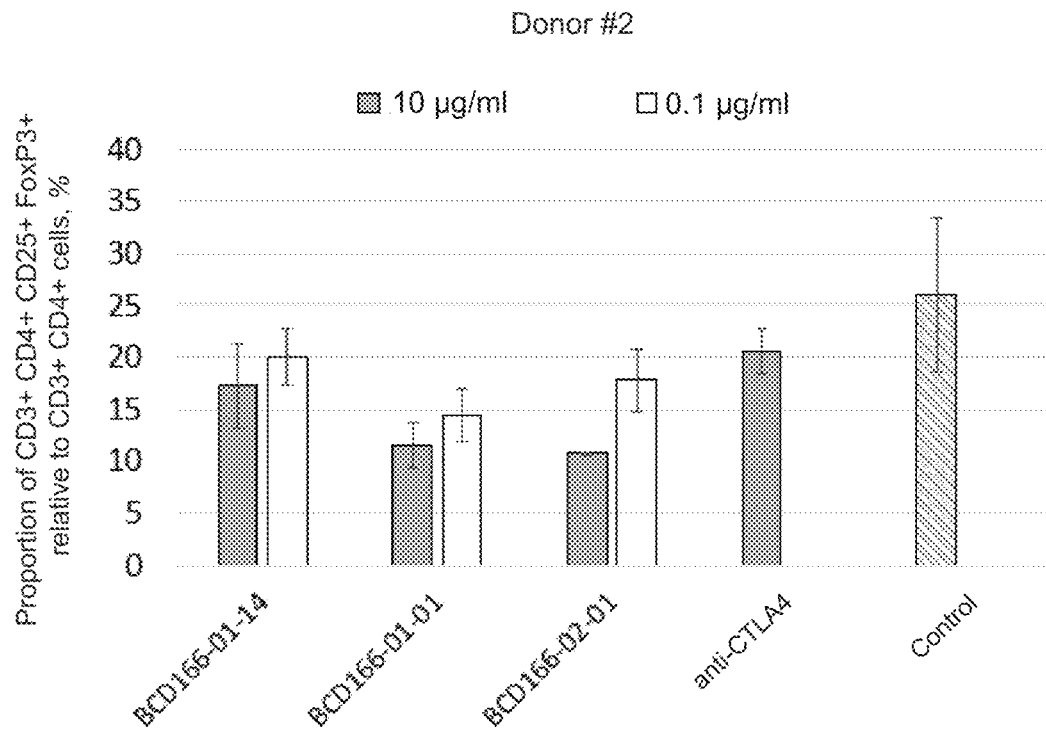
FIG. 26. Analysis of antibody-dependent nTreg depletion under effect of anti-GITR candidates in question for donor 2 cell material.

The results of analysis for antibody-dependent nTreg depletion under effect of test antibodies shown in FIG. 25 for the donor 1 cellular material and in FIG. 26 for donor 2 indicate a significant 70-100% decrease in cell population, i.e. depleting activity of test anti-GITR candidates, especially for the donor 2 material. Furthermore, a comparative analysis with the control anti-CTLA4 antibody ipilimumab shows that anti-GITR antibodies exhibit greater activity, especially the final candidate BCD166-02-01.

Example 18

In Vitro Cellular Assay for Antibody-Dependent Depletion of Human iTreg Cell Population.

ADCC-dependent depletion of GITR+ iTreg cell population is contemplated to be one of the main contemplated mechanisms for the therapeutic anti-oncogenic effect of anti-GITR antibodies. In the assay, we studied antibodies BCD166-01-01, BCD166-01-014, BCD166-02-01.

PBMCs were isolated from whole blood from healthy donors by Ficoll density gradient centrifugation. Monocytes as a population of culture plastic-binding cells were isolated from PBMCs. To obtain dendritic cells, monocytes were incubated in the presence of 1000 units/ml of GM-CSF (Peprotech, USA) and 500 units/ml of IL-4 (Thermo Scientific, USA) at 37° C. 5% $CO_2$ for 120 hours. LPS solution (Sigma, USA) was added to the culture medium to a concentration of 0.5 μg/ml, the cells were incubated at 37° C. 5% $CO_2$ for 48 hours.

Antibody dilution solutions, dendritic cell suspension and PBMCs were added to the culture plate. The plate was incubated at 37° C., 5% $CO_2$ for 120 hours.

Samples of cell suspensions were stained using fluorescent-labeled antibodies against CD3, CD4, CD25, FoxP3 (Biolegend, USA). Samples of stained cell suspensions were analyzed by flow cytofluorometry. Anti-GITR antibodies BCD166-01-01, BCD166-01-14 and BCD166-02-01 induce iTreg depletion in vitro.

Figure 27:
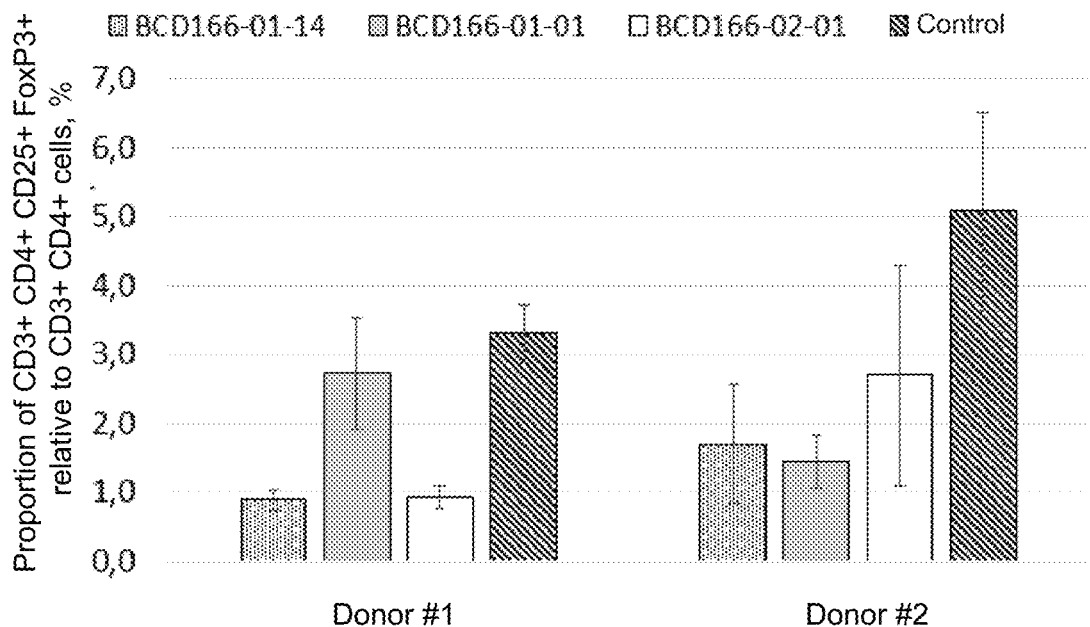
FIG. 27. Analysis of antibody-dependent depletion of iTregs under effect of anti-GITR candidates in question for donor 1 and donor 2 cell material FIG. 28. The results of analysis of effect of anti-GITR antibodies on level of secretion of proinflammatory cytokines IL-2 and IFN-γ stimulating the anti-cancer effect.

The results of assay for antibody-dependent iTreg depletion under effect of test antibodies shown in FIG. 27 for the donor 1/donor 2 cellular material indicate a significant 2-5-fold depleting activity of test anti-GITR candidates, especially for the donor 1 material. The final candidate BCD166-02-01 shows sufficient iTreg depleting activity.

Example 19

In Vitro Cellular Assay for Secretion of Proinflammatory Cytokines IL-2 and IFN-γ Under the Effect of Anti-GITR Antibodies in Human Cell Population.

PBMCs were isolated from whole blood from healthy donors by Ficoll density gradient centrifugation.

Anti-CD3 and anti-GITR antibodies were immobilized in the wells of a 96-well plate. To this end, 100 μl/well of DPBS solution containing anti-GITR antibody BCD166-02-01 at a concentration as indicated in the graph and anti-CD3 antibody at suboptimal concentration were added to corresponding plate wells, the plate was incubated for 16 hours at room temperature.

The assay was performed using a 96-well plate with anti-CD3 and anti-GITR antibodies pre-immobilized in the wells. The suspension in each well contained 40,000 PBMCs and anti-CD28 antibody at suboptimal concentration. All suspension components were prepared in RPMI-1640 medium containing 10% FBS. After adding the cell suspension, the plate was incubated for 6 days at 37° C., 5% CO2. On day 4 of incubation, aliquots of culture liquid were collected from the wells. Then, the concentrations of IL-2 and IFN-γ were measured in culture liquid of day 4 and 6 of incubation using ELISA.

Figure 28:
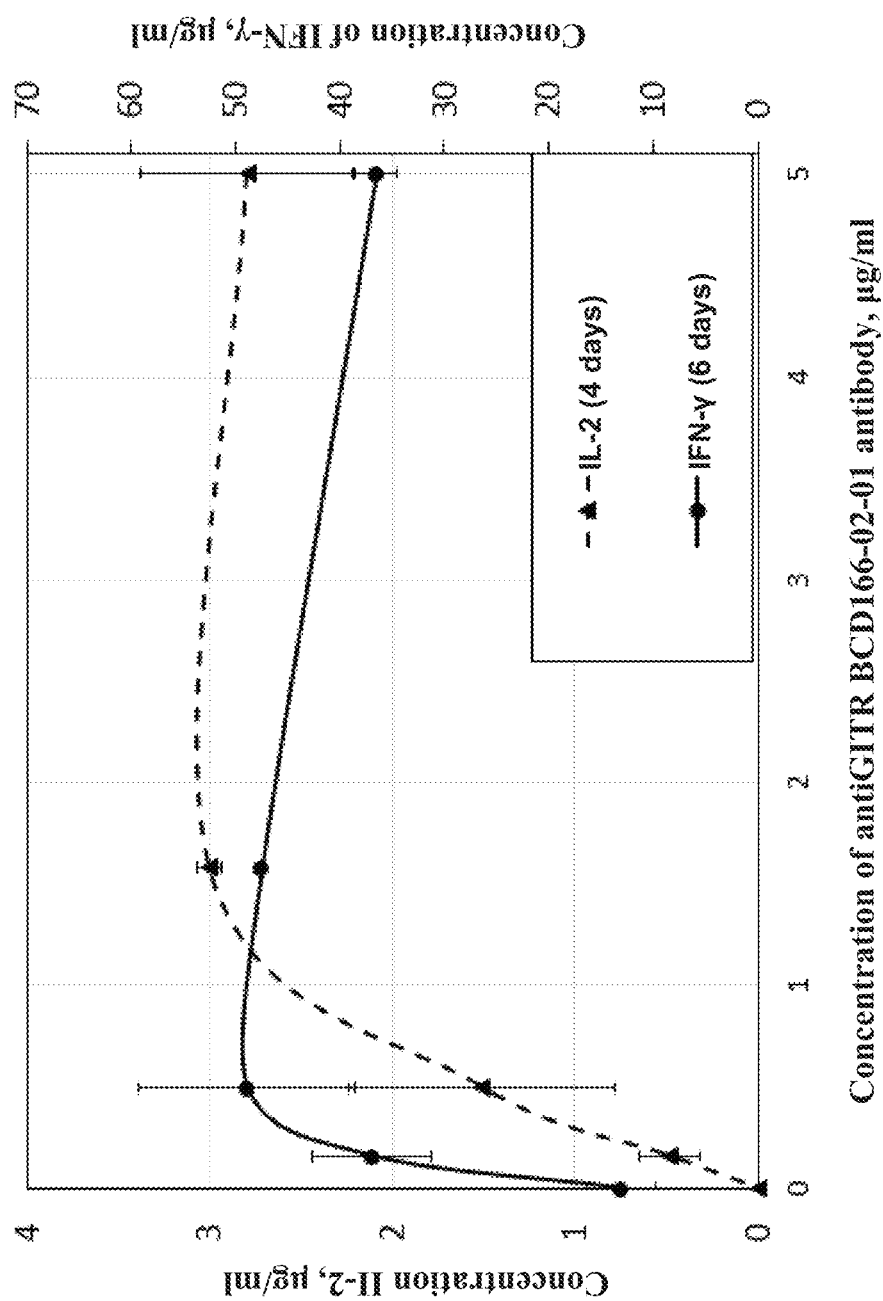

Analysis of the effect of anti-GITR antibodies on the level of secretion of proinflammatory cytokines IL-2 and IFN-γ contributing to anti-cancer effect showed a significant increase in the concentration of these substances in culture liquid (the results are shown in FIG. 28). Thus, candidate BCD166-02-01 exhibits high activity in cytokine secretion activation, which may indicate a significant anti-oncogenic effect.

Example 20

Binding Analysis for Antibody BCD166-02-01-Human FcRn, FcgRIIIa158V, FcgRIIIa158F, FcgRIIa131H, FcgRIIa131R, FcgRIIb and FcgRIa Receptor Interactions.

The binding affinity constants for antibody BCD166-02-01-human FcRn, FcgRIIIa158V, FcgRIIIa158F, FcgRIIa131H, FcgRIIa131R, FcgRIIb and FcgRIa interactions were determined using OctetRed 96 (ForteBio). Biotinylated receptors were immobilized on the surface of streptavidin sensors (SA). We conducted and analyzed the association and dissociation between receptors and antibody in a working buffer (PBS containing 0.1% Tween®-20 and 0.1% BSA: for FcRn receptor we used pH6 buffer, for the other receptors we used pH 7.4 buffer) at 30° C. The resulting sensograms were analyzed in accordance with 1:1 or 2:1 models, the affinity constants were calculated using Octet Data Analysis Software 8.0 User Guide Copyright 2011©.

Results of affinity assay for BCD166-02-01-human FcRn, FcgRIIIa158V, FcgRIIIa158F, FcgRIIa131H, FcgRIIa131R, FcgRIIb and FcgRIa interactions are shown in FIG. 29. They demonstrate multi fold amplified values compared to the literature data and the data repeatedly measured in our company for IgG1 isotype antibodies, thus indicating a noticeable but not qualitative effect of the E358R mutation in the Fc fragment on the kinetics of monomeric antibodies adsorbed on these receptors from solution.

Example 21

Determination of Colloidal and Thermal Stability by Protein Aggregation Point Using Dynamic Light Scattering In order to determine the aggregation temperature of the samples under study by dynamic light scattering, dependence of particle size in the medium on temperature was obtained using DynaPro® Plate Reader II (Wyatt Technology Corp.) with gradual heating from 40 to 85° C. The results are shown in Table 7.

TABLE 7

BCD166-02-01 aggregation point

| Test samples | | Aggregation point |
|---|---|---|
| BCD166-02-01 | 20 mM Acetate, pH = 5.0 | 73.9° C. ± 0.1° C. |
| | 20 mM His, pH = 5.5 | 73.9° C. ± 0.1° C. |

One may conclude that molecule BCD166-02-01 has a high thermo-colloid stability (aggregation point in 20 mM Acetate, pH=5.0 and 20 mM His, pH=5.5 buffer solutions is >65°).

Similar data were obtained for BCD166-01-014.

Example 22

Determination of Thermal Stability Under 50° C. Thermal Stress

The test samples were placed in a thermostated air bath and thermostated at 50° C. for 72 hours. After heating, intact and stressed samples were analysed by size-exclusion HPLC (SEC HPLC) with a UV detector and by capillary isoelectric focusing method. Chromatography was performed on Agilent 1100 HPLC system on Tosoh TSK-Gel G3000SWXL column, and detection was performed at a wavelength of 220 nm. Charge heterogeneity was determined by capillary isoelectric focusing technique using Labchip GX II, Caliper. Preparation of working solutions and the chip was carried out according to standard methods using HT Protein Charge Variant Labeling Kit and Protein Charge Variant Buffer Kit, PerkinElmer.

Figure 30:
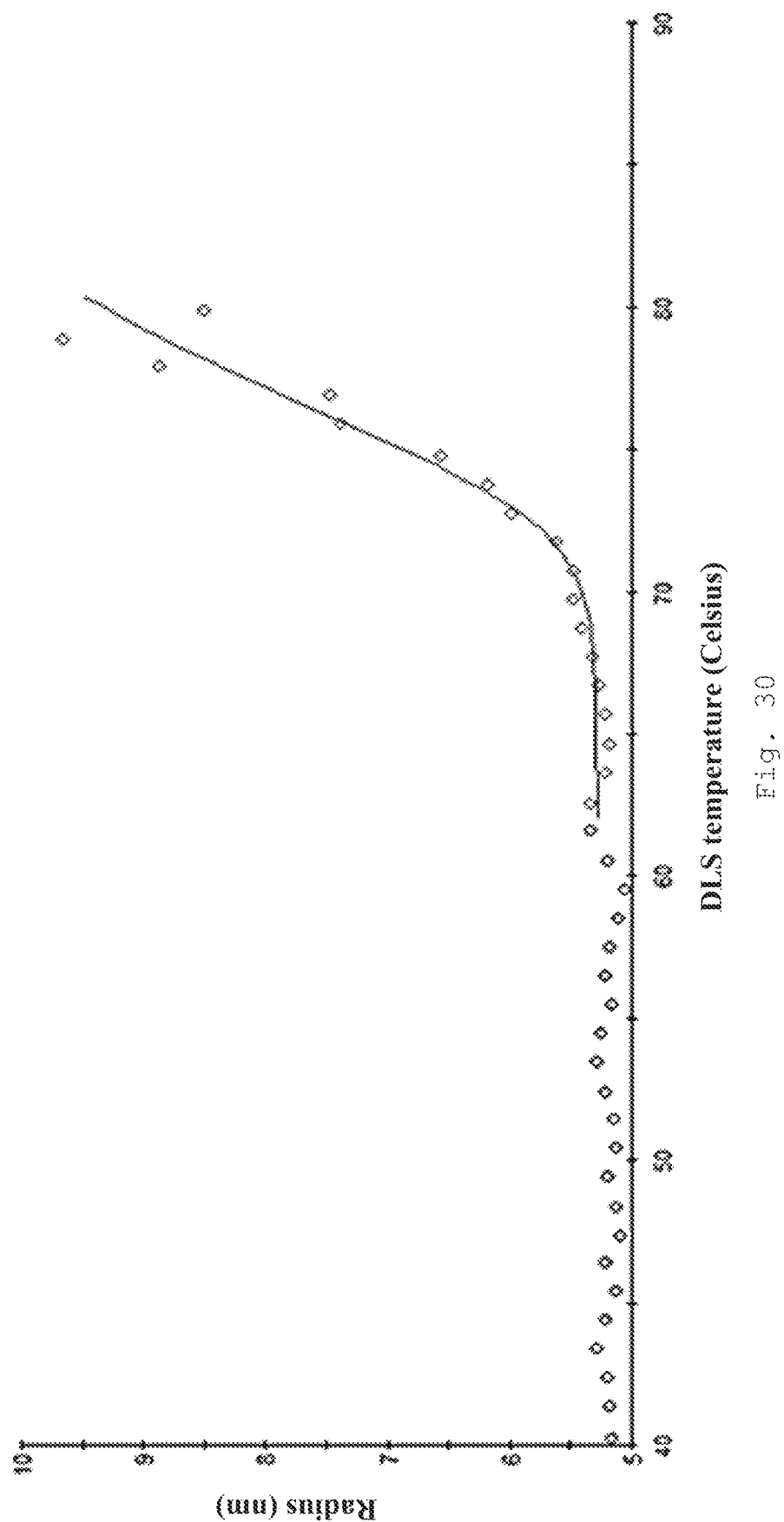
FIG. 30. A graph showing the stability of BCD166-02-01 under 72-hour incubation at 50° C.
Figure 31:
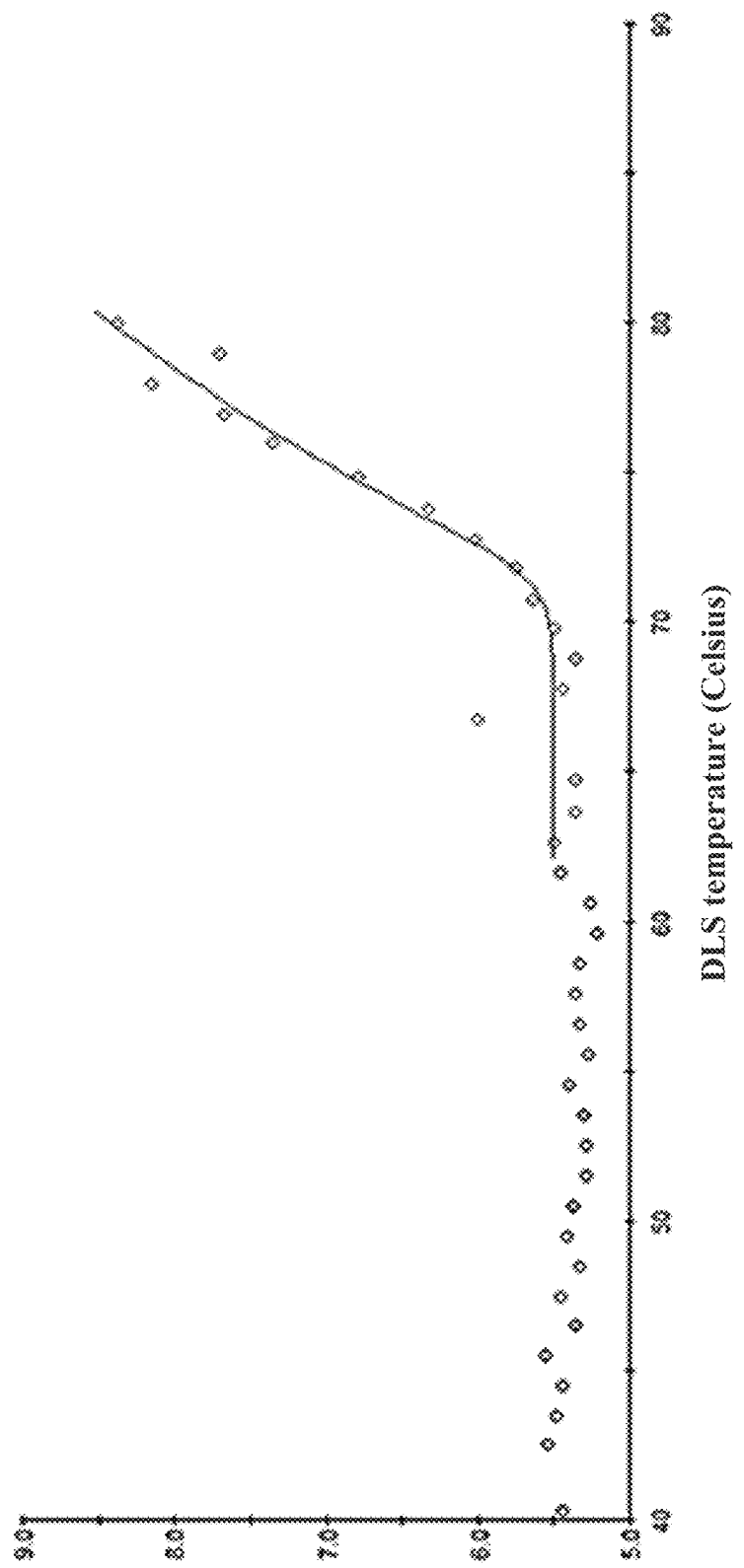
FIG. 31. A graph showing the stability of BCD166-01-014 under 72-hour incubation at 50° C.

The resulting data for BCD-166 stability (for BCD166-02-01 and BCD166-01-014) under 50° C. incubation are shown in Table 8; FIG. 30 (for BCD166-02-01) and 31 (for BCD166-01-014) show combined chromatograms under 72-hour incubation at 50° C.

General conclusion: the sample has high colloidal and thermal stability.

Example 23

Assessment of Anti-Tumor Activity of BCD-166 Products Using a Subcutaneous Xenograft Model Antitumor activity of BCD-166 products was evaluated using a subcutaneous tumor xenograft model. To this end, $3 \times 10^6$ of A2058 cell line cells in admixture with Matrigel® were subcutaneously grafted to humanized huNOG-EXL mice. On day 7 after cell inoculation, the animals were divided in groups as shown in Table 9.

TABLE 9

Groups of animals in the study of anti-tumor activity of BCD-166 products

| Group | Animal qty | Dose |
|---|---|---|
| BCD-166-01-01 | 10 | 20 mg/kg |
| BCD-166-02-01 | 10 | 20 mg/kg |
| BCD-166-01-014 | 9 | 20 mg/kg |
| Negative control | 10 | — |

Products were administered intraperitoneally at a dose of 20 mg/kg on day 1, 5, 8, 12 after dividing the animals in groups. Histidine buffer was administered to the negative control group. Mice body weight and tumor linear dimensions were measured throughout the experiment. Tumor volume was calculated using the formula V=L×W×H×π/6. The efficacy of test product was assessed by the index of tumor growth inhibition (TGI) that was calculated taking into account the mean tumor volume in the negative control group ($V_c$) and the group of product ($V_t$) using the following formula:

$$TGI(\%) = \frac{V_c - V_t}{V_c} * 100$$

Figure 32:
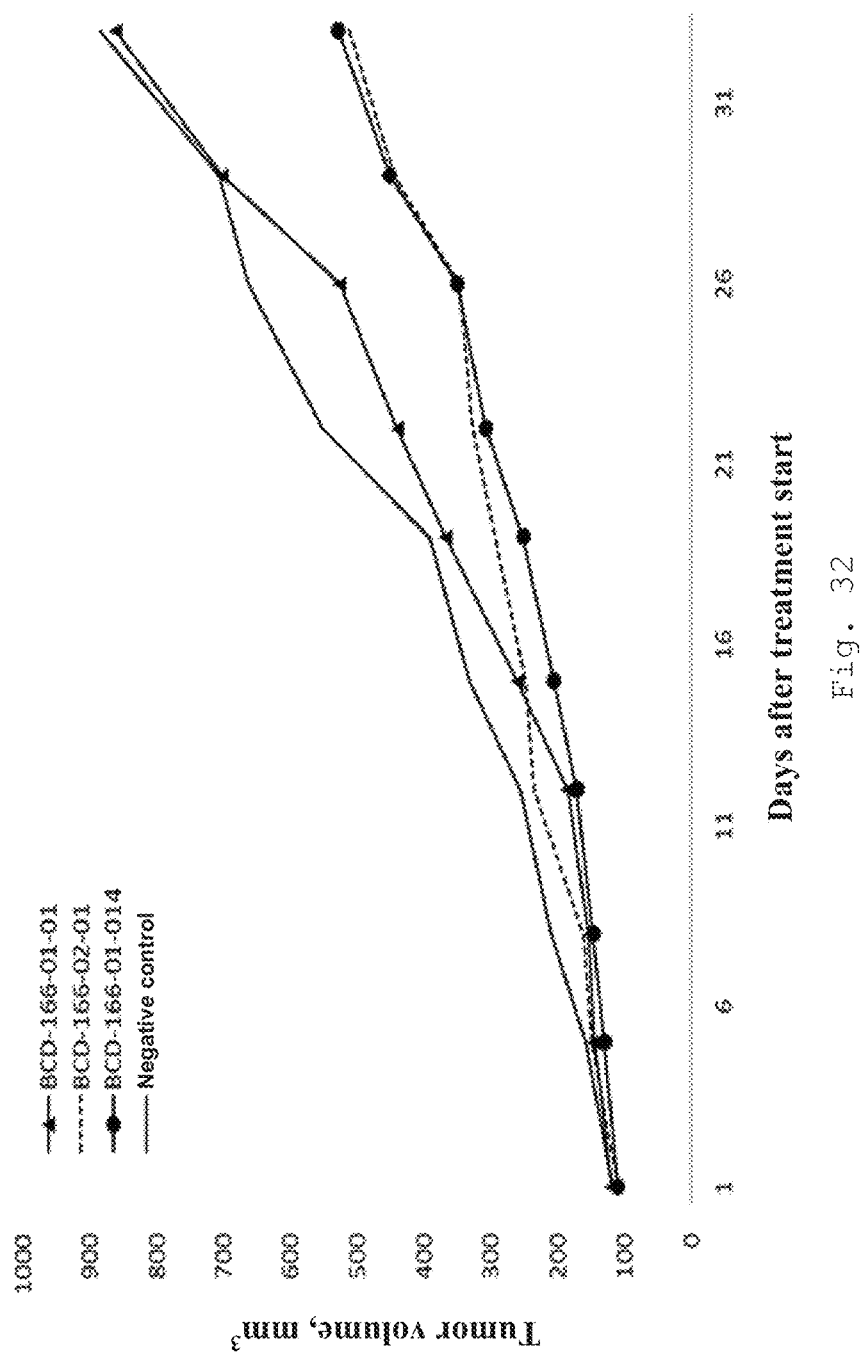
FIG. 32. Mean values of tumor volume in groups during the experiment.
Figure 33:
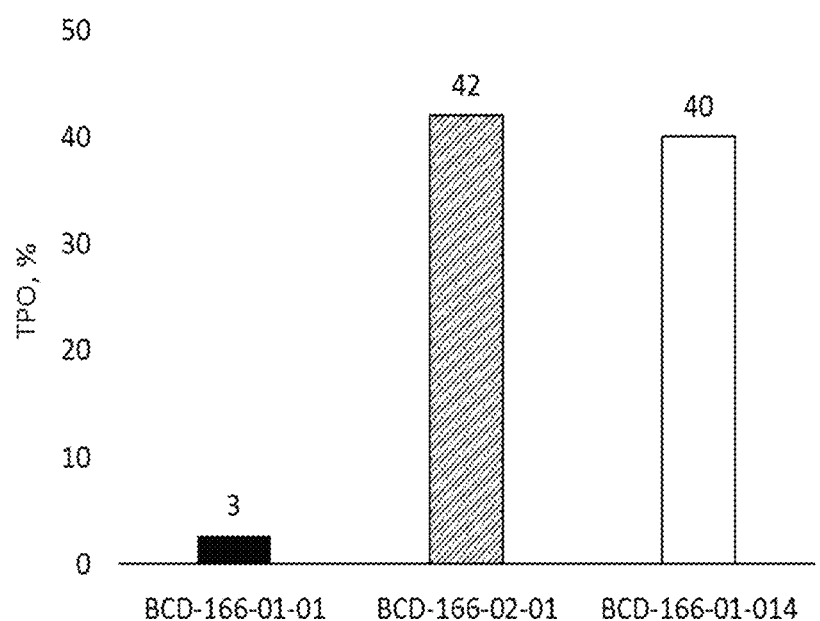
FIG. 33. Index of tumor growth inhibition on day 33.

The experiment revealed high anti-tumor activity of BCD-166-01-014 and BCD-166-02-01 products, whereas BCD-166-01-01 product did not show any significant anti-tumor activity. The results are shown in FIGS. 32 and 33.

TABLE 8

Dependence of monomer content by size-exclusion HPLC and electrophoresis for BCD-166.

| Buffer solution | Conditions for test sample | SEC | | | Isoform profile | | |
|---|---|---|---|---|---|---|---|
| | | Aggregate content, % | Monomer content, % | Fragment content, % | Alkaline fraction, % | Basic fraction, % | Acid fraction, % |
| 20 mM Acetate, pH = 5.0 | Intact | 0.396 | 98.332 | 1.272 | 4.57 | 64.43 | 31.00 |
| | 72 h at 50° C. | 0.432 | 98.664 | 0.905 | 4.01 | 58.90 | 37.09 |
| | Δ * | 0.036 | 0.332 | −0.367 | −0.56 | −5.53 | 6.09 |
| 20 mM His, pH = 5.5 | Intact | 0.416 | 99.110 | 0.474 | 4.48 | 66.93 | 28.59 |
| | 72 h at 50° C. | 0.393 | 99.198 | 0.410 | 4.39 | 60.93 | 34.69 |
| | Δ * | −0.023 | 0.088 | −0.064 | −0.09 | −6.00 | 6.10 |

* Δ is the difference between purity of a stressed sample and purity of an intact sample (input control), %.

The invention claimed is:

1. An isolated monoclonal antibody or antigen-binding fragment thereof that specifically binds to GITR comprising:
   (i) a heavy chain variable domain that comprises CDR 1, CDR 2 and CDR 3 comprising amino acid sequences represented by the sequences of SEQ ID NO: 1, SEQ ID NO:2 and SEQ ID NO: 3, respectively; and
   a light chain variable domain that comprises CDR 1, CDR 2 and CDR 3 comprising amino acid sequences represented by the sequences of SEQ ID NO: 7, SEQ ID NO:8 and SEQ ID NO:9, respectively; or
   (ii) a heavy chain variable domain that comprises CDR 1, CDR 2 and CDR 3 comprising amino acid sequences represented by the sequences of SEQ ID NO: 12, SEQ ID NO: 13 and SEQ ID NO: 14, respectively; and
   a light chain variable domain that comprises CDR 1, CDR 2 and CDR 3 comprising amino acid sequences represented by the sequences of SEQ ID NO: 17, SEQ ID NO: 18 and SEQ ID NO: 19, respectively.

2. A monoclonal antibody or antigen-binding fragment thereof according to claim 1, wherein
   (i) the heavy chain variable domain comprises the amino acid sequence of SEQ ID NO: 4; and
   the light chain variable domain comprises the amino acid sequence of SEQ ID NO: 10; or (ii)
   the heavy chain variable domain comprises the amino acid sequence of SEQ ID NO: 15; and
   the light chain variable domain comprises the amino acid sequence of SEQ ID NO: 20.

3. A monoclonal antibody according to claim 1, wherein the antibody that specifically binds to GITR is a full-length IgG antibody.

4. A monoclonal antibody according to claim 3, wherein the full-length IgG antibody is selected from human IgG1, IgG2, IgG3, and IgG4 isotype.

5. A monoclonal antibody according to claim 1, wherein the antibody that specifically binds to GITR comprises an E358R mutation in SEQ ID NO: 5 to increase agonist properties, antibody-dependent cellular cytotoxicity (ADCC), but not complement-dependent cytotoxicity (CDC).

6. A monoclonal antibody according to claim 1 wherein the heavy chain comprises:
   (i) an amino acid sequence that is at least 90% homologous to the sequence of SEQ ID NO: 5;
   (ii) an amino acid sequence that is at least 90% homologous to the sequence of SEQ ID NO: 6; or
   (iii) a heavy chain comprising an amino acid sequence that is at least 90% homologous to the sequence of SEQ ID NO: 16.

7. A monoclonal antibody according to claim 1 comprising:
   (i) a heavy chain comprising the amino acid sequence of SEQ ID NO: 5;
   (ii) a heavy chain comprising the amino acid sequence of SEQ ID NO: 6; or
   (iii) a heavy chain comprising the amino acid sequence of SEQ ID NO: 16.

8. A monoclonal antibody according to claim 1 comprising a light chain comprising an amino acid sequence that is at least 90% homologous to the sequence of SEQ ID NO: 11 or a light chain comprising an amino acid sequence that is at least 90% homologous to the sequence of SEQ ID NO: 21.

9. A monoclonal antibody according to claim 1 comprising a light chain comprising the amino acid sequence of SEQ ID NO: 11 or a light chain comprising the amino acid sequence of SEQ ID NO: 21.

10. A monoclonal antibody according to claim 1 comprising:
    (i)
       a heavy chain comprising an amino acid sequence that is at least 90% homologous to the sequence of SEQ ID NO: 5; and
       a light chain comprising an amino acid sequence that is at least 90% homologous to the sequence of SEQ ID NO: 11;
    (ii)
       a heavy chain comprising an amino acid sequence that is at least 90% homologous to the sequence of SEQ ID NO: 6; and
       a light chain comprising an amino acid sequence that is at least 90% homologous to the sequence of SEQ ID NO: 11; or
    (iii)
       a heavy chain comprising an amino acid sequence that is at least 90% homologous to the sequence of SEQ ID NO: 16; and
       a light chain comprising an amino acid sequence that is at least 90% homologous to the sequence of SEQ ID NO: 21.

11. A monoclonal antibody according to claim 1 comprising:
    (i)
       a heavy chain comprising the amino acid sequence of SEQ ID NO: 5; and
       a light chain comprising the amino acid sequence of SEQ ID NO: 11;
    (ii)
       a heavy chain comprising the amino acid sequence of SEQ ID NO: 6; and
       a light chain comprising the amino acid sequence of SEQ ID NO: 11; or
    (iii)
       a heavy chain comprising the amino acid sequence of SEQ ID NO: 16; and
       a light chain comprising the amino acid sequence of SEQ ID NO: 21.

12. An isolated nucleic acid encoding an antibody or antigen-binding fragment thereof according to claim 1.

13. A nucleic acid according to claim 12, wherein the nucleic acid is DNA.

14. An expression vector comprising a nucleic acid according to claim 12.

15. A method of obtaining a host cell for obtaining of an antibody or antigen-binding fragment thereof according to claim 1 comprising transformation of a cell with a vector comprising a nucleic acid encoding the antibody or antigen-binding fragment thereof.

16. A host cell for obtaining of an antibody or antigen-binding fragment thereof according to claim 1 comprising a nucleic acid encoding the antibody or antigen-binding fragment thereof.

17. A method of obtaining an antibody or antigen-binding fragment thereof according to claim 1 comprising culturing of a host cell for obtaining of the antibody or antigen-binding fragment thereof comprising a nucleic acid-encoding the antibody or antigen-binding fragment thereof in a culture medium under conditions sufficient to obtain said antibody.

18. A pharmaceutical composition comprising an antibody or antigen-binding fragment thereof according to claim 1 in a therapeutically effective amount in combination with one or more pharmaceutically acceptable excipients.

19. A pharmaceutical composition according to claim 18 wherein the composition comprises at least one therapeutically active antitumour compound in a therapeutically effective amount.

20. A pharmaceutical composition according to claim 19, wherein the therapeutically active antitumour compound is selected from a chemotherapeutic agent, antibody or anti-hormonal agent.

21. A pharmaceutical composition according to claim 20, wherein the therapeutically active antitumour compound is
    (i) an antibody selected from the group: anti-PD1 antibodies, anti-PD-L1 antibodies, anti-CTLA4 antibodies, anti-4-1 BB antibodies, anti-OX40 antibodies or combinations thereof,
    (ii) a small molecule, or
    (iii) selected from the group of activators of innate or adaptive immunity.

22. A pharmaceutical composition according to claim 21, wherein the isolated monoclonal antibody or antigen-binding fragment thereof that specifically binds to GITR comprises:
    a heavy chain comprising the amino acid sequence of SEQ ID NO: 16;

a light chain comprising the amino acid sequence of SEQ ID NO: 21, and the at least one therapeutically active antitumour compound are administered sequentially; or wherein the antibody or antigen-binding fragment thereof that specifically binds to GITR and the at least one therapeutically active antitumour compound are administered simultaneously.

23. A method for inhibition of biological activity of GITR in a subject in need of such inhibition comprising administration of an effective amount of an antibody or antigen-binding fragment thereof according to claim 1.

24. The method according to claim 23, wherein the method is performed for treating a disease or disorder, and wherein the disease or disorder is selected from the group: cervical cancer, head and neck cancer, stomach cancer, breast cancer, renal cell cancer, CRC (colorectal cancer), (OC) ovarian cancer, NSCLC (non-small cell lung cancer).

25. A method for treatment of a disease or disorder mediated by GITR comprising administration in a subject in need of such treatment of a pharmaceutical composition according to claim 18 in a therapeutically effective amount.

26. The method for treatment of a disease or disorder according to claim 25, wherein the disease or disorder is selected from the group: cervical cancer, head and neck cancer, stomach cancer, breast cancer, renal cell cancer, CRC (colorectal cancer), (OC) ovarian cancer, NSCLC (non-small cell lung cancer).

* * * * *

SEQUENCE LISTING

<160> NUMBER OF SEQ ID NOS: 21

<210> SEQ ID NO 1
<211> LENGTH: 5
<212> TYPE: PRT
<213> ORGANISM: Artificial sequence
<220> FEATURE:
<223> OTHER INFORMATION: Artificial sequence HCDR1 BCD166-01/02-001

<400> SEQUENCE: 1

Asn Tyr Gly Met His
1               5

<210> SEQ ID NO 2
<211> LENGTH: 17
<212> TYPE: PRT
<213> ORGANISM: Artificial sequence
<220> FEATURE:
<223> OTHER INFORMATION: Artificial sequence HCDR2 BCD166-01/02-001

<400> SEQUENCE: 2

Val Ile Trp Phe Asp Gly Ser Asn Lys Phe Tyr Thr Asp Ser Val Lys
1               5                   10                  15

Gly

<210> SEQ ID NO 3
<211> LENGTH: 21
<212> TYPE: PRT
<213> ORGANISM: Artificial sequence
<220> FEATURE:
<223> OTHER INFORMATION: Artificial sequence HCDR3 BCD166-01/02-001

<400> SEQUENCE: 3

Glu Leu Gly Gly Tyr Tyr Tyr Asp Ser Ser Gly Phe Arg Pro Tyr Tyr
1               5                   10                  15

Tyr Gly Met Asp Val
            20

<210> SEQ ID NO 4
<211> LENGTH: 130
<212> TYPE: PRT
<213> ORGANISM: Artificial sequence
<220> FEATURE:
<223> OTHER INFORMATION: Artificial sequence BCD166-01/02-001_VH

<400> SEQUENCE: 4

Glu Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Lys Phe Tyr Thr Asp Ser Val
    50                  55                  60

Lys Gly Arg Phe Thr Ile Ser Arg Asp Asn Ser Lys Asp Thr Leu Ser
65                  70                  75                  80

Leu Gln Met Asn Ser Leu Arg Ala Glu Asp Thr Ala Val Tyr Tyr Cys
                85                  90                  95

Ala Arg Glu Leu Gly Gly Tyr Tyr Tyr Asp Ser Ser Gly Phe Arg Pro
            100                 105                 110

Tyr Tyr Tyr Gly Met Asp Val Trp Gly Gln Gly Thr Met Val Thr Val
        115                 120                 125

Ser Ser
    130

<210> SEQ ID NO 5
<211> LENGTH: 460
<212> TYPE: PRT
<213> ORGANISM: Artificial sequence
<220> FEATURE:
<223> OTHER INFORMATION: Artificial sequence BCD166-01-001_HC

<400> SEQUENCE: 5

Glu Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Lys Phe Tyr Thr Asp Ser Val
    50                  55                  60

Lys Gly Arg Phe Thr Ile Ser Arg Asp Asn Ser Lys Asp Thr Leu Ser
65                  70                  75                  80

Leu Gln Met Asn Ser Leu Arg Ala Glu Asp Thr Ala Val Tyr Tyr Cys
                85                  90                  95

Ala Arg Glu Leu Gly Gly Tyr Tyr Tyr Asp Ser Ser Gly Phe Arg Pro
            100                 105                 110

Tyr Tyr Tyr Gly Met Asp Val Trp Gly Gln Gly Thr Met Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

-continued

```
Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Gly Lys
        450                 455                 460

<210> SEQ ID NO 6
<211> LENGTH: 460
<212> TYPE: PRT
<213> ORGANISM: Artificial sequence
<220> FEATURE:
<223> OTHER INFORMATION: Artificial sequence BCD166-02-001_HC

<400> SEQUENCE: 6

Glu Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
                35                  40                  45

Ala Val Ile Trp Phe Asp Gly Ser Asn Lys Phe Tyr Thr Asp Ser Val
            50                  55                  60

Lys Gly Arg Phe Thr Ile Ser Arg Asp Asn Ser Lys Asp Thr Leu Ser
65                  70                  75                  80

Leu Gln Met Asn Ser Leu Arg Ala Glu Asp Thr Ala Val Tyr Tyr Cys
                85                  90                  95

Ala Arg Glu Leu Gly Gly Tyr Tyr Asp Ser Ser Gly Phe Arg Pro
                100                 105                 110

Tyr Tyr Tyr Gly Met Asp Val Trp Gly Gln Gly Thr Met Val Thr Val
                115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
                180                 185                 190

Tyr Ser Leu Ser Ser Val Val Thr Val Pro Ser Ser Ser Leu Gly Thr
                195                 200                 205

Gln Thr Tyr Ile Cys Asn Val Asn His Lys Pro Ser Asn Thr Lys Val
        210                 215                 220

Asp Lys Arg Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255
```

```
Pro Pro Lys Pro Lys Asp Thr Leu Met Ile Ser Arg Thr Pro Glu Val
        260                 265                 270

Thr Cys Val Val Asp Val Ser His Glu Asp Pro Glu Val Lys Phe
    275                 280                 285

Asn Trp Tyr Val Asp Gly Val Glu Val His Asn Ala Lys Thr Lys Pro
290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Arg Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 7
<211> LENGTH: 11
<212> TYPE: PRT
<213> ORGANISM: Artificial sequence
<220> FEATURE:
<223> OTHER INFORMATION: Artificial sequence LCDR1 BCD166-01/02-001

<400> SEQUENCE: 7

Arg Ala Ser Gln Ser Ile Gly Ser Trp Leu Ala
1               5                   10

<210> SEQ ID NO 8
<211> LENGTH: 7
<212> TYPE: PRT
<213> ORGANISM: Artificial sequence
<220> FEATURE:
<223> OTHER INFORMATION: Artificial sequence LCDR2 BCD166-01/02-001

<400> SEQUENCE: 8

Ala Ala Ser Thr Leu Gln Arg
1               5

<210> SEQ ID NO 9
<211> LENGTH: 9
<212> TYPE: PRT
<213> ORGANISM: Artificial sequence
<220> FEATURE:
<223> OTHER INFORMATION: Artificial sequence LCDR3 BCD166-01/02-001

<400> SEQUENCE: 9

Gln Gln Ser His Ser His Pro Leu Thr
1               5
```

```
<210> SEQ ID NO 10
<211> LENGTH: 107
<212> TYPE: PRT
<213> ORGANISM: Artificial sequence
<220> FEATURE:
<223> OTHER INFORMATION: Artificial sequence BCD166-01/02-001_VL

<400> SEQUENCE: 10

Asp Val Val Met Thr Gln Ser Pro Ser Ser Val Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Glu Ala Pro Lys Leu Leu Ile
        35                  40                  45

Tyr Ala Ala Ser Thr Leu Gln Arg Gly Val Pro Ser Arg Phe Ser Gly
50                  55                  60

Gly Gly Tyr Gly Thr Glu Phe Thr Leu Thr Ile Ser Ser Leu Gln Pro
65                  70                  75                  80

Glu Asp Phe Ala Thr Tyr Phe Cys Gln Gln Ser His Ser His Pro Leu
                85                  90                  95

Thr Phe Gly Gly Gly Thr Lys Val Glu Ile Lys
            100                 105

<210> SEQ ID NO 11
<211> LENGTH: 214
<212> TYPE: PRT
<213> ORGANISM: Artificial sequence
<220> FEATURE:
<223> OTHER INFORMATION: Artificial sequence BCD166-01/02-001_LC

<400> SEQUENCE: 11

Asp Val Val Met Thr Gln Ser Pro Ser Ser Val Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Glu Ala Pro Lys Leu Leu Ile
        35                  40                  45

Tyr Ala Ala Ser Thr Leu Gln Arg Gly Val Pro Ser Arg Phe Ser Gly
50                  55                  60

Gly Gly Tyr Gly Thr Glu Phe Thr Leu Thr Ile Ser Ser Leu Gln Pro
65                  70                  75                  80

Glu Asp Phe Ala Thr Tyr Phe Cys Gln Gln Ser His Ser His Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 12
<211> LENGTH: 5
<212> TYPE: PRT
<213> ORGANISM: Artificial sequence
<220> FEATURE:
<223> OTHER INFORMATION: Artificial sequence HCDR1 BCD166-01-014

<400> SEQUENCE: 12

Tyr Tyr Trp Met Tyr
1               5

<210> SEQ ID NO 13
<211> LENGTH: 17
<212> TYPE: PRT
<213> ORGANISM: Artificial sequence
<220> FEATURE:
<223> OTHER INFORMATION: Artificial sequence HCDR2 BCD166-01-014

<400> SEQUENCE: 13

Ala Ile Ser Trp Asn Gly Gly Arg Thr Tyr Tyr Ala Glu Ser Met Lys
1               5                   10                  15

Gly

<210> SEQ ID NO 14
<211> LENGTH: 13
<212> TYPE: PRT
<213> ORGANISM: Artificial sequence
<220> FEATURE:
<223> OTHER INFORMATION: Artificial sequence HCDR3 BCD166-01-014

<400> SEQUENCE: 14

Asn Arg Tyr Tyr Ser Asp Pro Asn Tyr Gly Met Asn Leu
1               5                   10

<210> SEQ ID NO 15
<211> LENGTH: 122
<212> TYPE: PRT
<213> ORGANISM: Artificial sequence
<220> FEATURE:
<223> OTHER INFORMATION: Artificial sequence BCD166-01-014_VH

<400> SEQUENCE: 15

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Trp Met Tyr Trp Val Arg Gln Ala Pro Gly Lys Gly Leu Glu Trp Val
        35                  40                  45

Ser Ala Ile Ser Trp Asn Gly Gly Arg Thr Tyr Tyr Ala Glu Ser Met
    50                  55                  60

Lys Gly Arg Phe Thr Ile Ser Arg Asp Asn Ala Gln Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Arg Tyr Tyr Ser Asp Pro Asn Tyr Gly Met Asn Leu Trp
            100                 105                 110

Gly Lys Gly Thr Thr Val Thr Val Ser Ser
        115                 120

```
<210> SEQ ID NO 16
<211> LENGTH: 452
<212> TYPE: PRT
<213> ORGANISM: Artificial sequence
<220> FEATURE:
<223> OTHER INFORMATION: Artificial sequence BCD166-01-014_HC

<400> SEQUENCE: 16

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Trp Met Tyr Trp Val Arg Gln Ala Pro Gly Lys Gly Leu Glu Trp Val
        35                  40                  45

Ser Ala Ile Ser Trp Asn Gly Gly Arg Thr Tyr Tyr Ala Glu Ser Met
    50                  55                  60

Lys Gly Arg Phe Thr Ile Ser Arg Asp Asn Ala Gln Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Arg Tyr Tyr Ser Asp Pro Asn Tyr Gly Met Asn Leu Trp
            100                 105                 110

Gly Lys Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
                435                 440                 445

Ser Pro Gly Lys
    450

<210> SEQ ID NO 17
<211> LENGTH: 14
<212> TYPE: PRT
<213> ORGANISM: Artificial sequence
<220> FEATURE:
<223> OTHER INFORMATION: Artificial sequence LCDR1 BCD166-01-014

<400> SEQUENCE: 17

Thr Gly Thr Ser Thr Asp Ile Gly Thr Tyr Lys Tyr Ile Ser
1               5                   10

<210> SEQ ID NO 18
<211> LENGTH: 7
<212> TYPE: PRT
<213> ORGANISM: Artificial sequence
<220> FEATURE:
<223> OTHER INFORMATION: Artificial sequence LCDR2 BCD166-01-014

<400> SEQUENCE: 18

Gly Val Ser His Arg Pro Ser
1               5

<210> SEQ ID NO 19
<211> LENGTH: 10
<212> TYPE: PRT
<213> ORGANISM: Artificial sequence
<220> FEATURE:
<223> OTHER INFORMATION: Artificial sequence LCDR3 BCD166-01-014

<400> SEQUENCE: 19

Ser Ser Tyr Thr Ser Ser Gly Thr Val Val
1               5                   10

<210> SEQ ID NO 20
<211> LENGTH: 110
<212> TYPE: PRT
<213> ORGANISM: Artificial sequence
<220> FEATURE:
<223> OTHER INFORMATION: Artificial sequence BCD166-01-014_VL

<400> SEQUENCE: 20

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Thr Asp Ile Gly Thr Tyr
            20                  25                  30

Lys Tyr Ile Ser Trp Tyr Gln Gln His Pro Gly Lys Ala Pro Lys Leu
        35                  40                  45

Ile Ile Tyr Gly Val Ser His Arg Pro Ser Gly Val Ser Asp Arg Phe
    50                  55                  60
```

```
Ser Gly Ser Lys Ser Asp Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Gly Thr Val Val Phe Gly Gly Gly Thr Lys Val Thr Val Leu
            100                 105                 110

<210> SEQ ID NO 21
<211> LENGTH: 216
<212> TYPE: PRT
<213> ORGANISM: Artificial sequence
<220> FEATURE:
<223> OTHER INFORMATION: Artificial sequence BCD166-01-014_LC

<400> SEQUENCE: 21

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Thr Asp Ile Gly Thr Tyr
                 20                  25                  30

Lys Tyr Ile Ser Trp Tyr Gln Gln His Pro Gly Lys Ala Pro Lys Leu
             35                  40                  45

Ile Ile Tyr Gly Val Ser His Arg Pro Ser Gly Val Ser Asp Arg Phe
 50                  55                  60

Ser Gly Ser Lys Ser Asp Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Gly Thr Val Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215
```